(12) United States Patent
Sommadossi et al.

(10) Patent No.: US 7,157,441 B2
(45) Date of Patent: Jan. 2, 2007

(54) METHODS AND COMPOSITIONS FOR TREATING HEPATITIS C VIRUS

(75) Inventors: Jean-Pierre Sommadossi, Birmingham, AL (US); Paulo LaColla, Cagliari (IT)

(73) Assignees: Idenix Pharmaceuticals, Inc., Cambridge, MA (US); Universita Degli Studi Di Cagliari, Cagliari (IT)

( * ) Notice: Subject to any disclaimer, the term of this patent is extended or adjusted under 35 U.S.C. 154(b) by 525 days.

(21) Appl. No.: 10/602,136

(22) Filed: Jun. 20, 2003

(65) Prior Publication Data

US 2005/0137161 A1    Jun. 23, 2005

Related U.S. Application Data

(62) Division of application No. 09/864,078, filed on May 23, 2001, now Pat. No. 6,914,054.

(60) Provisional application No. 60/206,585, filed on May 23, 2000.

(51) Int. Cl.
*A01N 43/04* (2006.01)
*A61K 31/70* (2006.01)

(52) U.S. Cl. .......................... 514/47; 514/43; 514/45; 514/46; 514/48

(58) Field of Classification Search ................ 514/43, 514/45, 46, 47, 48
See application file for complete search history.

(56) References Cited

U.S. PATENT DOCUMENTS

| | | | |
|---|---|---|---|
| 3,480,613 A | 11/1969 | Walton et al. | |
| 5,977,061 A | 11/1999 | Holy et al. | |
| 6,340,690 B1 | 1/2002 | Bachand et al. | |
| 6,348,587 B1 | 2/2002 | Schinazi et al. | |
| 6,395,716 B1 | 5/2002 | Gosselin et al. | |
| 6,444,652 B1 | 9/2002 | Gosselin et al. | |
| 6,495,677 B1 | 12/2002 | Ramasamy et al. | |
| 6,573,248 B1 | 6/2003 | Ramasamy et al. | |
| 6,660,721 B1 | 12/2003 | Devos et al. | |
| 6,777,395 B1 | 8/2004 | Bhat et al. | |
| 6,784,166 B1 | 8/2004 | Devos et al. | |
| 6,846,810 B1 | 1/2005 | Martin et al. | |
| 6,911,424 B1 | 6/2005 | Schinazi et al. | |
| 2002/0019363 A1 | 2/2002 | Ismaili et al. | |
| 2002/0055483 A1 | 5/2002 | Watanabe et al. | |
| 2002/0095033 A1 | 7/2002 | Ramasamy et al. | |
| 2002/0147160 A1 | 10/2002 | Bhat et al. | |
| 2002/0198171 A1 | 12/2002 | Schinazi et al. | |
| 2003/0008841 A1 | 1/2003 | Devos et al. | |
| 2003/0028013 A1 | 2/2003 | Wang et al. | |
| 2003/0050229 A1 | 3/2003 | Sommadossi et al. | |
| 2003/0060400 A1 | 3/2003 | LaColla et al. | |
| 2003/0083307 A1 | 5/2003 | Devos et al. | |
| 2003/0087873 A1 | 5/2003 | Stuyver et al. | |
| 2003/0225029 A1 | 12/2003 | Stuyver et al. | |
| 2003/0236216 A1 | 12/2003 | Devos et al. | |
| 2004/0002476 A1 | 1/2004 | Stuyver et al. | |
| 2004/0023921 A1 | 2/2004 | Yao et al. | |
| 2004/0059104 A1 | 3/2004 | Cook et al. | |
| 2004/0063658 A1 | 4/2004 | Roberts et al. | |
| 2004/0067901 A1 | 4/2004 | Bhat et al. | |
| 2004/0072788 A1 | 4/2004 | Bhat et al. | |
| 2004/0110717 A1 | 6/2004 | Bhat et al. | |
| 2004/0110718 A1 | 6/2004 | Devos et al. | |
| 2004/0121980 A1 | 6/2004 | Martin et al. | |
| 2004/0147464 A1 | 7/2004 | Roberts et al. | |
| 2004/0266722 A1 | 12/2004 | Devos et al. | |
| 2005/0119200 A1 | 6/2005 | Roberts et al. | |

FOREIGN PATENT DOCUMENTS

| | | |
|---|---|---|
| FR | 1521076 A | 4/1968 |
| FR | 1581628 A | 9/1969 |
| FR | 2662165 A | 11/1991 |
| GB | 1163103 A | 9/1969 |
| GB | 1209654 A | 10/1970 |
| JP | 63-215694 A | 9/1988 |
| JP | 06-228186 A | 8/1994 |
| WO | WO 98/16184 A2 | 4/1998 |
| WO | WO 99/43691 A1 | 2/1999 |
| WO | WO 00/09531 A2 | 2/2000 |
| WO | WO 01/32153 A2 | 5/2001 |
| WO | WO 01/91737 A2 | 6/2001 |
| WO | WO 01/92282 A2 | 6/2001 |
| WO | WO 01/60315 A2 | 8/2001 |
| WO | WO 01/68663 A1 | 9/2001 |
| WO | WO 01/79246 A2 | 10/2001 |
| WO | WO 01/90121 A2 | 11/2001 |
| WO | WO 01/96353 A2 | 12/2001 |
| WO | WO 02/03997 A1 | 1/2002 |
| WO | WO 02/18404 A2 | 3/2002 |
| WO | WO 02/32920 A2 | 4/2002 |
| WO | WO 02/48165 A2 | 6/2002 |
| WO | WO 02/057287 A2 | 7/2002 |
| WO | WO 02/057425 A2 | 7/2002 |
| WO | WO 02/070533 A2 | 9/2002 |
| WO | WO 02/094289 A1 | 11/2002 |

(Continued)

OTHER PUBLICATIONS

Harry-O'kuru et al. Nucleotides & Nucleosides (1997), vol. 16, pp. 1457-1460.*

(Continued)

*Primary Examiner*—Patrick Lewis
(74) *Attorney, Agent, or Firm*—Sherry M. Knowles, Esq.; King & Spalding LLP

(57) ABSTRACT

A method and composition for treating a host infected with hepatitis C comprising administering an effective hepatitis C treatment amount of a described 1', 2' or 3'-modified nucleoside or a pharmaceutically acceptable salt or prodrug thereof, is provided.

39 Claims, 3 Drawing Sheets

FOREIGN PATENT DOCUMENTS

| | | |
|---|---|---|
| WO | WO 02/100415 A2 | 12/2002 |
| WO | WO 03/026589 A2 | 4/2003 |
| WO | WO 03/026675 A1 | 4/2003 |
| WO | WO 03/051899 A1 | 6/2003 |
| WO | WO 03/061385 A1 | 7/2003 |
| WO | WO 03/061576 A2 | 7/2003 |
| WO | WO 03/062255 A2 | 7/2003 |
| WO | WO 03/062256 A1 | 7/2003 |
| WO | WO 03/062257 A1 | 7/2003 |
| WO | WO 03/063771 A2 | 8/2003 |
| WO | WO 03/068162 A2 | 8/2003 |
| WO | WO 03/068164 A2 | 8/2003 |
| WO | WO 03/072757 A2 | 9/2003 |
| WO | WO 03/093290 A2 | 11/2003 |
| WO | WO 04/000858 A2 | 12/2003 |
| WO | WO 04/002422 A2 | 1/2004 |
| WO | WO 04/002999 A2 | 1/2004 |
| WO | WO 04/003138 A2 | 1/2004 |
| WO | WO 04/007512 A2 | 1/2004 |
| WO | WO 04/009020 A2 | 1/2004 |
| WO | WO 04/028481 A2 | 4/2004 |
| WO | WO 04/046159 A1 | 6/2004 |

OTHER PUBLICATIONS

Altmann et al, "The synthesis of 1'-methyl carbocyclic thymidine and its effect on nucleic acid duplex stability," *Synlett, Thieme Verlag, Stuttgart, De*, 10:853-855 (1994).

Baginski, S. G, et al., "Mechanism of action of a pestivirus antiviral compound," *PNAS USA*, 97(14):7981-7986 (2000).

Beigelman, L.N., et al, "Epimerization during the acetolysis of 3-O-acetyl-5-O-benzoyl-1,2-O-isopropylidene-3-C-methyl-α,D-ribofuranose. Synthesis of 3'-C-methylnucleosides with the β-D-*ribo*- and α-D-*arabino* configurations," *Carbohydrate Research*, 181:77-88 (1988).

Beigelman, L.N., et al, "A general method for synthesis of 3'-C-alkylnucleosides," *Nucleic Acids Symp. Ser.*, 9:115-118 (1981).

Berenguer, M., et al, "Hepatitis B and C viruses: Molecular identification and targeted antiviral therapies," *Proceedings of the Association of American Physicians*, 110(2), 98-112 (1998).

Carroll, S.S., et al., "Inhibition of hepatitis C virus RNA replication by 2'-modified nucleoside analogs," *The Journal of Biological Chemistry*, 278(14):11979-11984 (2003).

Czernecki, S., et al, "Synthesis of various 3'-branched 2',3'-unsaturated pyrimidine nucleosides as potential anti-HIV agents," *J. Org. Chem.*, 57:7325-7328 (1992).

DeFrancesco, R., et al., "Approaching a new era for hepatitis C virus therapy: Inhibitors of the NS3-4A serine protease and the NS5B RNA-dependent RNA polymerase," *Antiviral Research*, 58:1-16 (2003).

Faivre-Buet, V., et al, "Synthesis of 1'-deoxypsicofuranosyl-deoxynucleosides as potential anti-HIV agents," *Nucleosides & Nucleotides*, 11(7):1411-1424 (1992).

Farkas, J., et al., "Nucleic acid components and their analogues. XCIV. Synthesis of 6-amino-9-(1-deoxy-β-D-psicofuranosyl)purine", *Collect. Czech. Chem. Commun.* 32:2663-2667 (1967).

Farkas, J., et al., "Nucleic acid components and their analogues. LXXIX. Synthesis of methyl 1-deoxy-D-psicofuranosides substituted at $C_{(1)}$ with halo atoms or a mercapto group," *Collect. Czech. Chem. Commun.*, 31:1535-1543 (1996).

Fedorov, I.I., et al, "3'-C-Branched 2'-deoxy-5-methyluridines: Synthesis, enzyme inhibition, and antiviral properties," *J. Med. Chem.*, 35(24):4567-4575 (1992).

Franchetti, P., et al., "2'-C-Methyl analogues of selective adenosine receptor agonists: synthesis and binding studies," *J. Med. Chem.*, 41(10):1708-1715 (1998).

Grouiller, A., et al., "Novel p-toluenesulfonylation and thionocarbonylation of unprotected thymine nucleosides," *Synlett*, 1993, 221-222 (Mar. 1993).

Haraguchi, K., et al., "Preparation and reactions of 2'- and 3'- vinyl bromides of uracil nucleosides: Versatile synthons for anti-HIV agents," *Tetrahedron Letters*, 32(28):3391-3394 (1991).

Haraguchi, K., et al., "Stereoselective synthesis of 1'-C-branched uracil nucleosides from uridine," *Nucleosides & Nucleotides*, 14(3-5):417-420 (1995).

Harry-O'Kuru, R.E., et al., "A short, flexible route toward 2'-C-branched ribonucleosides", *J.Org. Chem.*, 62:1754-1759 (1997). (Scheme 11).

Harry-O'Kuru, R.E., et al., "2'-C-Alkylribonucleosides: Design, synthesis, and conformation," *Nucleosides & Nucleotides*, 16(7-9): 1457-1460 (1997). ["Rogers" in #2; correct name in #7].

Hattori, H., et al, "Nucleosides and nucleotides. 175. Structural requirements of the sugar moiety for the antitumor activities of new nucleoside antimetabolites, 1-(3-C-ethynyl-b-D-ribopentofuranosyl)cytosine and -uracil," *J. Med. Chem.*, 41:2892-2902 (1998).

Hrebabecky, H., et al., "Nucleic acid components and their analogues. CXLIX. Synthesis of pyrimidine nucleosides derived from 1-deoxy-D-psicose," *Collect. Czech. Chem. Commun.*, 37:2059-2065 (1972).

Hrebabecky, H., et al. "Synthesis of 7- and 9β-D-psicofuranosylguanine and their 1'-deoxy derivatives," *Collect. Czech. Chem. Commun.*, 39:2115-2123 (1974).

Iino, T., et al., "Nucleosides and nucleotides. 139. Stereoselective synthesis of (2'S)-2'-C-alkyl-2'-deoxyuridines," *Nucleosides and Nucleotides*, 15(1-3):169-181 (1996).

Itoh, Y., et al, "Diverrgent and stereocontrolled approach to the synthesis of uracil nucleosides branched at the anomeric position," *J. Org. Chem.*, 60(3):656-662 (1995).

Johnson, C.R., et al, "3'-C-Trifluoromethyl ribonucleosides," *Nucleosides & Nucleotides*, 14(1&2):185-194 (1995).

Kawana, M., et al., "The deoxygenation of tosylated adenosine derivatives with Grignard reagents," *Nucleic Acids Symp. Ser.*, 17:37-40 (1986).

Lavaire, S., et al., "3'-Deoxy-3'-C-trifluoromethyl nucleosides: Synthesis and antiviral evaluation," *Nucleosides & Nucleotides*, 17(12):2267-2280 (1998).

Leyssen, P. et al., "Perspectives for the treatment of infections with *Flaviviridae*," *Clinical Microbiology Reviews* (Washington, D.C.), 13(1):67-82 (Jan. 2000).

Martin, X., et al., "Intramolecular hydrogen bonding in primary hydroxyl of thymine 1-(1-deoxy-β-D-psicofuranosyl) nucleoside," *Tetrahedron*, 50(22):6689-6694 (1994).

Matsuda, A., et al., "Radical deoxygenation of *tert*-alcohols in 2'-branched-chain sugar pyrimidine nucleosides: Synthesis and antileukemic activity of 2'-deoxy-2'(S)-methylcytidine," *Chem. Pharm. Bull.*, 35(9):3967-3970 (1987).

Matsuda, A., et al., "Alkyl addition reaction of pyrimidine 2'-ketonucleosides: Synthesis of 2'-branched-chain sugar pyrimidine nucleosides (Nucleosides and Nucleotides. LXXXI)," *Chem. Pharm. Bull.*, 36(3):945-953 (1988).

Matsuda, A., et al., "Nucleosides and Nucleotides. 94. Radical deoxygenation of *tert*-alcohols in 1-(2-C-alkylpentofuranosyl)pyrimidines: Synthesis of (2'S)-2'-deoxy-2'-C-methylcytidine, an antileukemic nucleoside," *J. Med. Chem.*, 34:234-239 (1991).

Matsuda, A., et al., "Nucleosides and Nucleotides. 104. Radical and palladium-catalyzed deoxygenation of the allylic alcohol systems in the sugar moiety of pyrimidine nucleosides," *Nucleosides & Nucleotides*, 11(2/4):197-226 (1992).

Mikhailov, S.N., et al., "Synthesis and properties of 3'C-methylnucleosides and their phosphoric esters," *Carbohydrate Research*, 124:75-96 (1983).

Mikhailov, S.N., et al., "Substrate properties of C'-methylnucleoside and C'-methyl-2'-deoxynucleoside 5'-triphosphates in RNA and DNA synthesis reactions catalysed by RNA and DNA polymerases," *Nucleosides & Nucleotides*, 10(1-3):339-343 (1991).

Mikhailov, S.N., et al, "Hydrolysis of 2'- and 3'-C-methyluridine 2'c3'-cyclic monophosphates and interconversion and dephosphorylation of the resuling 2'- and 3'-monophosphates: Comparison with the reactions of uridine monophosphates," *J. Org. Chem.*, 57 (15):4122-4126 (1992).

Nutt, R.F., et al., "Branched-chain sugar nucleosides. III. 3'-C-methyladenine", *J.Org. Chem.*, 33:1789-1795 (1968).

Oivanen, M., et al, "Additional evidence for the exceptional mechanism of the acid-catalyzed hydrolysis of 4-oxopyrimidine nucleosides: Hydrolysis of 1-(1-alkoxyalkyl)uracils, seconucleosides, 3'-C-alkyl nucleosides and nucleoside 3',5'-cyclic monophosphates," *J. Chem. Soc. Perkin Trans.* 2, 1994:309-314 (1994).

Ong, S.P., et al, "Synthesis of 3'-C-methyladenosine and 3'-C-methyluridine diphosphates and their interaction with the ribonucleoside diphosphate reductase from *Corynebacterium nephridii*," *Biochemistry*, 31(45):11210-11215 (1992).

Oral Session V, Hepatitis C Virus, Flaviviridae; 16th International Conference on Antiviral Research (Apr. 27, 2003, Savannah, Ga.) p. A75-77.

Pan-Zhou, X-R, et al., "Differential effects of antiretroviral nucleoside analogs on mitochondrial function in HepG2 cells," *Antimicrob. Agents Chemother.*, 44:496-503 (2000).

Rosenthal, A., et al., Branched-chain sugar nucleosides. Synthesis of 3'-C-ethyl (and 3'-C-butyl)uridine *Carbohydrate Research*, 79:235-242 (1980).

Samano, V., et al., "Synthesis and radical-induced ring-opening reactions of 2'-deoxyadenosine-2'-spirocyclopropane and its uridine analogue. Mechanistic probe for ribonucleotide reductases," *J. Am. Chem. Soc.*, 114:4007-4008 (1992).

Samano, V., et al., "Nucleic acid related compounds. 77. 2',3'-Didehydro-2',3'-dideoxy-2'(and 3')-methylnucleosides via [3,3]-sigmatropic rearrangements of 2'(and 3')-methylene-3'(and 2')-O-thiocarbonyl derivatives and radical reduction of a 2'-chloro-3'-methylene analogue," *Can. J. Chem.*, 71:186-191 (1993).

Schmit, C., et al, "The effects of 2'- and 3'-alkyl substituents on oligonucleotide hybridization and stability," *Biorganic & Medicinal Chemistry Letters*, 4(16):1969-1974 (1994). ["Altmann"].

Serafinowski, P.J., et al., "New method for the preparation of some 2'- and 3'-trifluoromethyl-2',3'-dideoxyuridine derivatives," *Tetrahedron* (Elsevier Science Publishers), 56(2):333-339 (1999).

Sharma, P.K., et al., "Synthesis of 3'-trifluoromethyl nucleosides as potential antiviral agents," *Nucleosides, Nucleotides and Nucleic Acids*, 19(4):757-774 (2000).

Sommadossi J-P, et al., "Comparison of cytotoxicity of the (−)- and (+)-enantiomer of 2',3'-dideoxy-3'-thiacytidine in normal human bone marrow progenitor cells" *Biochemical Pharmacology*, 44:1921-1925 (1992).

Sommadossi J-P, et al., "Toxicity of 3'-azido-3'-deoxythymidine and 9-(1,3-dihydroxy-2-propoxymethyl)guanine for normal human hematopoietic progenitor cells in vitro" *Antimicrobial Agents and Chemotherapy*, 31:452-454 (1987).

Tritsch, D., et al., "3'-β-ethynyl and 2'-deoxy-3'-β-ethynyl adenosines: First 3'-β-branched adenosines substrates of adenosine deaminase," *Bioorganic & Medicinal Chemistry Letters*, 10:139-141 (2000).

Tunitskaya, V.L., et al., "Substrate properties of C'-methyl UTP derivatives in T7 RNA polymerase reactions. Evidence for N-type NTP conformation," *FEBS Letters*, 400:263-266 (1997).

Usui, H., et al., "Synthesis of 2'-deoxy-8,2'-ethanoadenosine and 3'-deoxy-8,3'-ethanoadenosine (Nucleosides and Nucleotides. LXIV)," *Chem. Pharm. Bull.*, 34(1):15-23 (1986).

Walczak, K., et al., "Synthesis of 1-(3-alkyl-2,3-dideoxy-D-pentofuranosyl)uracils with potential anti-HIV activity," *Acta Chemica Scand.*, 45:930-934 (1991).

Walton, E., et al., "Branched-chain sugar nucleosides. V. Synthesis and antiviral properties of several branched-chain sugar nucleotides," *J. Med. Chem.*, 12:306-309 (1969).

Wolfe, M.S., et al., "A concise synthesis of 2'-C-methylribonucleosides," *Tetrahedron Letters*, 36(42):7611-7614 (1995).

Wu, J.-C., et al., A new stereospecific synthesis of [3.1.0] bicyclic cyclopropano analog of 2',3'-dideoxyuridine, *Tetrahedron*, 46(7):2587-2592 (1990).

* cited by examiner

Chemical Structure of Illustrative Nucleosides

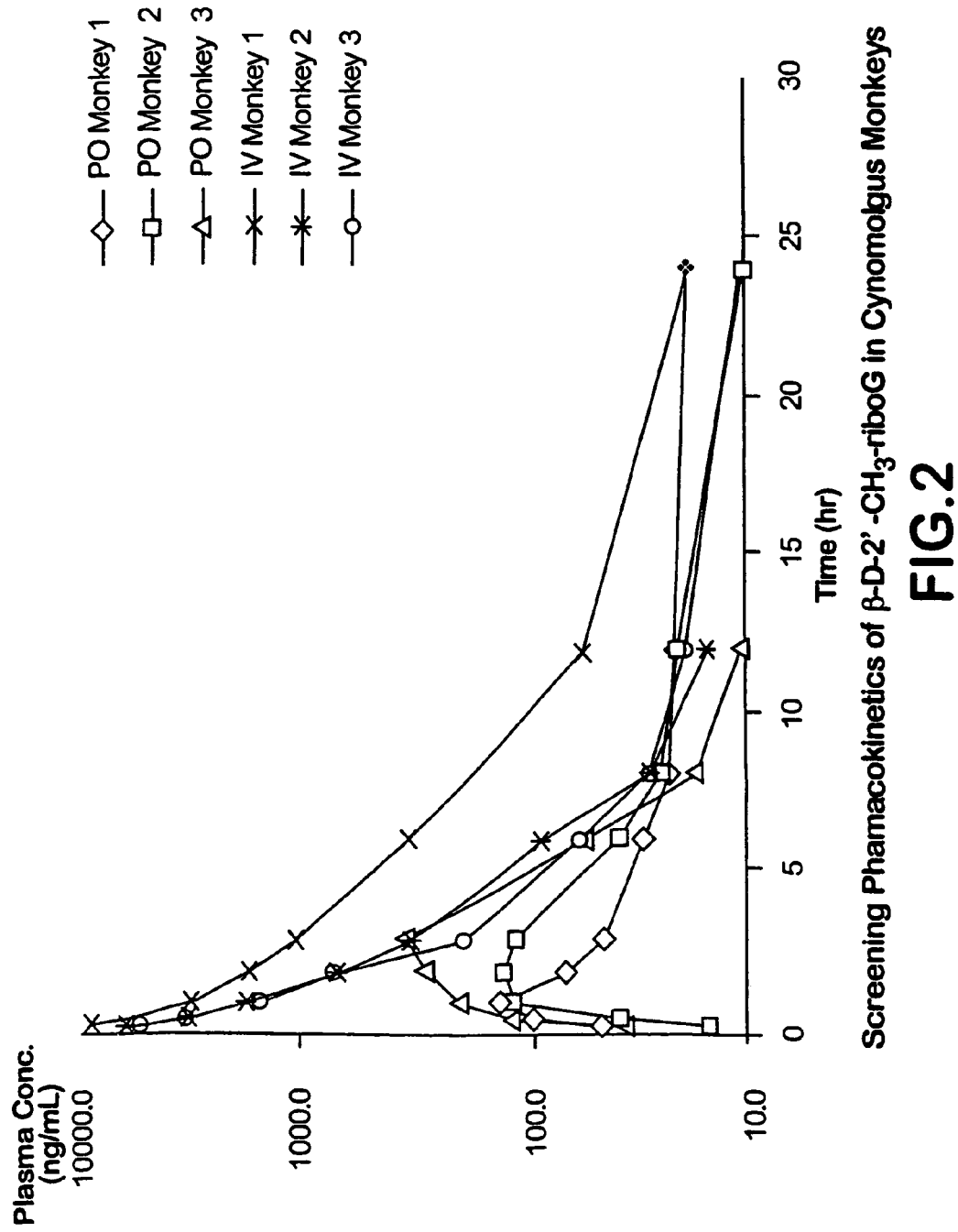

Screening Phamacokinetics of β-D-2'-CH$_3$-riboG
in Cynomolgus Monkeys

Screening Phamacokinetics of β-D-2'-CH$_3$-riboG
in Cynomolgus Monkeys

METHODS AND COMPOSITIONS FOR TREATING HEPATITIS C VIRUS

FIELD OF THE INVENTION

This invention is in the area of pharmaceutical chemistry, and in particular, is a compound, method and composition for the treatment of hepatitis C virus. This application is a divisional of U.S. application Ser. No. 09/864,078, filed on May 23, 2001, now U.S. Pat. No. 6,914,054 which claims priority to U.S. provisional application No. 60/206,585, filed on May 23, 2000, the disclosures of which are incorporated herein by reference.

BACKGROUND OF THE INVENTION

The hepatitis C virus (HCV) is the leading cause of chronic liver disease worldwide. (Boyer, N. et al. *J. Hepatol.* 32:98–112, 2000). HCV causes a slow growing viral infection and is the major cause of cirrhosis and hepatocellular carcinoma (Di Besceglie, A. M. and Bacon, B. R., *Scientific American*, October: 80–85, (1999); Boyer, N. et al. *J. Hepatol.* 32:98–112, 2000). An estimated 170 million persons are infected with HCV worldwide. (Boyer, N. et al. *J. Hepatol.* 32:98–112, 2000). Cirrhosis caused by chronic hepatitis C infection accounts for 8,000–12,000 deaths per year in the United States, and HCV infection is the leading indication for liver transplant.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: Fields, B. N., Knipe, D. M., and Howley, P. M., Lippincott-Raven Publishers, Philadelphia, Pa., Chapter 30, 931–959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed toward the development of improved methods of treatment of chronic HCV infections in humans (Di Besceglie, A. M. and Bacon, B. R., *Scientific American*, October: 80–85, (1999)). Currently, there are two primary antiviral compounds, Ribavirin and interferon-alpha, which are used for the treatment of chronic HCV infections in humans.

Treatment of HCV Infection with Ribivarin

Ribavirin (1-β-D-ribofuranosyl-1-1,2,4-triazole-3-carboxamide) is a synthetic, non-interferon-inducing, broad spectrum antiviral nucleoside analog sold under the trade name, Virazole (The Merck Index, 11th edition, Editor: Budavari, S., Merck & Co., Inc., Rahway, N.J., p1304, 1989). U.S. Pat. No. 3,798,209 and RE29,835 disclose and claim Ribavirin. Ribavirin is structurally similar to guanosine, and has in vitro activity against several DNA and RNA viruses including Flaviviridae (Gary L. Davis. *Gastroenterology* 118: S104-S114, 2000).

Ribavirin reduces serum amino transferase levels to normal in 40% or patients, but it does not lower serum levels of HCV-RNA (Gary L. Davis. *Gastroenterology* 118: S104-S114, 2000). Thus, Ribavirin alone is not effective in reducing viral RNA levels. Additionally, Ribavirin has significant toxicity and is known to induce anemia.

Treatment of HCV Infection with Interferon

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%–9% of patients chronically infected with HCV (Gary L. Davis. *Gastroenterology* 118: S104–S114, 2000).

A number of patents disclose HCV treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Inakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696.

Combination of Interferon and Ribavirin

The combination of IFN and Ribavirin for the treatment of HCV infection has been reported to be effective in the treatment of IFN naive patients (Battaglia, A. M. et al., *Ann. Pharmacother.* 34:487–494, 2000). Results are promising for this combination treatment both before hepatitis develops or when histological disease is present (Berenguer, M. et al. *Antivir. Ther.* 3(Suppl. 3):125–136, 1998). Side effects of combination therapy include hemolysis, flu-like symptoms, anemia, and fatigue. (Gary L. Davis. *Gastroenterology* 118: S104–S114, 2000).

Additional References Disclosing Methods to Treat HCV Infections

A number of HCV treatments are reviewed by Bymock et al. in *Antiviral Chemistry & Chemotherapy*, 11:2; 79–95 (2000).

Several substrate-based NS3 protease inhibitors have been identified in the literature, in which the scissile amide bond of a cleaved substrate is replaced by an electrophile, which interacts with the catalytic serine. Attwood et al. (1998). *Antiviral peptide derivatives,* 98/22496; Attwood et al. (1999), *Antiviral Chemistry and Chemotherapy* 10.259–273; Attwood et al. (1999) *Preparation and use of amino acid derivatives as anti-viral agents*, German Patent Publication DE 19914474; Tung et al. (1998) *Inhibitors of serine proteases, particularly hepatitis C virus NS3 protease*, WO 98/17679. The reported inhibitors terminate in an electrophile such as a boronic acid or phosphonate. Llinas-Brunet et al. (1999) *Hepatitis C inhibitor peptide analogues*, WO 99/07734. Two classes of electrophile-based inhibitors have been described, alphaketoamides and hydrazinoureas.

The literature has also described a number of non-substrate-based inhibitors. For example, evaluation of the inhibitory effects of 2,4,6-trihydroxy-3-nitro-benzamide derivatives against HCV protease and other serine proteases has been reported. Sudo, K. et al., (1997) *Biochemical and Biophysical Research Communications*, 238:643–647; Sudo, K. et al. (1998) *Antiviral Chemistry and Chemotherapy* 9:186. Using a reverse-phase HPLC assay, the two most potent compounds identified were RD3-4082 and RD3-4078, the former substituted on the amide with a 14 carbon chain and the latter processing a para-phenoxyphenyl group.

Thiazolidine derivatives have been identified as micromolar inhibitors, using a reverse-phase HPLC assay with an NS3/4A fusion protein and NS5A/5B substrate. Sudo, K. et al. (1996) *Antiviral Research* 32:9–18. Compound RD-1-6250, possessing a fused cinnamoyl moiety substituted with a long alkyl chain, was the most potent against the isolated enzyme. Two other active examples were RD4 6205 and RD4 6193.

Other literature reports screening of a relatively small library using an ELISA assay and the identification of three compounds as potent inhibitors, a thiazolidine and two benzanilides. Kakiuchi N. et al. *J. EBS Letters* 421:217–220; Takeshita N. et al., *Analytical Biochemistry* 247:242–246, 1997. Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al.

Isolated from the fermentation culture broth of *Streptomyces* sp., Sch 68631, a phenan-threnequinone, possessed micromolar activity against HCV protease in a SDS-PAGE and autoradiography assay. Chu M. et al., *Tetrahedron Letters* 37:7229–7232, 1996. In another example by the same authors, Sch 351633, isolated from the fungus *Penicillium griscofuluum*, demonstrated micromolar activity in a scintillation proximity assay. Chu M. et al., *Bioorganic and Medicinal Chemistry Letters* 9:1949–1952. Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin. Qasim M. A. et al., *Biochemistry* 36:1598–1607, 1997.

HCV helicase inhibitors have also been reported. U.S. Pat. No. 5,633,358 to Diana G. D. et al.; PCT Publication No. WO 97/36554 of Diana G. D. et al. There are a few reports of HCV polymerase inhibitors: some nucleotide analogues, gliotoxin and the natural product cerulenin. Ferrari R. et al., *Journal of Virology* 73:1649–1654, 1999; Lohmann V. et al., *Virology* 249:108–118, 1998.

Antisense phosphorothioate oligodeoxynucleotides complementary to sequence stretches in the 5' non-coding region of the HCV, are reported as efficient inhibitors of HCV gene expression in in vitro translation and IIcpG2 IICV-luciferase cell culture systems. Alt M. et al., *Hepatology* 22:707–717, 1995. Recent work has demonstrated that nucleotides 326–348 comprising the 3' end of the NCR and nucleotides 371–388 located in the core coding region of the HCV RNA are effective targets for antisense-mediated inhibition of viral translation. Alt M. et al., *Archives of Virology* 142:589–599, 1997. U.S. Pat. No. 6,001,990 to Wands et al. discloses oligonucleotides for inhibiting the replication of HCV. PCT Publication No. WO 99/29350 discloses compositions and methods of treatment for hepatitis C infection comprising the administration of antisense oligonucleotides that are complementary and hybridizable to HCV-RNA. U.S. Pat. No. 5,922,857 to Han et al. disclose nucleic acids corresponding to the sequence of the pestivirus homology box IV area for controlling the translation of HCV. Antisense oligonucleotides as therapeutic agents have been recently reviewed (Galderisi U. et al., *Journal of Cellular Physiology* 181:251–257, 1999).

Other compounds have been reported as inhibitors of IRES-dependent translation in HCV. Japanese Patent Publication JP-08268890 of Ikeda N et al.; Japanese Patent Publication JP-10101591 of Kai, Y. et al. Nuclease-resistant ribozymes have been targeted at the IRES and recently reported as inhibitors in an HCV-poliovirus chimera plaque assay. Maccjak D. J. et al., *Hepatology* 30 abstract 995, 1999. The use of ribozymes to treat HCV is also disclosed in U.S. Pat. No. 6,043,077 to Barber et al., and U.S. Pat. Nos. 5,869,253 and 5,610,054 to Draper et al.

Other patents disclose the use of immune system potentiating compounds for the treatment of HCV. For example, U.S. Pat. No. 6,001,799 to Chretien et al. discloses a method of treating hepatitis C in non-responders to interferon treatment by administering an immune system potentiating dose of thymosin or a thymosin fragment. U.S. Pat. No. 5,972,347 to Eder et al. and U.S. Pat. No. 5,969,109 to Bona et al. disclose antibody-based treatments for treating HCV.

U.S. Pat. No. 6,034,134 to Gold et al. discloses certain NMDA receptor agonists having immunodulatory, antimalarial, anti-Borna virus and anti-Hepatitis C activities. The disclosed NMDA receptor agonists belong to a family of 1-amino-alkylcyclohexanes. U.S. Pat. No. 6,030,960 to Morris-Natschke et al. discloses the use of certain alkyl lipids to inhibit the production of hepatitis-induced antigens, including those produced by the HCV virus. U.S. Pat. No. 5,922,757 to Chojkier et al. discloses the use of vitamin E and other antioxidants to treat hepatic disorders including HCV. U.S. Pat. No. 5,858,389 to Elsherbi et al. discloses the use of squalene for treating hepatitis C. U.S. Pat. No. 5,849,800 to Smith et al discloses the use of amantadine for treatment of Hepatitis C. U.S. Pat. No. 5,846,964 to Ozeki et al. discloses the use of bile acids for treating HCV. U.S. Pat. No. 5,491,135 to Blough et al. discloses the use of N-(phosphonoacetyl)-L-aspartic acid to treat flaviviruses such as HCV.

Other compounds proposed for treating HCV include plant extracts (U.S. Pat. No. 5,837,257 to Tsai et al., U.S. Pat. No. 5,725,859 to Omer et al., and U.S. Pat. No. 6,056,961), piperidenes (U.S. Pat. No. 5,830,905 to Diana et al.), benzenedicarboxamides U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.).

In light of the fact that the hepatitis C virus has reached epidemic levels worldwide, and has tragic effects on the infected patient, there remains a strong need to provide new effective pharmaceutical agents to treat hepatitis C that has low toxicity to the host.

Therefore, it is an object of the present invention to provide a compound, method and composition for the treatment of a host infected with hepatitis C virus.

SUMMARY OF THE INVENTION

Compounds, methods and compositions for the treatment of hepatitis C infection are described that include an effective hepatitis C treatment amount of a β-D- or β-L-nucleoside of the Formulas (I)–(XVIII), or a pharmaceutically acceptable salt or prodrug thereof.

In a first principal embodiment, a compound of Formula I, or a pharmaceutically acceptable salt or prodrug thereof, is provided:

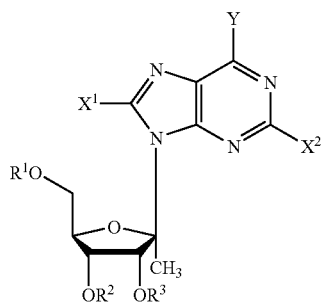

(I)

wherein:
$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a second principal embodiment, a compound of Formula II, or a pharmaceutically acceptable salt or prodrug thereof, is provided:

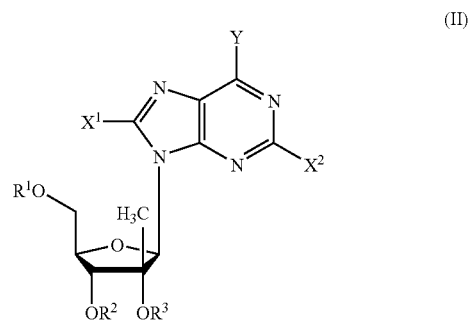

(II)

wherein:
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a third principal embodiment, a compound of Formula III, or a pharmaceutically acceptable salt or prodrug thereof, is provided:

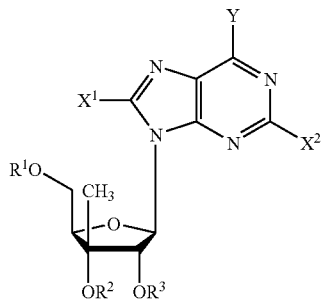

(III)

wherein:
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a fourth principal embodiment, a compound of Formula IV, or a pharmaceutically acceptable salt or prodrug thereof, is provided:

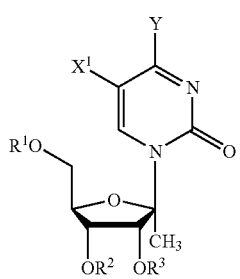

(IV)

wherein:
$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a fifth principal embodiment, a compound of Formula V, or a pharmaceutically acceptable salt or prodrug thereof, is provided:

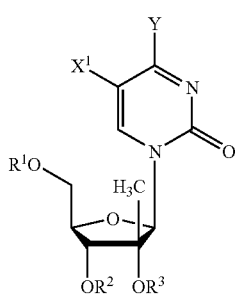

(V)

wherein:
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of. providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a sixth principal embodiment, a compound of Formula VI, or a pharmaceutically acceptable salt or prodrug thereof, is provided:

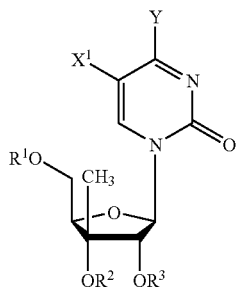

(VI)

wherein:
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a seventh principal embodiment, a compound selected from Formulas VII, VIII and IX, or a pharmaceutically acceptable salt or prodrug thereof, is provided:

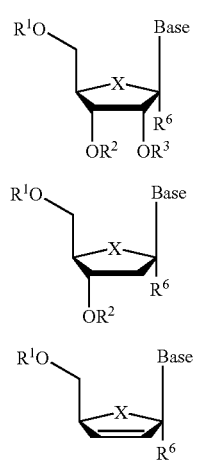

wherein:
Base is a purine or pyrimidine base as defined herein;
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$ or $CH_2$.

In a eighth principal embodiment, a compound of Formulas X, XI and XII, or a pharmaceutically acceptable salt or prodrug thereof, is provided:

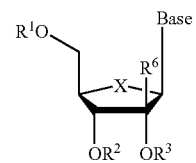

(X)

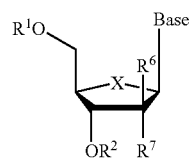

(XI)

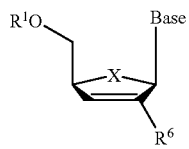

(XII)

wherein:
Base is a purine or pyrimidine base as defined herein;
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$; and, X is O, S, $SO_2$ or $CH_2$.

In a ninth principal embodiment a compound selected from Formulas XIII, XIV and XV, or a pharmaceutically acceptable salt or prodrug thereof, is provided:

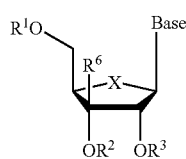

(XIII)

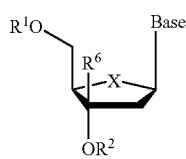

(XIV)

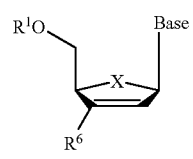

(XV)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$ or $CH_2$.

In a tenth principal embodiment the invention provides a compound of Formula XVI, or a pharmaceutically acceptable salt or prodrug thereof:

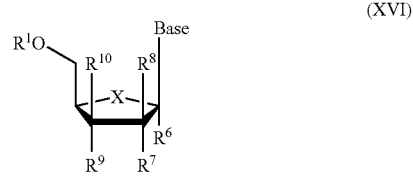

(XVI)

wherein:

Base is a purine or pyrimidine base as defined herein;

$R^1$ and $R^2$, are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ and $R^{10}$ are independently H, alkyl (including lower alkyl), chlorine, bromine or iodine;

alternatively, $R^7$ and $R^9$, $R^7$ and $R^{10}$, $R^8$ and $R^9$, or $R^8$ and $R^{10}$ can come together to form a pi bond; and X is O, S, $SO_2$ or $CH_2$.

In a eleventh principal embodiment the invention provides a compound of Formula XVII, or a pharmaceutically acceptable salt or prodrug thereof:

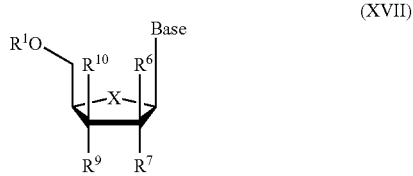

(XVII)

wherein:

Base is a purine or pyrimidine base as defined herein;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^{10}$ is H, alkyl (including lower alkyl),. chlorine, bromine or iodine; alternatively, $R^7$ and $R^9$, or $R^7$ and $R^{10}$ can come together to form a pi bond; and X is O, S, $SO_2$ or $CH_2$.

In an twelfth principal embodiment, the invention provides a compound of Formula XVIII, or a pharmaceutically acceptable salt or prodrug thereof:

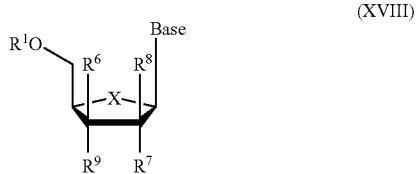

(XVIII)

wherein:

Base is a purine or pyrimidine base as defined herein;

$R^1$ and $R^2$ independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, lower alkylamino or di(lower-alkyl)amino;

$R^8$ is H, alkyl (including lower alkyl), chlorine, bromine or iodine;

alternatively, $R^7$ and $R^9$, or $R^8$ and $R^9$ can come together to form a pi bond;

X is O, S, $SO_2$ or $CH_2$.

The β-D- and β-L-nucleosides of this invention may inhibit HCV polymerase activity. Nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one embodiment the efficacy of the anti-HCV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 25, 15, 10, 5, or 1 micromolar.

In another embodiment, the active compound can be administered in combination or alternation with another anti-HCV agent. In combination therapy, an effective dosage of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include:

(1) an interferon and/or ribavirin (Battaglia, A. M. et al., *Ann. Pharmacother.* 34:487–494, 2000); Berenguer, M. et al. *Antivir. Ther.* 3(Suppl. 3):125–136, 1998);

(2) Substrate-based NS3 protease inhibitors (Attwood et al., *Antiviral peptide derivatives*, PCT WO 98/22496, 1998; Attwood et al., *Antiviral Chemistry and Chemotherapy* 10.259–273, 1999; Attwood et al., *Preparation and use of amino acid derivatives as anti-viral agents*, German Patent Publication DE 19914474; Tung et al. *Inhibitors of serine proteases, particularly hepatitis C virus NS3 protease*, PCT WO 98/17679), including alphaketoamides and hydrazinoureas, and inhibitors that terminate in an electrophile such as a boronic acid or phosphonate. Llinas-Brunet et al, *Hepatitis C inhibitor peptide analogues*, PCT WO 99/07734.

(3) Non-substrate-based inhibitors such as 2,4,6-trihydroxy-3-nitro-benzamide derivatives (Sudo K. et al., *Biochemical and Biophysical Research Communications*, 238: 643–647, 1997; Sudo K. et al. *Antiviral Chemistry and Chemotherapy* 9:186, 1998), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., *Antiviral Research* 32:9–18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. *J. EBS Letters* 421:217–220; Takeshita N. et al. *Analytical Biochemistry* 247:242–246, 1997;

(6) A phenan-threnequinone possessing activity against HCV protease in a SDS-PAGE and autoradiography assay isolated from the fermentation culture broth of *Streptomyces* sp., Sch 68631 (Chu M. et al., *Tetrahedron Letters* 37:7229–7232, 1996), and Sch 351633, isolated from the fungus *Penicillium griscofuluum*, which demonstrates activity in a scintillation proximity assay (Chu M. et al., *Bioorganic and Medicinal Chemistry Letters* 9:1949–1952);

(7) Selective NS3 inhibitors based on the macromolecule elgin c, isolated from leech (Qasim M. A. et al., *Biochemistry* 36:1598–1607, 1997);

(8) HCV helicase inhibitors (Diana G. D. et al., *Compounds, compositions and methods for treatment of hepatitis C*, U.S. Pat. No. 5,633,358; Diana G. D. et al., *Piperidine derivatives, pharmaceutical compositions thereof and their use in the treatment of hepatitis C*, PCT WO 97/36554);

(9) HCV polymerase inhibitors such as nucleotide analogues, gliotoxin (Ferrari R. et al. *Journal of Virology* 73:1649–1654, 1999), and the natural product cerulenin (Lohmann V. et al., *Virology* 249:108–118, 1998);

(10) Antisense phosphorothioate oligodeoxynucleotides (S-ODN) complementary to sequence stretches in the 5' non-coding region (NCR) of the HCV (Alt M. et al., *Hepatology* 22:707–717, 1995), or nucleotides 326–348 comprising the 3' end of the NCR and nucleotides 371–388 located in the core coding region of the IICV RNA (Alt M. et al., *Archives of Virology* 142:589–599, 1997; Galderisi U. et al., *Journal of Cellular Physiology* 181:251–257, 1999);

(11) Inhibitors of IRES-dependent translation (Ikeda N et al., *Agent for the prevention and treatment of hepatitis C*, Japanese Patent Publication JP-08268890; Kai Y. et al. *Prevention and treatment of viral diseases*, Japanese Patent Publication JP-10101591);

(12) Nuclease-resistant ribozymes (Maccjak D. J. et al., *Hepatology* 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

BRIEF DESCRIPTION OF THE FIGURES

FIG. 2 is a line graph of the pharmacokinetics (plasma concentrations) of β-D-2'-CH$_3$-riboG administered to six Cynomolgus Monkeys over time after administration.

DETAILED DESCRIPTION OF THE INVENTION

Figure 1:
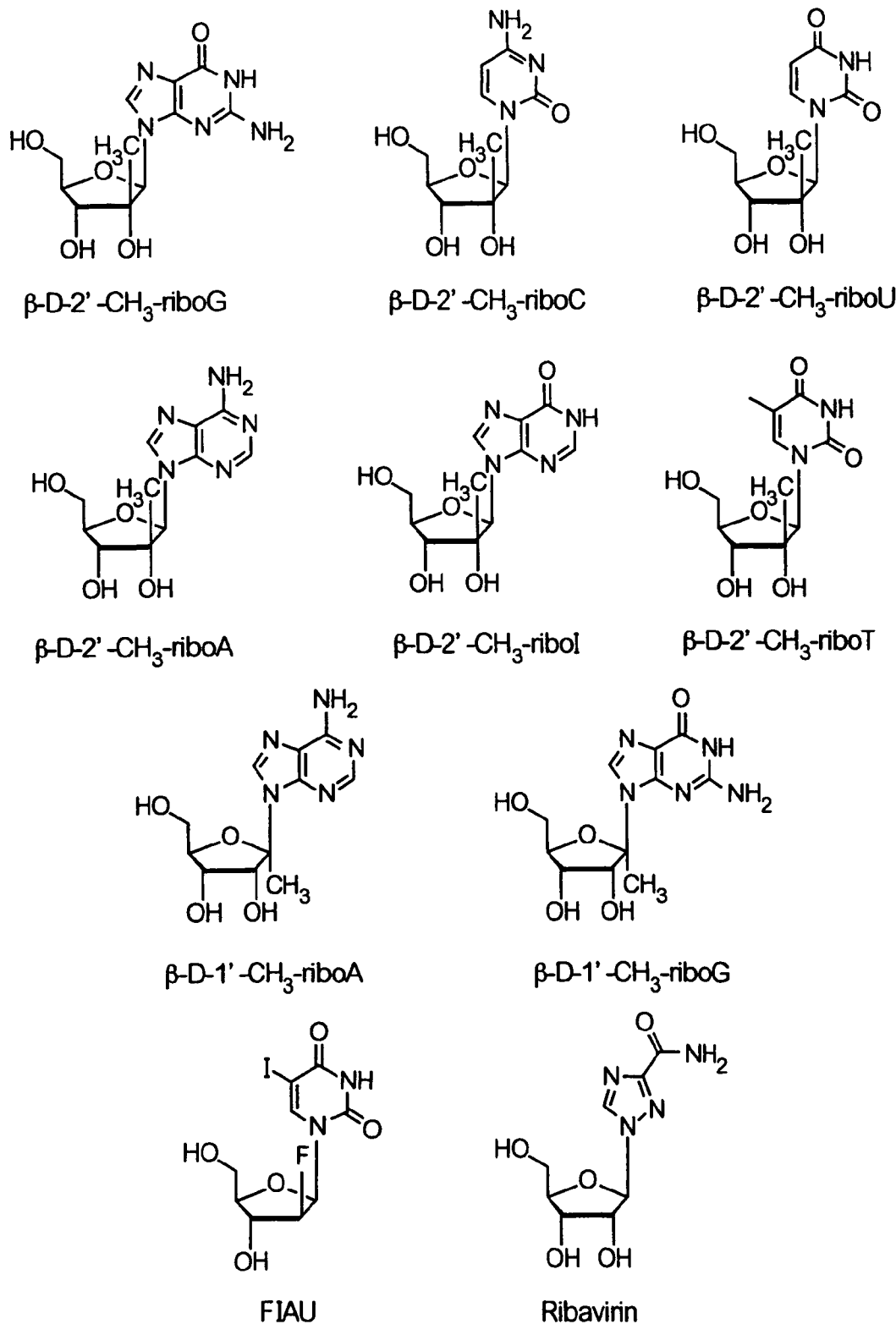
FIG. 1 provides the structure of various non-limiting examples of nucleosides of the present invention, as well as other known nucleosides, FIAU and Ribavirin, which are used as comparative examples in the text.

The invention as disclosed herein is a compound, method and composition for the treatment of hepatitis C in humans or other host animals, that includes administering an effective HCV treatment amount of a β-D- or β-L-nucleoside as described herein or a pharmaceutically acceptable salt or prodrug thereof, optionally in a pharmaceutically acceptable carrier. The compounds of this invention either possess antiviral (i.e., anti-HCV) activity, or are metabolized to a compound that exhibits such activity.

In summary, the present invention includes the following features:

(a) β-D- and β-L-nucleosides, as described herein, and pharmaceutically acceptable salts and prodrugs thereof;

(b) β-D- and β-L-nucleosides as described herein, and pharmaceutically acceptable salts and prodrugs thereof for use in the treatment or prophylaxis of an HCV infection, especially in individuals diagnosed as having an HCV infection or being at risk for becoming infected by HCV;

(c) use of these β-D- and β-L-nucleosides, and pharmaceutically acceptable salts and prodrugs thereof in the manufacture of a medicament for treatment of an HCV infection;

(d) pharmaceutical formulations comprising the β-D- or β-L-nucleosides or pharmaceutically acceptable salts or prodrugs thereof together with a pharmaceutically acceptable carrier or diluent;

(e) β-D- and β-L-nucleosides as described herein substantially in the absence of enantiomers of the described nucleoside, or substantially isolated from other chemical entities;

(f) processes for the preparation of β-D- and β-L-nucleosides, as described in more detail below; and (g) processes for the preparation of β-D- and β-L-nucleosides substantially in the absence of enantiomers of the described nucleoside, or substantially isolated from other chemical entities.

I. Active Compound, and Physiologically Acceptable Salts and Prodrugs Thereof

In a first principal embodiment, a compound of Formula I, or a pharmaceutically acceptable salt or prodrug thereof, is provided:

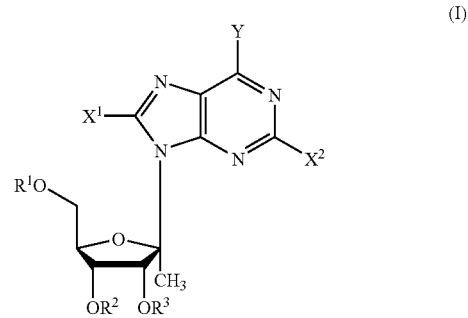

wherein:

R$^1$, R$^2$ and R$^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R$^1$, R$^2$ or R$^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4R^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula I, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a second principal embodiment, a compound of Formula II, or a pharmaceutically acceptable salt or prodrug thereof, is provided:

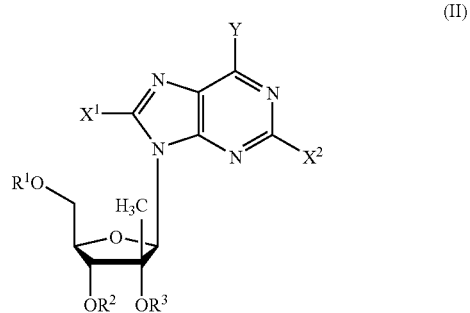

(II)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula II, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a third principal embodiment, a compound of Formula III, or a pharmaceutically acceptable salt or prodrug thereof, is provided:

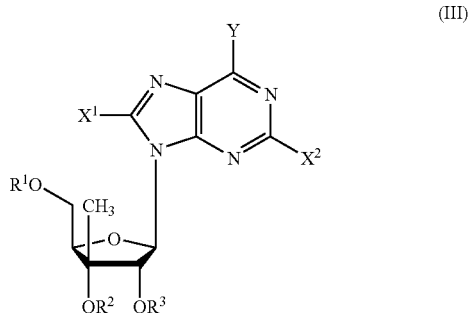

(III)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula III, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a fourth principal embodiment, a compound of Formula IV, or a pharmaceutically acceptable salt or prodrug thereof, is provided:

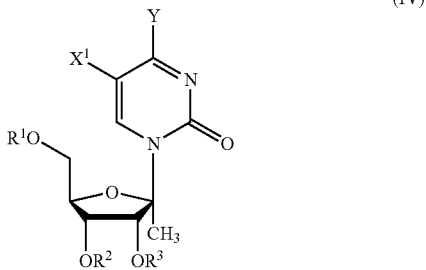

(IV)

wherein:
- $R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;
- Y is hydrogen, bromo, chloro, fluoro, iodo, $OR^4$, $NR^4R^5$ or $SR^4$;
- $X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and
- $R^4$ and $R^5$ are independently hydrogen, acyl (including lower acyl), or alkyl (including but not limited to methyl, ethyl, propyl and cyclopropyl).

In a preferred subembodiment, a compound of Formula IV, or a pharmaceutically acceptable salt or prodrug thereof, is provided wherein:
- $R^1$, $R^2$ and $R^3$ are independently H or phosphate (preferably H);
- $X^1$ is H or $CH_3$; and
- Y is hydrogen, bromo, chloro, fluoro, iodo, $NH_2$ or OH.

In a fifth principal embodiment, a compound of Formula V, or a pharmaceutically acceptable salt or prodrug thereof, is provided:

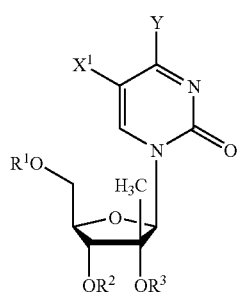

(V)

wherein:
- $R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and
- Y is hydrogen, bromo, chloro, fluoro, iodo, $OR^4$, $NR^4R^5$ or $SR^4$;
- $X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and
- $R^4$ and $R^5$ are independently hydrogen, acyl (including lower acyl), or alkyl (including but not limited to methyl, ethyl, propyl and cyclopropyl).

In a preferred subembodiment, a compound of Formula V, or a pharmaceutically acceptable salt or prodrug thereof, is provided wherein:
- $R^1$, $R^2$ and $R^3$ are independently H or phosphate (preferably H);
- $X^1$ is H or $CH_3$; and
- Y is hydrogen, bromo, chloro, fluoro, iodo, $NH_2$ or OH.

In a sixth principal embodiment, a compound of Formula VI, or a pharmaceutically acceptable salt or prodrug thereof, is provided:

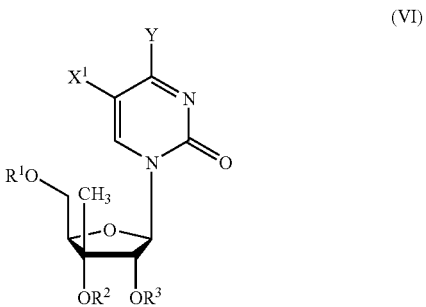

(VI)

wherein:
- $R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and
- Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula VI, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a seventh principal embodiment, a compound selected from Formulas VII, VIII and IX, or a pharmaceutically acceptable salt or prodrug thereof, is provided:

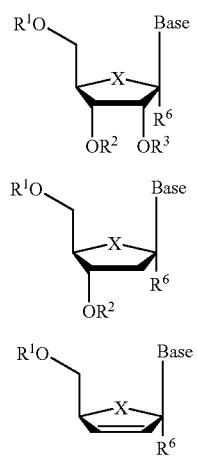

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$, or $CH_2$.

In a first preferred subembodiment, a compound of Formula VII, VIII or IX, or a pharmaceutically acceptable salt or prodrug thereof, is provided wherein:

Base is a purine or pyrimidine base as defined herein;

$R^1$, $R^2$ and $R^3$ are independently hydrogen or phosphate;

$R^6$ is alkyl; and

X is O, S, $SO_2$ or $CH_2$.

In a second preferred subembodiment, a compound of Formula VII, VIII or IX, or a pharmaceutically acceptable salt or prodrug thereof, is provided wherein:

Base is a purine or pyrimidine base as defined herein;

$R^1$, $R^2$ and $R^3$ are hydrogens;

$R^6$ is alkyl; and

X is O, S, $SO_2$ or $CH_2$.

In a third preferred subembodiment, a compound of Formula VII, VIII or IX, or a pharmaceutically acceptable salt or prodrug thereof, is provided wherein:

Base is a purine or pyrimidine base as defined herein;

$R^1$, $R^2$ and $R^3$ are independently hydrogen or phosphate;

$R^6$ is alkyl; and

X is O.

In a eighth principal embodiment, a compound of Formula X, XI or XII, or a pharmaceutically acceptable salt or prodrug thereof, is provided:

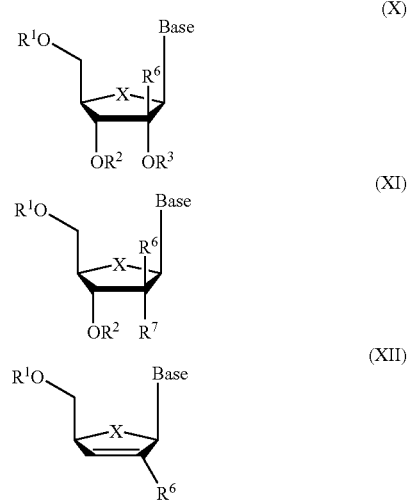

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, NO$_2$, NH$_2$, —NH(lower alkyl), —NH(acyl), —N(loweralkyl)$_2$, —N(acyl)$_2$; and X is O, S, SO$_2$ or CH$_2$.

In a first preferred subembodiment, a compound of Formula X, XI or XII, or a pharmaceutically acceptable salt or prodrug thereof, is provided wherein:

Base is a purine or pyrimidine base as defined herein;

R$^1$, R$^2$ and R$^3$ are independently hydrogen or phosphate;

R$^6$ is alkyl; and

X is O, S, SO$_2$ or CH$_2$.

In a second preferred subembodiment, a compound of Formula X, XI or XII, or a pharmaceutically acceptable salt or prodrug thereof, is provided wherein:

Base is a purine or pyrimidine base as defined herein;

R$^1$, R$^2$ and R$^3$ are hydrogens;

R$^6$ is alkyl; and

X is O, S, SO$_2$ or CH$_2$.

In a third preferred subembodiment, a compound of Formula X, XI or XII, or a pharmaceutically acceptable salt or prodrug thereof, is provided wherein:

Base is a purine or pyrimidine base as defined herein;

R$^1$, R$^2$ and R$^3$ are independently H or phosphate;

R$^6$ is alkyl; and

X is O.

In even more preferred subembodiments, a compound of Formula XI, or its pharmaceutically acceptable salt or prodrug, is provided:

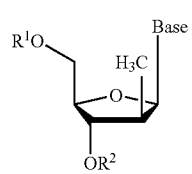

(XI)

wherein:

Base is a purine or pyrimidine base as defined herein; optionally substituted with an amine or cyclopropyl (e.g., 2-amino, 2,6-diamino or cyclopropyl guanosine); and R$^1$ and R$^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R$^1$ or R$^2$ is independently H or phosphate.

In a ninth principal embodiment a compound selected from Formula XIII, XIV or XV, or a pharmaceutically acceptable salt or prodrug thereof, is provided:

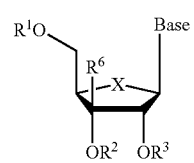

(XIII)

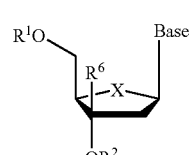

(XIV)

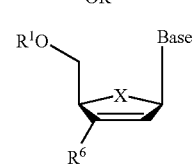

(XV)

wherein:

Base is a purine or pyrimidine base as defined herein;

R$^1$, R$^2$ and R$^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R$^1$, R$^2$ or R$^3$ is independently H or phosphate;

R$^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO$_2$, NH$_2$, —NH(lower alkyl), —NH(acyl), —N(lower alkyl)$_2$, —N(acyl)$_2$; and X is O, S, SO$_2$ or CH$_2$.

In a first preferred subembodiment, a compound of Formula XIII, XIV or XV, or a pharmaceutically acceptable salt or prodrug thereof, is provided wherein:

Base is a purine or pyrimidine base as defined herein;

R$^1$, R$^2$ and R$^3$ are independently hydrogen or phosphate;

R$^6$ is alkyl; and

X is O, S, SO$_2$ or CH$_2$.

In a second preferred subembodiment, a compound of Formula XIII, XIV or XV, or a pharmaceutically acceptable salt or prodrug thereof, is provided wherein:

Base is a purine or pyrimidine base as defined herein;

R$^1$, R$^2$ and R$^3$ are hydrogens;

R$^6$ is alkyl; and

X is O, S, SO$_2$ or CH$_2$.

In a third preferred subembodiment, a compound of Formula XIII, XIV or XV, or a pharmaceutically acceptable salt or prodrug thereof, is provided wherein:
Base is a purine or pyrimidine base as defined herein;
$R^1$, $R^2$ and $R^3$ are independently hydrogen or phosphate;
$R^6$ is alkyl; and
X is O.

In a tenth principal embodiment the invention provides a compound of Formula XVI, or a pharmaceutically acceptable salt or prodrug thereof:

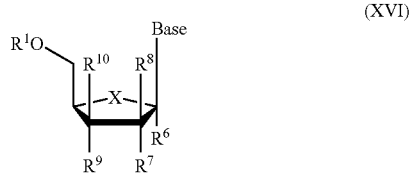

(XVI)

wherein:
Base is a purine or pyrimidine base as defined herein;
$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ and $R^2$ are independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;
$R^8$ and $R^{10}$ are independently H, alkyl (including lower alkyl), chlorine, bromine or iodine; alternatively, $R^7$ and $R^9$, $R^7$ and $R^{10}$, $R^8$ and $R^9$, or $R^8$ and $R^{10}$ can come together to form a pi bond; and
X is O, S, $SO_2$ or $CH_2$.

In a first preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine, or iodine; and (6) X is O, S, $SO_2$ or $CH_2$.

In a second preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ and $R^{10}$ are independently H, alkyl (including lower alkyl), chlorine, bromine, or iodine; and (6) X is O, S, $SO_2$ or $CH_2$.

In a third preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are H; and (6) X is O, S, $SO_2$ or $CH_2$.

In a fourth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are independently H, alkyl (including lower alkyl), chlorine, bromine, or iodine; and (6) X is O.

In a fifth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^1$; (5) $R^8$ and $R^{10}$ are independently H, alkyl (including lower alkyl), chlorine, bromine or iodine; and (6) X is O, S, $SO_2$ or $CH_2$.

In a sixth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are H; and (6) X is O, S, $SO_2$, or $CH_2$.

In a seventh preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine or iodine; and (6) X is O.

In a eighth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including. lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a ninth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are independently H, alkyl (including lower alkyl), chlorine, bromine or iodine; and (6) X is O.

In a tenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H. or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are hydrogen; and (6) X is O.

In an eleventh preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, NO₂, amino, loweralkylamino or di(loweralkyl)amino; (4) R⁷ and R⁹ are independently OR²; (5) R⁸ and R¹⁰ are hydrogen; and (6) X is O, S, SO₂ or CH₂.

In a twelfth preferred subembodiment, a compound of Formula XVI, or its pharmaceutically acceptable salt or prodrug, is provided in which: (1) Base is a purine or pyrimidine base as defined herein; (2) R¹ is independently H or phosphate; (3) R⁶ is alkyl; (4) R⁷ and R⁹ are independently OR²; (5) R⁸ and R¹⁰ are hydrogen; and (6) X is O, S, SO₂, or CH₂.

In a thirteenth preferred subembodiment, a compound of Formula XVI, or its pharmaceutically acceptable salt or prodrug, is provided in which: (1) Base is a purine or pyrimidine base as defined herein; (2) R¹ is independently H or phosphate; (3) R⁶ is alkyl; (4) R⁷ and R⁹ are independently OR²; (5) R⁸ and R¹⁰ are independently H, alkyl (including lower alkyl), chlorine, bromine, or iodine; and (6) X is O.

In a fourteenth preferred subembodiment, a compound of Formula XVI, or its pharmaceutically acceptable salt or prodrug, is provided in which: (1) Base is a purine or pyrimidine base as defined herein; (2) R¹ is independently H or phosphate; (3) R⁶ is alkyl; (4) R⁷ and R⁹ are independently OR², alkyl (including lower alkyl), alkenyl, alkynyl, Br-vinyl, O-alkenyl, chlorine, bromine, iodine, NO₂, amino, loweralkylamino or di(loweralkyl)amino; (5) R⁸ and R¹⁰ are hydrogen; and (6) X is O.

In even more preferred subembodiments, a compound of Formula XVI, or its pharmaceutically acceptable salt or prodrug, is provided in which:

(1) Base is adenine; (2) R¹ is hydrogen; (3) R⁶ is methyl; (4) R⁷ and R⁹ are hydroxyl; (5) R⁸ and R¹⁰ are hydrogen; and (6) X is O;

(1) Base is guanine; (2) R¹ is hydrogen; (3) R⁶ is methyl; (4) R⁷ and R⁹ are hydroxyl; (5) R⁸ and R¹⁰ are hydrogen; and (6) X is O;

(1) Base is cytosine; (2) R¹ is hydrogen; (3) R⁶ is methyl; (4) R⁷ and R⁹ are hydroxyl; (5) R⁸ and R¹⁰ are hydrogen; and (6) X is O;

(1) Base is thymine; (2) R¹ is hydrogen; (3) R⁶ is methyl; (4) R⁷ and R⁹ are hydroxyl; (5) R⁸ and R¹⁰ are hydrogen; and (6) X is O;

(1) Base is uracil; (2) R¹ is hydrogen; (3) R⁶ is methyl; (4) R⁷ and R⁹ are hydroxyl; (5) R⁸ and R¹⁰ are hydrogen; and (6) X is O;

(1) Base is adenine; (2) R¹ is phosphate; (3) R⁶ is methyl; (4) R⁷ and R⁹ are hydroxyl; (5) R⁸ and R¹⁰ are hydrogen; and (6) X is O;

(1) Base is adenine; (2) R¹ is hydrogen; (3) R⁶ is ethyl; (4) R⁷ and R⁹ are hydroxyl; (5) R⁸ and R¹⁰ are hydrogen; and (6) X is O;

(1) Base is adenine; (2) R¹ is hydrogen; (3) R⁶ is propyl; (4) R⁷ and R⁹ are hydroxyl; (5) R⁸ and R¹⁰ are hydrogen; and (6) X is O;

(1) Base is adenine; (2) R¹ is hydrogen; (3) R⁶ is butyl; (4) R⁷ and R⁹ are hydroxyl; (5) R⁸ and R¹⁰ are hydrogen; and (6) X is O;

(1) Base is adenine; (2) R¹ is hydrogen; (3) R⁶ is methyl; (4) R⁷ is hydrogen and R⁹ is hydroxyl; (5) R⁸ and R¹⁰ are hydrogen; and (6) X is O;

(1) Base is adenine; (2) R¹ is hydrogen; (3) R⁶ is methyl; (4) R⁷ and R⁹ are hydroxyl; (5) R⁸ and R¹⁰ are hydrogen; and (6) X is S;

(1) Base is adenine; (2) R¹ is hydrogen; (3) R⁶ is methyl; (4) R⁷ and R⁹ are hydroxyl; (5) R⁸ and R¹⁰ are hydrogen; and (6) X is SO₂;

(1) Base is adenine; (2) R¹ is hydrogen; (3) R⁶ is methyl; (4) R⁷ and R⁹ are hydroxyl; (5) R⁸ and R¹⁰ are hydrogen; and (6) X is CH₂;

In a eleventh principal embodiment the invention provides a compound of Formula XVII, or a pharmaceutically acceptable salt or prodrug thereof:

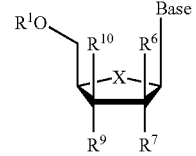

wherein:

Base is a purine or pyrimidine base as defined herein;

R¹ is H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹ is independently H or phosphate;

R⁶ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, —N(acyl)₂;

R⁷ and R⁹ are independently hydrogen, OR², hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, NO₂, NH₂, —NH(lower alkyl), —NH(acyl), —N(lower alkyl)₂, —N(acyl)₂;

R¹⁰ is H, alkyl (including lower alkyl), chlorine, bromine, or iodine; alternatively, R⁷ and R⁹, or R⁷ and R¹⁰ can come together to form a pi bond; and X is O, S, SO₂ or CH₂.

In a first preferred subembodiment, a compound of Formula XVII, or its pharmaceutically acceptable salt or prodrug, is provided in which: (1) Base is a purine or pyrimidine base as defined herein; (2) R¹ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹ is independently H or phosphate; (3) R⁶ is alkyl (including lower alkyl), alkenyl, alkynyl, Br-vinyl, hydroxy, O-alkyl, O-alkenyl, chloro, bromo, fluoro, iodo, NO₂, amino, loweralkylamino, or di(loweralkyl)amino; (4) R⁷ and R⁹ are independently hydrogen, OR², alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H; and (6) X is O, S, $SO_2$, or $CH_2$.

In a second preferred subembodiment, a compound of Formula XVII, or its pharmaceutically acceptable salt or prodrug, is provided in which: (1) Base is a purine or pyrimidine base as defined herein; (2) $R^{10}$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H, alkyl (including lower alkyl), chlorine, bromine, or iodine; and (6) X is O, S, $SO_2$ or $CH_2$.

In a third preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H, alkyl (including lower alkyl), chlorine, bromine or iodine; and (6) X is O.

In a fourth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H; and (6) X is O, S, $SO_2$ or $CH_2$.

In a fifth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H, alkyl (including lower alkyl), chlorine, bromine or iodine; and (6) X is O.

In a sixth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^{10}$ is H; and (6) X is O.

In a seventh preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^{10}$ is H; and (6) X is O.

In an eighth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H, alkyl (including lower alkyl), chlorine, bromine or iodine; and (6) X is O, S, $SO_2$, or $CH_2$.

In a ninth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^{10}$ is H; and (6) X is O, S, $SO_2$, or $CH_2$.

In a tenth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^{10}$ is H; and (6) X is O, S, $SO_2$, or $CH_2$.

In even more preferred subembodiments, a compound of Formula XVII, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^{10}$ is hydrogen; and (6) X is O;

(1) Base is guanine; (2) $R^1$ is hydrogen; (3) $R^6$ is methyl; (4) $R^7$ and $R^9$ are hydroxyl; (5) $R^{10}$ is hydrogen; and (6) X is O;

(1) Base is cytosine; (2) $R^1$ is hydrogen; (3) $R^6$ is methyl; (4) $R^7$ and $R^9$ are hydroxyl; (5) $R^{10}$ is hydrogen; and (6) X is O;

(1) Base is thymine; (2) $R^1$ is hydrogen; (3) $R^6$ is methyl; (4) $R^7$ and $R^9$ are hydroxyl; (5) $R^{10}$ is hydrogen; and (6) X is O;

(1) Base is uracil; (2) $R^1$ is hydrogen; (3) $R^6$ is methyl; (4) $R^7$ and $R^9$ are hydroxyl; (5) $R^{10}$ is hydrogen; and (6) X is O;

(1) Base is adenine; (2) $R^1$ is phosphate; (3) $R^6$ is methyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is ethyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is propyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is butyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is methyl; (4) $R^7$ and $R^9$ are hydroxyl; (5) $R^{10}$ is hydrogen; and (6) X is S;

(1) Base is adenine; (2) $R^1$ is hydrogen; (3) $R^6$ is methyl; (4) $R^7$ and $R^9$ are hydroxyl; (5) $R^{10}$ is hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^{10}$ is hydrogen; and (6) X is $CH_2$.

In an twelfth principal embodiment the invention provides a compound of Formula XVIII, or a pharmaceutically acceptable salt or prodrug thereof:

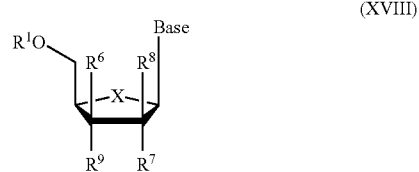

(XVIII)

wherein:
Base is a purine or pyrimidine base as defined herein;
$R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;
$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, lower alkylamino, or di(loweralkyl)amino;
$R^8$ is H, alkyl (including lower alkyl), chlorine, bromine or iodine; alternatively, $R^7$ and $R^9$, or $R^8$ and $R^9$ can come together to form a pi bond;
X is O, S, $SO_2$ or $CH_2$.

In a first preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ is H, alkyl (including lower alkyl), chlorine, bromine or iodine; and (6) X is O, S, $SO_2$ or $CH_2$.

In a second preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ is H, alkyl (including lower alkyl), chlorine, bromine, or iodine; and (6) X is O, S, $SO_2$ or $CH_2$.

In a third preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(lower-alkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H; and (6) X is O, S, $SO_2$ or $CH_2$.

In a fourth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H, alkyl (including lower alkyl), chlorine, bromine, or iodine; and (6) X is O.

In a fifth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ is H; and (6) X is O, S, $SO_2$, or $CH_2$.

In a sixth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)am no; (4) $R^7$ and $R^9$ are independently $OR^2$; (5) $R^8$ is H, alkyl (including lower alkyl), chlorine, bromine, or iodine; and (6) X is O.

In a seventh preferred subembodiment, a compound of Formula XVIII, or its pharmaceutically acceptable salt or prodrug is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H; and (6) X is O.

In an eighth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ is H; and (6) X is O, S, $SO_2$ or $CH_2$.

In a ninth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) R is H; and (6) X is O, S, $SO_2$, or $CH_2$.

In a tenth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ is H; and (6) X is O.

In even more preferred subembodiments, a compound of Formula XVIII, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^8$ is hydrogen; and (6) X is O;

(1) Base is guanine; (2) $R^1$ is hydrogen; (3) $R^6$ is methyl; (4) $R^7$ and $R^9$ are hydroxyl; (5) $R^8$ is hydrogen; and (6) X is O;

(1) Base is cytosine; (2) $R^1$ is hydrogen; (3) $R^6$ is methyl; (4) $R^7$ and $R^9$ are hydroxyl; (5) $R^8$ is hydrogen; and (6) X is O;

(1) Base is thymine; (2) $R^1$ is hydrogen; (3) $R^6$ is methyl; (4) $R^7$ and $R^9$ are hydroxyl; (5) $R^8$ is hydrogen; and (6) X is O;

(1) Base is uracil; (2) $R^1$ is hydrogen; (3) $R^6$ is methyl; (4) $R^7$ and $R^9$ are hydroxyl; (5) $R^8$ is hydrogen; and (6) X is O;

(1) Base is adenine; (2) $R^1$ is phosphate; (3) $R^6$ is methyl; (4) $R^7$ and $R^9$ are hydroxyl; (5) $R^8$ is hydrogen; and (6) X is O;

(1) Base is adenine; (2) $R^1$ is hydrogen; (3) $R^6$ is ethyl; (4) $R^7$ and $R^9$ are hydroxyl; (5) $R^8$ is hydrogen; and (6) X is O;

(1) Base is adenine; (2) $R^1$ is hydrogen; (3) $R^6$ is propyl; (4) $R^7$ and $R^9$ are hydroxyl; (5) $R^8$ is hydrogen; and (6) X is O;

(1) Base is adenine; (2) $R^1$ is hydrogen; (3) $R^6$ is butyl; (4) $R^7$ and $R^9$ are hydroxyl; (5) $R^8$ is hydrogen; and (6) X is O;

(1) Base is adenine; (2) $R^1$ is hydrogen; (3) $R^6$ is methyl; (4) $R^7$ and $R^9$ are hydroxyl; (5) $R^8$ is hydrogen; and (6) X is S;

(1) Base is adenine; (2) $R^1$ is hydrogen; (3) $R^6$ is methyl; (4) $R^7$ and $R^9$ are hydroxyl; (5) $R^8$ is hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^8$ is hydrogen; and (6) X is $CH_2$.

The β-D- and β-L-nucleosides of this invention may inhibit HCV polymerase activity. Nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one embodiment the efficacy of the anti-HCV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or 10 micromolar, when measured according to the polymerase assay described in Ferrari et al., *Jnl. of Vir.,* 73:1649–1654, 1999; Ishii et al., *Hepatology,* 29:1227–1235,1999; Lohmann et al., *Jnl. of Bio. Chem.,* 274:10807–10815, 1999; or Yamashita et al, *Jnl. of Bio. Chem.,* 273:15479–15486, 1998.

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound that has been alkylated or acylated at the 5'-position or on the purine or pyrimidine base (a type of "pharmaceutically acceptable prodrug"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

II. Definitions

The term alkyl, as used herein, unless otherwise specified, refers to a saturated straight, branched, or cyclic, primary, secondary, or tertiary hydrocarbon of typically $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alcylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is a lower alkyl.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "independently" is used herein to indicate that the variable which is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term host, as used herein, refers to an unicellular or multicellular organism in which the virus can replicate, including cell lines and animals, and preferably a human. Alternatively, the host can be carrying a part of the hepatitis C viral genome, whose replication or function can be altered by the compounds of the present invention. The term host specifically refers to infected cells, cells transfected with all or part of the HCV genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against HCV, or are metabolized to a compound that exhibits such activity.

III. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3, -deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

IV. Combination and Alternation Therapy

It has been recognized that drug-resistant variants of HCV can emerge after prolonged treatment with an antiviral agent. Drug resistance most typically occurs by mutation of a gene that encodes for an enzyme used in viral replication. The efficacy of a drug against HCV infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Nonlimiting examples of antiviral agents that can be used in combination with the compounds disclosed herein include:

(1) an interferon and/or ribavirin (Battaglia, A. M. et al., *Ann. Pharmacother.* 34:487–494, 2000); Berenguer, M. et al. *Antivir. Ther.* 3(Suppl. 3):125–136, 1998);

(2) Substrate-based NS3 protease inhibitors (Attwood et al., *Antiviral peptide derivatives*, PCT WO 98/22496, 1998; Attwood et al., *Antiviral Chemistry and Chemotherapy* 10.259–273, 1999; Attwood et al., *Preparation and use of amino acid derivatives as anti-viral agents*, German Patent Publication DE 19914474; Tung et al. *Inhibitors of serine proteases, particularly hepatitis C virus NS3 protease*, PCT WO 98/17679), including alphaketoamides and hydrazinoureas, and inhibitors that terminate in an electrophile such as a boronic acid or phosphonate. Llinas-Brunet et al, *Hepatitis C inhibitor peptide analogues*, PCT WO 99/07734.

(3) Non-substrate-based inhibitors such as 2,4,6-trihydroxy-3-nitro-benzamide derivatives (Sudo K. et al., *Biochemical and Biophysical Research Communications*, 238: 643–647, 1997; Sudo K. et al. *Antiviral Chemistry and Chemotherapy* 9:186, 1998), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., *Antiviral Research* 32:9–18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. *J. EBS Letters* 421:217–220; Takeshita N. et al. *Analytical Biochemistry* 247:242–246, 1997;

(6) A phenan-threnequmnone possessing activity against HCV protease in a SDS-PAGE and autoradiography assay isolated from the fermentation culture broth of *Streptomyces* sp., Sch 68631 (Chu M. et al., *Tetrahedron Letters* 37:7229–7232, 1996), and Sch 351633, isolated from the fungus *Penicillium griscofuluum*, which demonstrates activity in a scintillation proximity assay (Chu M. et al., *Bioorganic and Medicinal Chemistry Letters* 9:1949–1952);

(7) Selective NS3 inhibitors based on the macromolecule elgin c, isolated from leech (Qasim M. A. et al., *Biochemistry* 36:1598–1607, 1997);

(8) HCV helicase inhibitors (Diana G. D. et al., *Compounds, compositions and methods for treatment of hepatitis C*, U.S. Pat. No. 5,633,358; Diana G. D. et al., *Piperidine derivatives, pharmaceutical compositions thereof and their use in the treatment of hepatitis C*, PCT WO 97/36554);

(9) HCV polymerase inhibitors such as nucleotide analogues, gliotoxin (Ferrari R. et al. *Journal of Virology* 73:1649–1654, 1999), and the natural product cerulenin (Lohmann. V. et al., *Virology* 249:108–118, 1998);

(10) Antisense phosphorothioate oligodeoxynucleotides (S-ODN) complementary to sequence stretches in the 5'noncoding region (NCR) of the HCV (Alt M. et al., *Hepatology* 22:707–717, 1995), or nucleotides 326–348 comprising the 3' end of the NCR and nucleotides 371–388 located in the core coding region of the IICV RNA (Alt M. et al., *Archives of Virology* 142:589–599, 1997; Galderisi U. et al., *Journal of Cellular Physiology* 181:251–257, 1999);

(11) Inhibitors of IRES-dependent translation (Ikeda N et al., *Agent for the prevention and treatment of hepatitis C*, Japanese Patent Publication JP-08268890; Kai Y. et al. *Prevention and treatment of viral diseases*, Japanese Patent Publication JP-10101591);

(12) Nuclease-resistant ribozymes. (Maccjak D. J. et al., *Hepatology* 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

V. Pharmaceutical Compositions

Hosts, including humans, infected with HCV, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for HCV will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 µM, preferably about 1.0 to 10 µM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside. compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VI. Processes for the Preparation of Active Compounds

The nucleosides of the present invention can be synthesized by any means known in the art. In particular, the synthesis of the present nucleosides can be achieved by either alkylating the appropriately modified sugar, followed by glycosylation or glycosylation followed by alkylation of the nucleoside. The following non-limiting embodiments illustrate some general methodology to obtain the nucleosides of the present invention.

A. General Synthesis of 1'-C-Branched Nucleosides

1'-C-Branched ribonucleosides of the following structure:

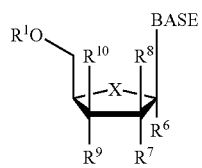

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ and $R^{10}$ are independently H, alkyl (including lower alkyl), chlorine, bromine or iodine;

alternatively, $R^7$ and $R^9$, $R^7$ and $R^{10}$, $R^8$ and $R^9$, or $R^8$ and $R^{10}$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is an alkyl, chloro-, bromo-, fluoro-, or iodo-alkyl (i.e. $CF_3$), alkenyl, or alkynyl (i.e. allyl); and X is O, S, $SO_2$ or $CH_2$ can be prepared by one of the following general methods.

1) Modification from the Lactone

The key starting material for this process is an appropriately substituted lactone. The lactone can be purchased or can be prepared by any known means including standard epimerization, substitution and cyclization techniques. The lactone can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991. The protected lactone can then be coupled with a suitable coupling agent, such as an organometallic carbon nucleophile, such as a Grignard reagent, an organolithium, lithium dialkyl copper or R$_6$—SiMe$_3$ in TBAF with the appropriate non-protic solvent at a suitable temperature, to give the 1'-alkylated sugar.

The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 1'-C-branched ribonucleoside is desired. The synthesis of a ribonucleoside is shown in Scheme 1. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

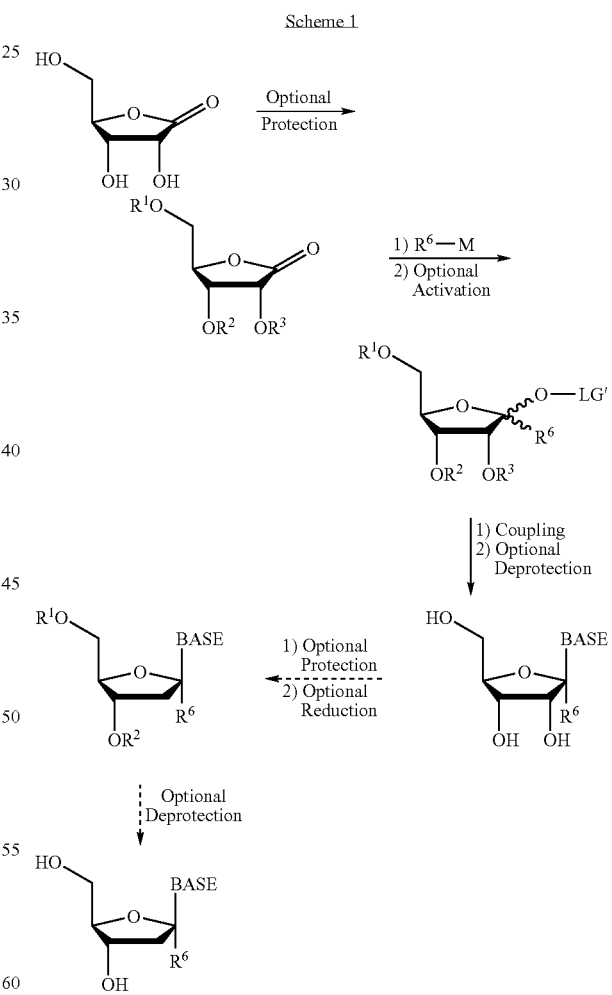

Scheme 1

2. Alternative Method for the Preparation of 1'C-Branched Nucleosides

The key starting material for this process is an appropriately substituted hexose. The hexose can be purchased or can be prepared by any known means including standard epimerization, such as alkaline treatment, substitution and coupling techniques. The hexose can be selectively protected to give the appropriate hexa-furanose, as taught by Townsend *Chemistry of Nucleosides and Nucleotides*, Plenum Press, 1994.

The 1'-hydroxyl can be optionally activated to a suitable leaving group such as an acyl group or a chloro, bromo, fluoro, iodo via acylation or halogenation, respectively. The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

The 1'-$CH_2$—OH, if protected, can be selectively deprotected by methods well known in the art. The resultant primary hydroxyl can be functionalized to yield various C-branched nucleosides. For example, the primary hydroxyl can be reduced to give the methyl, using a suitable reducing agent. Alternatively, the hydroxyl can be activated prior to reduction to facilitate the reaction; i.e. via the Barton reduction. In an alternate embodiment, the primary hydroxyl can be oxidized to the aldehyde, then coupled with a carbon nucleophile, such as a Grignard reagent, an organolithium, lithium dialkylcopper or $R^6$—$SiMe_3$ in TBAF with the appropriate non-protic solvent at a suitable temperature.

In a particular embodiment, the 1'-C-branched ribonucleoside is desired. The synthesis of a ribonucleoside is shown in Scheme 2. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In addition, the L-enantiomers corresponding to the compounds of the invention can be prepared following the same general methods (1 or 2), beginning with the corresponding L-sugar or nucleoside L-enantiomer as starting material.

B. General Synthesis of 2'-C-Branched Nucleosides

2'-C-Branched ribonucleosides of the following structure:

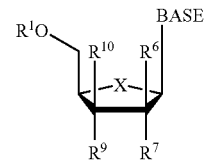

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^{10}$ is H, alkyl (including lower alkyl), chlorine, bromine or iodine;

alternatively, $R^7$ and $R^9$, or $R^7$ and $R^{10}$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

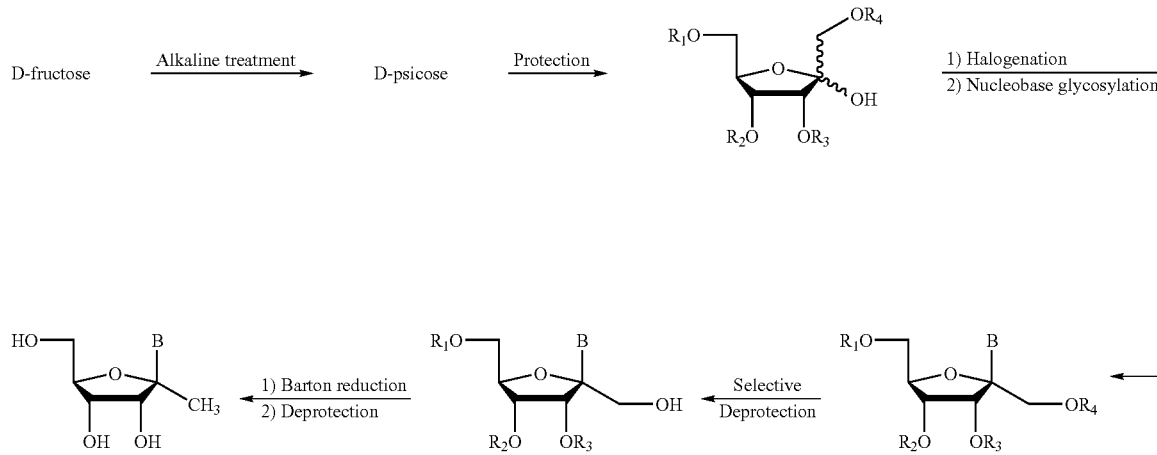

Scheme 2

$R^6$ is an alkyl, chloro-, bromo-, fluoro-, iodo-alkyl (i.e. $CF_3$), alkenyl, or alkynyl (i.e. allyl); and X is O, S, $SO_2$ or $CH_2$ can be prepared by one of the following general methods.

1. Glycosylation of the Nucleobase with an Appropriately Modified Sugar

The key starting material for this process is an appropriately substituted sugar with a 2'-OH and 2'-H, with the appropriate leaving group (LG), for example an acyl group or a chloro, bromo, fluoro or iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as. taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 3. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 3

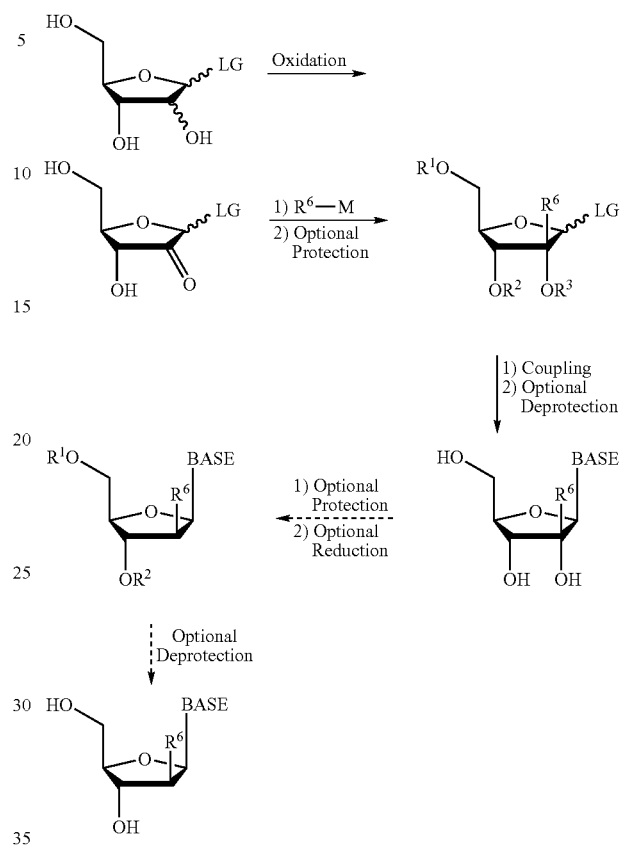

2. Modification of a Pre-Formed Nucleoside

The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf Verley reagent (aluminum t-butoxide with another ketone) and N-bromosuccinimide.

Subsequently, the nucleoside can be deprotected by methods well known to those skilled in the art, as taught by Greene-Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 4. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

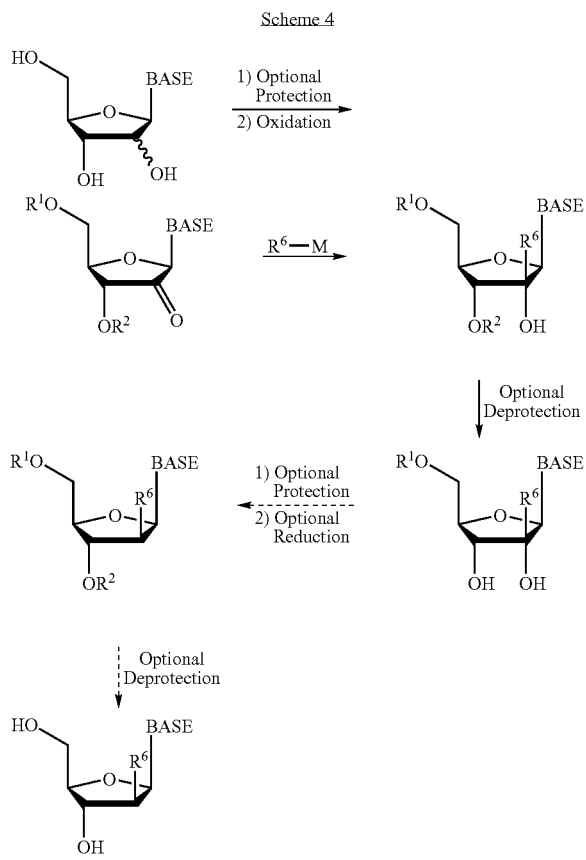

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

C. General Synthesis of 3'-C-Branched Nucleosides

3'-C-Branched ribonucleosides of the following structure:

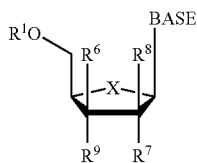

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ is H, alkyl (including lower alkyl), chlorine, bromine or iodine; alternatively, $R^7$ and $R^9$, or $R^8$ and $R^9$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is an alkyl, chloro-, fluoro-, bromo-, iodo-alkyl (i.e. $CF_3$), alkenyl, or alkynyl (i.e. allyl); and X is O, S, $SO_2$ or $CH_2$ can be prepared by one of the following general methods.

1. Glycosylation of the Nucleobase with an Appropriately Modified Sugar

The key starting material for this process is an appropriately substituted sugar with a 3'-OH and 3'-H, with the appropriate leaving group (LG), for example an acyl group or a chloro, bromo, fluoro, iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 3'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 3'-C-branched sugar. The 3'-C-branched sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 5. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

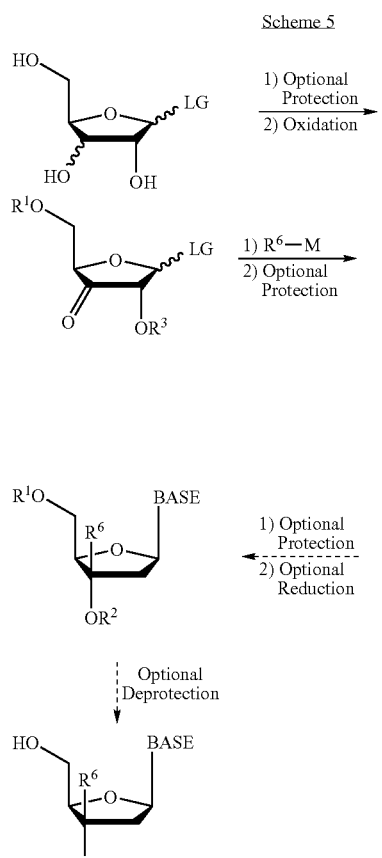

2. Modification of a Pre-Formed Nucleoside

The key starting material for this process is an appropriately substituted nucleoside with a 3'-OH and 3'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by Greene-Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 6. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

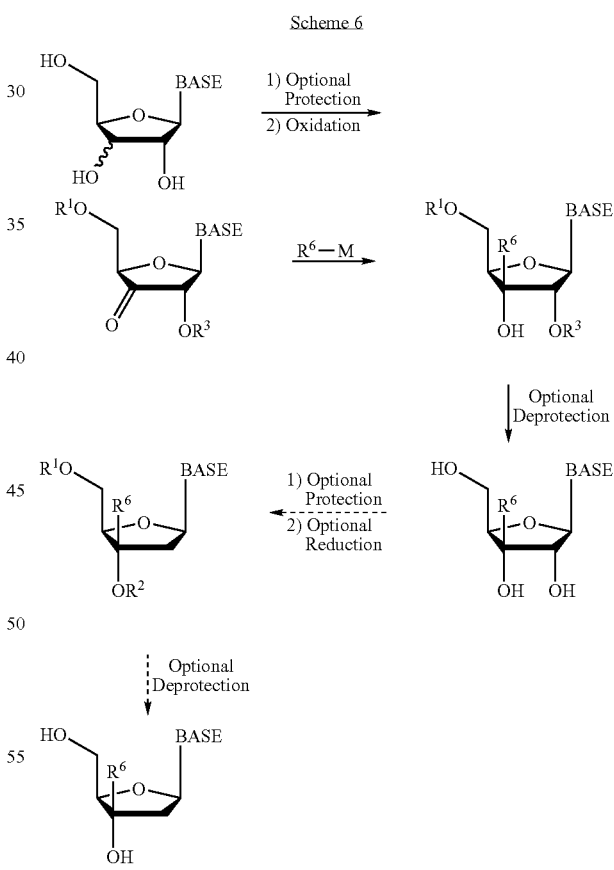

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

EXAMPLES

Example 1

Preparation of 1'-C-methylriboadenine via 6-amino-9-(1-deoxy-β-D-psicofuranosyl)purine As another alternative method of preparation, the title compound could also be prepared according to a published procedure (J. Farkas, and F. Sorm, "Nucleic acid components and their analogues. XCIV. Synthesis of 6-amino-9-(1-deoxy-β-D-psicofuranosyl)purine", *Collect. Czech. Chem. Commun.* 1967, 32, 2663–2667. J. Farkas", *Collect. Czech. Chem. Commun.* 1966, 31, 1535) (Scheme 7).

Scheme 7

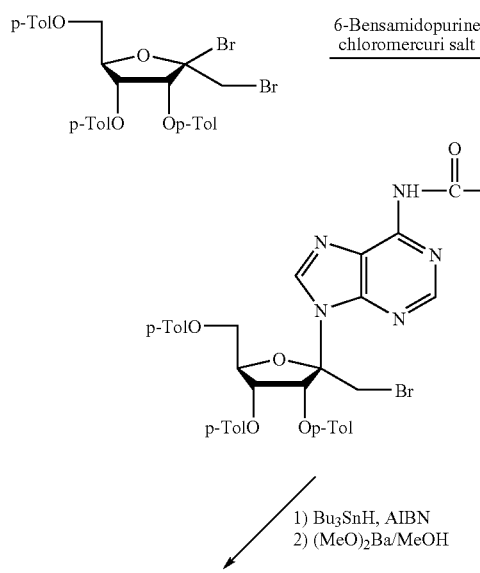

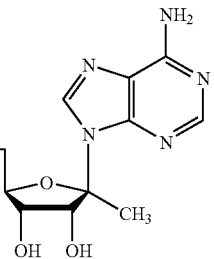

In a similar manner, but using the appropriate sugar and pyrimidine or purine bases, the following nucleosides of Formula I are prepared.

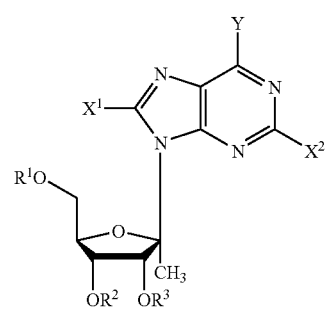

(I)

wherein:

| $R^1$ | $R^2$ | $R^3$ | $X^1$ | $X^2$ | Y |
|---|---|---|---|---|---|
| H | H | H | H | H | H |
| H | H | H | H | H | $NH_2$ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | $NH_2$ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |

-continued

| R¹ | R² | R³ | X¹ | X² | Y |
|---|---|---|---|---|---|
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | $NH_2$ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | $NH_2$ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | $NH_2$ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | $NH_2$ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | $NH_2$ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | $NH_2$ |
| H | H | H | F | H | NH-cyclopropyl |
| H | H | H | F | H | OH |
| H | H | H | F | H | F |
| H | H | H | F | H | Cl |
| H | H | H | Cl | H | $NH_2$ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | $NH_2$ |
| H | H | H | Br | H | NH-cyclopropyl |
| H | H | H | Br | H | OH |

-continued

| R¹ | R² | R³ | X¹ | X² | Y |
|---|---|---|---|---|---|
| H | H | H | Br | H | F |
| H | H | H | Br | H | Cl |
| H | H | H | NH₂ | H | NH₂ |
| H | H | H | NH₂ | H | NH-cyclopropyl |
| H | H | H | NH₂ | H | OH |
| H | H | H | NH₂ | H | F |
| H | H | H | NH₂ | H | Cl |
| H | H | H | SH | H | NH₂ |
| H | H | H | SH | H | NH-cyclopropyl |
| H | H | H | SH | H | OH |
| H | H | H | SH | H | F |
| H | H | H | SH | H | Cl |
| acetyl | H | H | H | H | NH₂ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | NH₂ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | NH₂ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | NH₂ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | NH₂ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | NH₂ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | NH₂ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | NH₂ | H |
| H | H | H | H | NH₂ | NH₂ |
| H | H | H | H | NH₂ | NH-cyclopropyl |
| H | H | H | H | NH₂ | NH-methyl |
| H | H | H | H | NH₂ | NH-ethyl |
| H | H | H | H | NH₂ | NH-acetyl |
| H | H | H | H | NH₂ | OH |
| H | H | H | H | NH₂ | OMe |
| H | H | H | H | NH₂ | OEt |
| H | H | H | H | NH₂ | O-cyclopropyl |
| H | H | H | H | NH₂ | O-acetyl |
| H | H | H | H | NH₂ | SH |
| H | H | H | H | NH₂ | SMe |
| H | H | H | H | NH₂ | SEt |
| H | H | H | H | NH₂ | S-cyclopropyl |
| H | H | H | H | NH₂ | F |
| H | H | H | H | NH₂ | Cl |
| H | H | H | H | NH₂ | Br |
| H | H | H | H | NH₂ | I |
| monophosphate | H | H | H | NH₂ | NH₂ |
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |

-continued

| R¹ | R² | R³ | X¹ | X² | Y |
|---|---|---|---|---|---|
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |

-continued

| R¹ | R² | R³ | X¹ | X² | Y |
|---|---|---|---|---|---|
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |

-continued

| R¹ | R² | R³ | X¹ | X² | Y |
|---|---|---|---|---|---|
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | $NH_2$ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | $NH_2$ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | $NH_2$ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | $NH_2$ |
| triphosphate | triphosphate | triphosphate | H | Cl | NH-cyclopropyl |
| triphosphate | triphosphate | triphosphate | H | Cl | OH |
| H | H | H | F | Cl | $NH_2$ |
| H | H | H | F | Cl | NH-cyclopropyl |
| H | H | H | F | Cl | OH |
| H | H | H | Cl | Cl | $NH_2$ |
| H | H | H | Cl | Cl | NH-cyclopropyl |
| H | H | H | Cl | Cl | OH |
| H | H | H | Br | Cl | $NH_2$ |
| H | H | H | Br | Cl | NH-cyclopropyl |
| H | H | H | Br | Cl | OH |
| H | H | H | $NH_2$ | Cl | $NH_2$ |
| H | H | H | $NH_2$ | Cl | NH-cyclopropyl |
| H | H | H | $NH_2$ | Cl | OH |
| H | H | H | SH | Cl | $NH_2$ |
| H | H | H | SH | Cl | NH-cyclopropyl |
| H | H | H | SH | Cl | OH |
| acetyl | H | H | H | Cl | $NH_2$ |
| acetyl | H | H | H | Cl | NH-cyclopropyl |
| acetyl | H | H | H | Cl | OH |
| acetyl | H | H | F | Cl | $NH_2$ |
| acetyl | H | H | F | Cl | NH-cyclopropyl |
| acetyl | H | H | F | Cl | OH |
| H | acetyl | acetyl | H | Cl | $NH_2$ |
| H | acetyl | acetyl | H | Cl | NH-cyclopropyl |
| H | acetyl | acetyl | H | Cl | OH |
| acetyl | acetyl | acetyl | H | Cl | $NH_2$ |
| acetyl | acetyl | acetyl | H | Cl | NH-cyclopropyl |
| acetyl | acetyl | acetyl | H | Cl | OH |
| monophosphate | acetyl | acetyl | H | Cl | $NH_2$ |
| monophosphate | acetyl | acetyl | H | Cl | NH-cyclopropyl |
| monophosphate | acetyl | acetyl | H | Cl | OH |
| diphosphate | acetyl | acetyl | H | Cl | $NH_2$ |
| diphosphate | acetyl | acetyl | H | Cl | NH-cyclopropyl |
| diphosphate | acetyl | acetyl | H | Cl | OH |
| triphosphate | acetyl | acetyl | H | Cl | $NH_2$ |
| triphosphate | acetyl | acetyl | H | Cl | NH-cyclopropyl |
| triphosphate | acetyl | acetyl | H | Cl | OH |
| H | H | H | H | Cl | $NH_2$ |
| H | H | H | H | Cl | NH-cyclopropyl |
| H | H | H | H | Cl | OH |
| H | H | H | H | Br | $NH_2$ |
| H | H | H | H | Br | NH-cyclopropyl |
| H | H | H | H | Br | OH |

Alternatively, the following nucleosides of Formula IV are prepared, using the appropriate sugar and pyrimidine or purine bases.

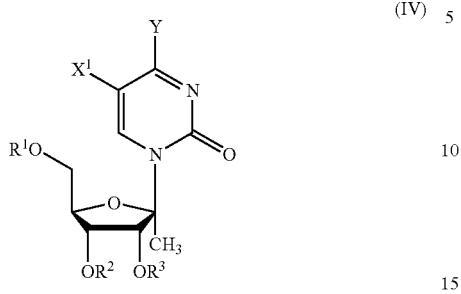

(IV)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | NH₂ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |

-continued

| R¹ | R² | R³ | X¹ | Y |
|---|---|---|---|---|
| triphosphate | H | H | H | SMe |
| triphosphate | H | H | H | SEt |
| triphosphate | H | H | H | S-cyclopropyl |
| monophosphate | monophosphate | monophosphate | H | $NH_2$ |
| monophosphate | monophosphate | monophosphate | H | NH-cyclopropyl |
| monophosphate | monophosphate | monophosphate | H | OH |
| diphosphate | diphosphate | diphosphate | H | $NH_2$ |
| diphosphate | diphosphate | diphosphate | H | NH-cyclopropyl |
| diphosphate | diphosphate | diphosphate | H | OH |
| triphosphate | triphosphate | triphosphate | H | $NH_2$ |
| triphosphate | triphosphate | triphosphate | H | NH-cyclopropyl |
| triphosphate | triphosphate | triphosphate | H | OH |
| H | H | H | F | $NH_2$ |
| H | H | H | F | NH-cyclopropyl |
| H | H | H | F | OH |
| H | H | H | Cl | $NH_2$ |
| H | H | H | Cl | NH-cyclopropyl |
| H | H | H | Cl | OH |
| H | H | H | Br | $NH_2$ |
| H | H | H | Br | NH-cyclopropyl |
| H | H | H | Br | OH |
| H | H | H | $NH_2$ | $NH_2$ |
| H | H | H | $NH_2$ | NH-cyclopropyl |
| H | H | H | $NH_2$ | OH |
| H | H | H | SH | $NH_2$ |
| H | H | H | SH | NH-cyclopropyl |
| H | H | H | SH | OH |
| acetyl | H | H | H | $NH_2$ |
| acetyl | H | H | H | NH-cyclopropyl |
| acetyl | H | H | H | OH |
| acetyl | H | H | F | $NH_2$ |
| acetyl | H | H | F | NH-cyclopropyl |
| acetyl | H | H | F | OH |
| H | acetyl | acetyl | H | $NH_2$ |
| H | acetyl | acetyl | H | NH-cyclopropyl |
| H | acetyl | acetyl | H | OH |
| acetyl | acetyl | acetyl | H | $NH_2$ |
| acetyl | acetyl | acetyl | H | NH-cyclopropyl |
| acetyl | acetyl | acetyl | H | OH |
| monophosphate | acetyl | acetyl | H | $NH_2$ |
| monophosphate | acetyl | acetyl | H | NH-cyclopropyl |
| monophosphate | acetyl | acetyl | H | OH |
| diphosphate | acetyl | acetyl | H | $NH_2$ |
| diphosphate | acetyl | acetyl | H | NH-cyclopropyl |
| diphosphate | acetyl | acetyl | H | OH |
| triphosphate | acetyl | acetyl | H | $NH_2$ |
| triphosphate | acetyl | acetyl | H | NH-cyclopropyl |
| triphosphate | acetyl | acetyl | H | OH |

Alternatively, the following nucleosides of Formula VII are prepared, using the appropriate sugar and pyrimidine or purine bases.

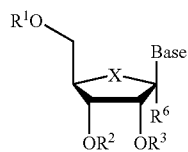

(VII)

wherein:

| R¹ | R² | R³ | R⁶ | X | Base |
|---|---|---|---|---|---|
| H | H | H | $CH_3$ | O | 2,4-O-Diacetyluracil |
| H | H | H | $CH_3$ | O | Hypoxanthine |

-continued

| R¹ | R² | R³ | R⁶ | X | Base |
|---|---|---|---|---|---|
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |

-continued

| R¹ | R² | R³ | R⁶ | X | Base |
|---|---|---|---|---|---|
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |
| H | H | H | CH₃ | S | 8-fluoroguanine |
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |
| H | H | H | CH₃ | S | adenine |
| monophosphate | H | H | CH₃ | O | 2-(N,N-diacetyl)-guanine |
| monophosphate | H | H | CH₃ | O | 6-O-acetyl guanine |

-continued

| R¹ | R² | R³ | R⁶ | X | Base |
|---|---|---|---|---|---|
| monophosphate | H | H | CH₃ | O | 8-fluoroguanine |
| monophosphate | H | H | CH₃ | O | guanine |
| monophosphate | H | H | CH₃ | O | 6-(N,N-diacetyl)-adenine |
| monophosphate | H | H | CH₃ | O | 2-fluoroadenine |
| monophosphate | H | H | CH₃ | O | 8-fluoroadenine |
| monophosphate | H | H | CH₃ | O | 2,8-difluoro-adenine |
| monophosphate | H | H | CH₃ | O | adenine |
| monophosphate | H | H | CH₃ | S | 2-(N,N-diacetyl)-guanine |
| monophosphate | H | H | CH₃ | S | 6-O-acetyl guanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)-adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoro-adenine |
| monophosphate | H | H | CH₃ | S | adenine |
| diphosphate | H | H | CH₃ | O | 2-(N,N-diacetyl)-guanine |
| diphosphate | H | H | CH₃ | O | 6-O-acetyl guanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)-adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoro-adenine |
| diphosphate | H | H | CH₃ | O | adenine |
| diphosphate | H | H | CH₃ | S | 2-(N,N-diacetyl)-guanine |
| diphosphate | H | H | CH₃ | S | 6-O-acetyl guanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)-adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoro-adenine |
| diphosphate | H | H | CH₃ | S | adenine |
| triphosphate | H | H | CH₃ | O | 2-(N,N-diacetyl)-guanine |
| triphosphate | H | H | CH₃ | O | 6-O-acetyl guanine |
| triphosphate | H | H | CH₃ | O | 8-fluoroguanine |
| triphosphate | H | H | CH₃ | O | guanine |
| triphosphate | H | H | CH₃ | O | 6-(N,N-diacetyl)-adenine |
| triphosphate | H | H | CH₃ | O | 2-fluoroadenine |
| triphosphate | H | H | CH₃ | O | 8-fluoroadenine |
| triphosphate | H | H | CH₃ | O | 2,8-difluoro-adenine |
| triphosphate | H | H | CH₃ | O | 2-(N,N-diacetyl)-guanine |
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoro-adenine |
| triphosphate | H | H | CH₃ | S | adenine |
| monophosphate | monophosphate | monophosphate | CF₃ | O | 2-(N,N-diacetyl)-guanine |
| monophosphate | monophosphate | monophosphate | CF₃ | O | 6-O-acetyl guanine |

-continued

| R¹ | R² | R³ | R⁶ | X | Base |
|---|---|---|---|---|---|
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)-adenine |
| monophosphate | monophosphate | monophosphate | CF₃ | O | 2-fluoroadenine |
| monophosphate | monophosphate | monophosphate | CF₃ | O | 8-fluoroadenine |
| monophosphate | monophosphate | monophosphate | CF₃ | O | 2,8-difluoro-adenine |
| monophosphate | monophosphate | monophosphate | CF₃ | O | adenine |
| monophosphate | monophosphate | monophosphate | CF₃ | S | 2-(N,N-diacetyl)-guanine |
| monophosphate | monophosphate | monophosphate | CF₃ | S | 6-O-acetyl guanine |
| monophosphate | monophosphate | monophosphate | CF₃ | S | 8-fluoroguanine |
| monophosphate | monophosphate | monophosphate | CF₃ | S | guanine |
| monophosphate | monophosphate | monophosphate | CF₃ | S | 6-(N,N-diacetyl)-adenine |
| monophosphate | monophosphate | monophosphate | CF₃ | S | 2-fluoroadenine |
| monophosphate | monophosphate | monophosphate | CF₃ | S | 8-fluoroadenine |
| monophosphate | monophosphate | monophosphate | CF₃ | S | 2,8-difluoro-adenine |
| monophosphate | monophosphate | monophosphate | CF₃ | S | adenine |
| acetyl | acetyl | acetyl | CF₃ | O | guanine |
| acetyl | acetyl | acetyl | CF₃ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula VIII are prepared, using the appropriate sugar and pyrimidine or purine bases.

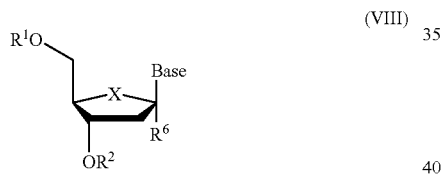

(VIII)

| R¹ | R² | R⁶ | X | Base |
|---|---|---|---|---|
| H | H | CH₃ | O | 2,4-O-Diacetyluracil |
| H | H | CH₃ | O | Hypoxanthine |
| H | H | CH₃ | O | 2,4-O-Diacetylthymine |
| H | H | CH₃ | O | Thymine |
| H | H | CH₃ | O | Cytosine |
| H | H | CH₃ | O | 4-(N-mono-acetyl)cytosine |
| H | H | CH₃ | O | 4-(N,N-diacetyl)cytosine |
| H | H | CH₃ | O | Uracil |
| H | H | CH₃ | O | 5-Fluorouracil |
| H | H | CH₃ | S | 2,4-O-Diacetyluracil |
| H | H | CH₃ | S | Hypoxanthine |
| H | H | CH₃ | S | 2,4-O-Diacetylthymine |
| H | H | CH₃ | S | Thymine |
| H | H | CH₃ | S | Cytosine |
| H | H | CH₃ | S | 4-(N-mono-acetyl)cytosine |
| H | H | CH₃ | S | 4-(N,N-diacetyl)cytosine |
| H | H | CH₃ | S | Uracil |
| H | H | CH₃ | S | 5-Fluorouracil |
| monophosphate | H | CH₃ | O | 2,4-O-Diacetyluracil |
| monophosphate | H | CH₃ | O | Hypoxanthine |
| monophosphate | H | CH₃ | O | 2,4-O-Diacetylthymine |
| monophosphate | H | CH₃ | O | Thymine |
| monophosphate | H | CH₃ | O | Cytosine |
| monophosphate | H | CH₃ | O | 4-(N-mono-acetyl)cytosine |

-continued

| R¹ | R² | R⁶ | X | Base |
|---|---|---|---|---|
| monophosphate | H | CH₃ | O | 4-(N,N-diacetyl)cytosine |
| monophosphate | H | CH₃ | O | Uracil |
| monophosphate | H | CH₃ | O | 5-Fluorouracil |
| monophosphate | H | CH₃ | S | 2,4-O-Diacetyluracil |
| monophosphate | H | CH₃ | S | Hypoxanthine |
| monophosphate | H | CH₃ | S | 2,4-O-Diacetylthymine |
| monophosphate | H | CH₃ | S | Thymine |
| monophosphate | H | CH₃ | S | Cytosine |
| monophosphate | H | CH₃ | S | 4-(N-mono-acetyl)cytosine |
| monophosphate | H | CH₃ | S | 4-(N,N-diacetyl)cytosine |
| monophosphate | H | CH₃ | S | Uracil |
| monophosphate | H | CH₃ | S | 5-Fluorouracil |
| diphosphate | H | CH₃ | O | 2,4-O-Diacetyluracil |
| diphosphate | H | CH₃ | O | Hypoxanthine |
| diphosphate | H | CH₃ | O | 2,4-O-Diacetylthymine |
| diphosphate | H | CH₃ | O | Thymine |
| diphosphate | H | CH₃ | O | Cytosine |
| diphosphate | H | CH₃ | O | 4-(N-mono-acetyl)cytosine |
| diphosphate | H | CH₃ | O | 4-(N,N-diacetyl)cytosine |
| diphosphate | H | CH₃ | O | Uracil |
| diphosphate | H | CH₃ | O | 5-Fluorouracil |
| diphosphate | H | CH₃ | S | 2,4-O-Diacetyluracil |
| diphosphate | H | CH₃ | S | Hypoxanthine |
| diphosphate | H | CH₃ | S | 2,4-O-Diacetylthymine |
| diphosphate | H | CH₃ | S | Thymine |
| diphosphate | H | CH₃ | S | Cytosine |
| diphosphate | H | CH₃ | S | 4-(N-mono-acetyl)cytosine |
| diphosphate | H | CH₃ | S | 4-(N,N-diacetyl)cytosine |
| diphosphate | H | CH₃ | S | Uracil |
| diphosphate | H | CH₃ | S | 5-Fluorouracil |
| triphosphate | H | CH₃ | O | 2,4-O-Diacetyluracil |
| triphosphate | H | CH₃ | O | Hypoxanthine |
| triphosphate | H | CH₃ | O | 2,4-O-diacethylthymine |
| triphosphate | H | CH₃ | O | Thymine |
| triphosphate | H | CH₃ | O | Cytosine |
| triphosphate | H | CH₃ | O | 4-(N-mono-acetyl)cytosine |
| triphosphate | H | CH₃ | O | 4-(N,N-diacetyl)cytosine |
| triphosphate | H | CH₃ | O | Uracil |
| triphosphate | H | CH₃ | O | 5-Fluorouracil |
| triphosphate | H | CH₃ | S | 2,4-O-Diacetyluracil |
| triphosphate | H | CH₃ | S | Hypoxanthine |
| triphosphate | H | CH₃ | S | 2,4-O-Diacetylthymine |
| triphosphate | H | CH₃ | S | Thymine |
| triphosphate | H | CH₃ | S | Cytosine |
| triphosphate | H | CH₃ | S | 4-(N-mono-acetyl)cytosine |
| triphosphate | H | CH₃ | S | 4-(N,N-diacetyl)cytosine |
| triphosphate | H | CH₃ | S | Uracil |
| triphosphate | H | CH₃ | S | 5-Fluorouracil |
| monophosphate | monophosphate | CF₃ | O | 2,4-O-Diacetyluracil |
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-mono-acetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cytosine |
| monophosphate | monophosphate | CF₃ | S | 4-(N-mono-acetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromo-vinyl | O | 4-(N,N-diacetyl)cytosine |
| acetyl | acetyl | 2-bromo-vinyl | S | 4-(N,N-diacetyl)cytosine |
| H | H | CH₃ | O | 2-(N,N-diacetyl)-guanine |
| H | H | CH₃ | O | 6-O-acetyl guanine |
| H | H | CH₃ | O | 8-fluoroguanine |
| H | H | CH₃ | O | guanine |
| H | H | CH₃ | O | 6-(N,N-diacetyl)-adenine |

-continued

| R¹ | R² | R⁶ | X | Base |
|---|---|---|---|---|
| H | H | CH₃ | O | 2-fluoroadenine |
| H | H | CH₃ | O | 8-fluoroadenine |
| H | H | CH₃ | O | 2,8-difluoro-adenine |
| H | H | CH₃ | O | adenine |
| H | H | CH₃ | S | 2-(N,N-diacetyl)-guanine |
| H | H | CH₃ | S | 6-O-acetyl guanine |
| H | H | CH₃ | S | 8-fluoroguanine |
| H | H | CH₃ | S | guanine |
| H | H | CH₃ | S | 6-(N,N-diacetyl)-adenine |
| H | H | CH₃ | S | 2-fluoroadenine |
| H | H | CH₃ | S | 8-fluoroadenine |
| H | H | CH₃ | S | 2,8-difluoro-adenine |
| H | monophosphate | CH₃ | S | adenine |
| monophosphate | H | CH₃ | O | 2-(N,N-diacetyl)-guanine |
| monophosphate | H | CH₃ | O | 6-O-acetyl guanine |
| monophosphate | H | CH₃ | O | 8-fluoroguanine |
| monophosphate | H | CH₃ | O | guanine |
| monophosphate | H | CH₃ | O | 6-(N,N-diacetyl)-adenine |
| monophosphate | H | CH₃ | O | 2-fluoroadenine |
| monophosphate | H | CH₃ | O | 8-fluoroadenine |
| monophosphate | H | CH₃ | O | 2,8-difluoro-adenine |
| monophosphate | H | CH₃ | O | adenine |
| monophosphate | H | CH₃ | S | 2-(N,N-diacetyl)-guanine |
| monophosphate | H | CH₃ | S | 6-O-acetyl guanine |
| monophosphate | H | CH₃ | S | 8-fluoroguanine |
| monophosphate | H | CH₃ | S | guanine |
| monophosphate | H | CH₃ | S | 6-(N,N-diacetyl)-adenine |
| monophosphate | H | CH₃ | S | 2-fluoroadenine |
| monophosphate | H | CH₃ | S | 8-fluoroadenine |
| monophosphate | H | CH₃ | S | 2,8-difluoro-adenine |
| monophosphate | H | CH₃ | S | adenine |
| diphosphate | H | CH₃ | O | 2-(N,N-diacetyl)-guanine |
| diphosphate | H | CH₃ | O | 6-O-acetyl guanine |
| diphosphate | H | CH₃ | O | 8-fluoroguanine |
| diphosphate | H | CH₃ | O | guanine |
| diphosphate | H | CH₃ | O | 6-(N,N-diacetyl)-adenine |
| diphosphate | H | CH₃ | O | 2-fluoroadenine |
| diphosphate | H | CH₃ | O | 8-fluoroadenine |
| diphosphate | H | CH₃ | O | 2,8-difluoro-adenine |
| diphosphate | H | CH₃ | O | adenine |
| diphosphate | H | CH₃ | S | 2-(N,N-diacetyl)-guanine |
| diphosphate | H | CH₃ | S | 6-O-acetyl guanine |
| diphosphate | H | CH₃ | S | 8-fluoroguanine |
| diphosphate | H | CH₃ | S | guanine |
| diphosphate | H | CH₃ | S | 6-(N,N-diacetyl)-adenine |
| diphosphate | H | CH₃ | S | 2-fluoroadenine |
| diphosphate | H | CH₃ | S | 8-fluoroadenine |
| diphosphate | H | CH₃ | S | 2,8-difluoro-adenine |
| diphosphate | H | CH₃ | S | adenine |
| triphosphate | H | CH₃ | O | 2-(N,N-diacetyl)-guanine |
| triphosphate | H | CH₃ | O | 6-O-acetyl guanine |
| triphosphate | H | CH₃ | O | 8-fluoroguanine |
| triphosphate | H | CH₃ | O | guanine |
| triphosphate | H | CH₃ | O | 6-(N,N-diacetyl)-adenine |
| triphosphate | H | CH₃ | O | 2-fluoroadenine |
| triphosphate | H | CH₃ | O | 8-fluoroadenine |
| triphosphate | H | CH₃ | O | 2,8-difluoro-adenine |
| triphosphate | H | CH₃ | O | adenine |
| triphosphate | H | CH₃ | S | 2-(N,N-diacetyl)-guanine |
| triphosphate | H | CH₃ | S | 6-O-acetyl guanine |
| triphosphate | H | CH₃ | S | 8-fluoroguanine |
| triphosphate | H | CH₃ | S | guanine |
| triphosphate | H | CH₃ | S | 6-(N,N-diacetyl)-adenine |
| triphosphate | H | CH₃ | S | 2-fluoroadenine |
| triphosphate | H | CH₃ | S | 8-fluoroadenine |
| triphosphate | H | CH₃ | S | 2,8-difluoro-adenine |
| triphosphate | H | CH₃ | S | adenine |
| monophosphate | monophosphate | CF₃ | O | 2-(N,N-diacetyl)-guanine |
| monophosphate | monophosphate | CF₃ | O | 6-O-acetyl guanine |
| monophosphate | monophosphate | CF₃ | O | 8-fluoroguanine |
| monophosphate | monophosphate | CF₃ | O | guanine |
| monophosphate | monophosphate | CF₃ | O | 6-(N,N-diacetyl)-adenine |
| monophosphate | monophosphate | CF₃ | O | 2-fluoroadenine |
| monophosphate | monophosphate | CF₃ | O | 8-fluoroadenine |
| monophosphate | monophosphate | CF₃ | O | 2,8-difluoro-adenine |
| monophosphate | monophosphate | CF₃ | O | adenine |
| monophosphate | monophosphate | CF₃ | S | 2-(N,N-diacetyl)-guanine |

-continued

| R¹ | R² | R⁶ | X | Base |
|---|---|---|---|---|
| monophosphate | monophosphate | CF₃ | S | 6-O-acetyl guanine |
| monophosphate | monophosphate | CF₃ | S | 8-fluoroguanine |
| monophosphate | monophosphate | CF₃ | S | guanine |
| monophosphate | monophosphate | CF₃ | S | 6-(N,N-diacetyl)-adenine |
| monophosphate | monophosphate | CF₃ | S | 2-fluoroadenine |
| monophosphate | monophosphate | CF₃ | S | 8-fluoroadenine |
| monophosphate | monophosphate | CF₃ | S | 2,8-difluoro-adenine |
| monophosphate | monophosphate | CF₃ | S | adenine |
| acetyl | acetyl | CF₃ | O | guanine |
| acetyl | acetyl | CF₃ | S | guanine |
| acetyl | acetyl | 2-bromo-vinyl | O | guanine |
| acetyl | acetyl | 2-bromo-vinyl | S | guanine |

Alternatively, the following nucleosides of Formula IX are prepared, using the appropriate sugar and pyrimidine or purine bases.

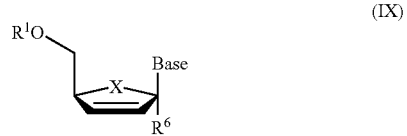

(IX)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | 4-(N,N-diacetyl)cytos |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphospahate | CH₃ | S | 2,4-O-Diacetylthymine |
| triphospahate | CH₃ | S | Thymine |
| triphospahate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytos |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVI are prepared, using the appropriate sugar and pyrimidine or purine bases.

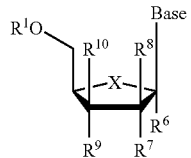

(XVI)

wherein:

| R¹ | R⁶ | R⁷ | R⁸ | X | Base | R¹⁰ | R⁹ |
|---|---|---|---|---|---|---|---|
| H | CH₃ | H | H | O | 2,4-O-Diacetyluracil | OH | Me |
| H | CH₃ | H | H | O | Hypoxanthine | OH | Me |
| H | CH₃ | H | H | O | 2,4-O-Diacetylthymine | OH | Me |
| H | CH₃ | H | H | O | Thymine | OH | Me |
| H | CH₃ | H | H | O | Cytosine | OH | Me |
| H | CH₃ | H | H | O | 4-(N-mono-acetyl)cytosine | OH | Me |
| H | CH₃ | H | H | O | 4-(N,N-diacetyl)cytosine | OH | Me |
| H | CH₃ | H | H | O | Uracil | OH | Me |
| H | CH₃ | H | H | O | 5-Fluorouracil | OH | Me |
| H | CH₃ | H | H | S | 2,4-O-Diacetyluracil | OH | Me |
| H | CH₃ | H | H | S | Hypoxanthine | OH | Me |
| H | CH₃ | H | H | S | 2,4-O-Diacetylthymine | OH | Me |
| H | CH₃ | H | H | S | Thymine | OH | Me |
| H | CH₃ | H | H | S | Cytosine | OH | Me |
| H | CH₃ | H | H | S | 4-(N-mono-acetyl)cytosine | OH | Me |
| H | CH₃ | H | H | S | 4-(N,N-diacetyl)cytosine | OH | Me |
| H | CH₃ | H | H | S | Uracil | OH | Me |
| H | CH₃ | H | H | S | 5-Fluorouracil | OH | Me |
| monophosphate | CH₃ | H | H | O | 2,4-O-Diacetyluracil | OH | Me |
| monophosphate | CH₃ | H | H | O | Hypoxanthine | OH | Me |
| monophosphate | CH₃ | H | H | O | 2,4-O-Diacetylthymine | OH | Me |
| monophosphate | CH₃ | H | H | O | Thymine | OH | Me |
| monophosphate | CH₃ | H | H | O | Cytosine | OH | Me |
| monophosphate | CH₃ | H | H | O | 4-(N-mono-acetyl)cytosine | OH | Me |
| monophosphate | CH₃ | H | H | O | 4-(N,N-diacetyl)cytosine | OH | Me |
| monophosphate | CH₃ | H | H | O | Uracil | OH | Me |
| monophosphate | CH₃ | H | H | O | 5-Fluorouracil | OH | Me |
| monophosphate | CH₃ | H | H | S | 2,4-O-Diacetyluracil | OH | Me |
| monophosphate | CH₃ | H | H | S | Hypoxanthine | OH | Me |
| monophosphate | CH₃ | H | H | S | 2,4-O-Diacetylthymine | OH | Me |
| monophosphate | CH₃ | H | H | S | Thymine | OH | Me |
| monophosphate | CH₃ | H | H | S | Cytosine | OH | Me |
| monophosphate | CH₃ | H | H | S | 4-(N-mono-acetyl)cytosine | OH | Me |
| monophosphate | CH₃ | H | H | S | 4-(N,N-diacetyl)cytosine | OH | Me |
| monophosphate | CH₃ | H | H | S | Uracil | OH | Me |
| monophosphate | CH₃ | H | H | S | 5-Fluorouracil | OH | Me |
| diphosphate | CH₃ | H | H | O | 2,4-O-Diacetyluracil | OH | Me |
| diphosphate | CH₃ | H | H | O | Hypoxanthine | OH | Me |
| diphosphate | CH₃ | H | H | O | 2,4-O-Diacetylthymine | OH | Me |
| diphosphate | CH₃ | H | H | O | Thymine | OH | Me |
| diphosphate | CH₃ | H | H | O | Cytosine | OH | Me |
| diphosphate | CH₃ | H | H | O | 4-(N-mono-acetyl)cytosine | OH | Me |
| diphosphate | CH₃ | H | H | O | 4-(N,N-diacetyl)cytosine | OH | Me |
| diphosphate | CH₃ | H | H | O | Uracil | OH | Me |
| diphosphate | CH₃ | H | H | O | 5-Fluorouracil | OH | Me |
| diphosphate | CH₃ | H | H | S | 2,4-O-Diacetyluracil | OH | Me |
| diphosphate | CH₃ | H | H | S | Hypoxanthine | OH | Me |
| diphosphate | CH₃ | H | H | S | 2,4-O-Diacetylthymine | OH | Me |
| diphosphate | CH₃ | H | H | S | Thymine | OH | Me |
| diphosphate | CH₃ | H | H | S | Cytosine | OH | Me |
| triphosphate | CH₃ | H | H | O | 2,4-O-Diacetyluracil | OH | Me |
| triphosphate | CH₃ | H | H | O | Hypoxanthine | OH | Me |
| triphosphate | CH₃ | H | H | O | 2,4-O-Diacetylthymine | OH | Me |
| triphosphate | CH₃ | H | H | O | Thymine | OH | Me |
| triphosphate | CH₃ | H | H | O | Cytosine | OH | Me |
| triphosphate | CH₃ | H | H | O | 4-(N-mono-acetyl)cytosine | OH | Me |
| triphosphate | CH₃ | H | H | O | 4-(N,N-diacetyl)cytosine | OH | Me |
| triphosphate | CH₃ | H | H | O | Uracil | OH | Me |
| triphosphate | CH₃ | H | H | O | 5-Fluorouracil | OH | Me |
| triphosphate | CH₃ | H | H | S | 2,4-O-Diacetyluracil | OH | Me |
| triphosphate | CH₃ | H | H | S | Hypoxanthine | OH | Me |
| triphosphate | CH₃ | H | H | S | 2,4-O-Diacetylthymine | OH | Me |

-continued

| R¹ | R⁶ | R⁷ | R⁸ | X | Base | R¹⁰ | R⁹ |
|---|---|---|---|---|---|---|---|
| triphosphate | $CH_3$ | H | H | S | Thymine | OH | Me |
| triphosphate | $CH_3$ | H | H | S | Cytosine | OH | Me |
| monophosphate | $CF_3$ | H | H | O | 2,4-O-Diacetyluracil | OH | Me |
| monophosphate | $CF_3$ | H | H | O | Hypoxanthine | OH | Me |
| monophosphate | $CF_3$ | H | H | O | 2,4-O-Diacetylthymine | OH | Me |
| monophosphate | $CF_3$ | H | H | O | Thymine | OH | Me |
| monophosphate | $CF_3$ | H | H | O | Cytosine | OH | Me |
| monophosphate | $CF_3$ | H | H | O | 4-(N-mono-acetyl)cytosine | OH | Me |
| monophosphate | $CF_3$ | H | H | O | 4-(N,N-diacetyl)cytosine | OH | Me |
| monophosphate | $CF_3$ | H | H | O | Uracil | OH | Me |
| monophosphate | $CF_3$ | H | H | O | 5-Fluorouracil | OH | Me |
| monophosphate | $CF_3$ | H | H | S | 2,4-O-Diacetyluracil | OH | Me |
| monophosphate | $CF_3$ | H | H | S | Hypoxanthine | OH | Me |
| monophosphate | $CF_3$ | H | H | S | 2,4-O-Diacetylthymine | OH | Me |
| monophosphate | $CF_3$ | H | H | S | Thymine | OH | Me |
| monophosphate | $CF_3$ | H | H | S | Cytosine | OH | Me |
| monophosphate | $CF_3$ | H | H | S | 4-(N-mono-acetyl)cytosine | OH | Me |
| monophosphate | $CF_3$ | H | H | S | 4-(N,N-diacetyl)cytosine | OH | Me |
| monophosphate | $CF_3$ | H | H | S | Uracil | OH | Me |
| monophosphate | $CF_3$ | H | H | S | 5-Fluorouracil | OH | Me |
| acetyl | $CH_3$ | H | H | O | 4-(N,N-diacetyl)cytosine | H | Br |
| acetyl | $CH_3$ | H | H | S | 4-(N,N-diacetyl)cytosine | H | Br |
| acetyl | $CH_3$ | OH | H | O | 4-(N,N-diacetyl)cytosine | H | Br |
| acetyl | $CH_3$ | OH | H | S | 4-(N,N-diacetyl)cytosine | H | Br |

Example 2

Preparation of 2'-C-methylriboadenine

The title compound was prepared according to a published procedure (R. E. Harry-O'kuru, J. M. Smith, and M. S. Wolfe, "A short, flexible route toward 2'-C-branched ribonucleosides", *J. Org. Chem.* 1997, 62, 1754–1759) (Scheme 8).

Scheme 8

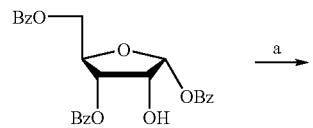

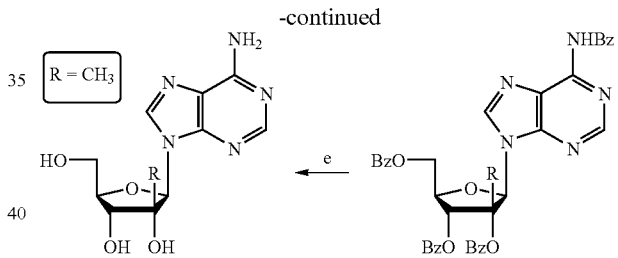

(a) Dess-Martin periodinane; (b) MeMgBr/TiCl₄; (c) BzCl, DMAP, Et₃N; (d) bis(trimethylsilyl)acetamide, N⁶-benzoyl adenine, TMSOTf; (e) NH₃/MeOH In a similar manner, but using the appropriate sugar and pyrimidine or purine bases, the following nucleosides of Formula II are prepared.

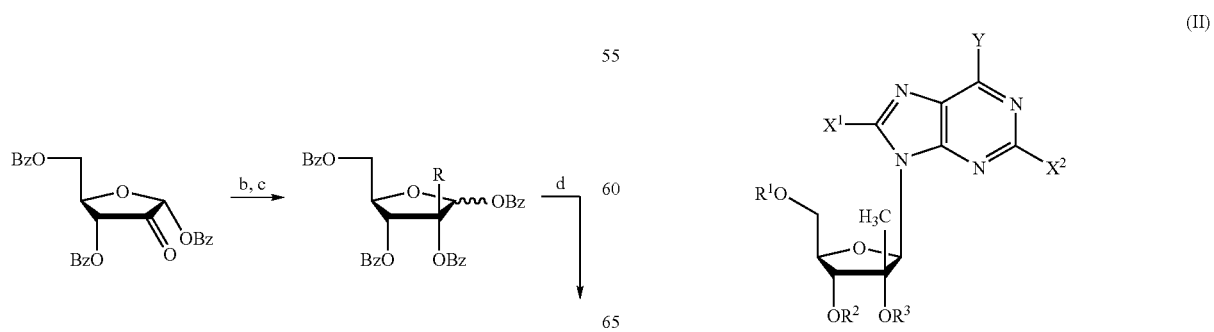

(II)

wherein:

| R¹ | R² | R³ | X¹ | X² | Y |
|---|---|---|---|---|---|
| H | H | H | H | H | H |
| H | H | H | H | H | NH₂ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |

-continued

| R¹ | R² | R³ | X¹ | X² | Y |
|---|---|---|---|---|---|
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | $NH_2$ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | $NH_2$ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | $NH_2$ |
| H | H | H | F | H | NH-cyclopropyl |
| H | H | H | F | H | OH |
| H | H | H | F | H | F |
| H | H | H | F | H | Cl |
| H | H | H | Cl | H | $NH_2$ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | $NH_2$ |
| H | H | H | Br | H | NH-cyclopropyl |
| H | H | H | Br | H | OH |
| H | H | H | Br | H | F |
| H | H | H | Br | H | Cl |
| H | H | H | $NH_2$ | H | $NH_2$ |
| H | H | H | $NH_2$ | H | NH-cyclopropyl |
| H | H | H | $NH_2$ | H | OH |
| H | H | H | $NH_2$ | H | F |
| H | H | H | $NH_2$ | H | Cl |
| H | H | H | SH | H | $NH_2$ |
| H | H | H | SH | H | NH-cyclopropyl |
| H | H | H | SH | H | OH |
| H | H | H | SH | H | F |
| H | H | H | SH | H | Cl |
| acetyl | H | H | H | H | $NH_2$ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | $NH_2$ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | $NH_2$ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | $NH_2$ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | $NH_2$ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | $NH_2$ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | $NH_2$ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | $NH_2$ | H |
| H | H | H | H | $NH_2$ | $NH_2$ |
| H | H | H | H | $NH_2$ | NH-cyclopropyl |
| H | H | H | H | $NH_2$ | NH-methyl |

-continued

| R¹ | R² | R³ | X¹ | X² | Y |
|---|---|---|---|---|---|
| H | H | H | H | NH₂ | NH-ethyl |
| H | H | H | H | NH₂ | NH-acetyl |
| H | H | H | H | NH₂ | OH |
| H | H | H | H | NH₂ | OMe |
| H | H | H | H | NH₂ | OEt |
| H | H | H | H | NH₂ | O-cyclopropyl |
| H | H | H | H | NH₂ | O-acetyl |
| H | H | H | H | NH₂ | SH |
| H | H | H | H | NH₂ | SMe |
| H | H | H | H | NH₂ | SEt |
| H | H | H | H | NH₂ | S-cyclopropyl |
| H | H | H | H | NH₂ | F |
| H | H | H | H | NH₂ | Cl |
| H | H | H | H | NH₂ | Br |
| H | H | H | H | NH₂ | I |
| monophosphate | H | H | H | NH₂ | NH₂ |
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |

-continued

| R¹ | R² | R³ | X¹ | X² | Y |
|---|---|---|---|---|---|
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |

-continued

| R¹ | R² | R³ | X¹ | X² | Y |
|---|---|---|---|---|---|
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | $NH_2$ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | $NH_2$ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | $NH_2$ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | $NH_2$ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | $NH_2$ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | $NH_2$ |
| triphosphate | triphosphate | triphosphate | H | Cl | NH-cyclopropyl |
| triphosphate | triphosphate | triphosphate | H | Cl | OH |
| H | H | H | F | Cl | $NH_2$ |
| H | H | H | F | Cl | NH-cyclopropyl |
| H | H | H | F | Cl | OH |
| H | H | H | Cl | Cl | $NH_2$ |
| H | H | H | Cl | Cl | NH-cyclopropyl |
| H | H | H | Cl | Cl | OH |
| H | H | H | Br | Cl | $NH_2$ |
| H | H | H | Br | Cl | NH-cyclopropyl |
| H | H | H | Br | Cl | OH |
| H | H | H | $NH_2$ | Cl | $NH_2$ |
| H | H | H | $NH_2$ | Cl | NH-cyclopropyl |
| H | H | H | $NH_2$ | Cl | OH |
| H | H | H | SH | Cl | $NH_2$ |
| H | H | H | SH | Cl | NH-cyclopropyl |
| H | H | H | SH | Cl | OH |
| acetyl | H | H | H | Cl | $NH_2$ |
| acetyl | H | H | H | Cl | NH-cyclopropyl |
| acetyl | H | H | H | Cl | OH |
| acetyl | H | H | F | Cl | $NH_2$ |
| acetyl | H | H | F | Cl | NH-cyclopropyl |

-continued

| R¹ | R² | R³ | X¹ | X² | Y |
|---|---|---|---|---|---|
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula V are prepared, using the appropriate sugar and pyrimidine or purine bases.

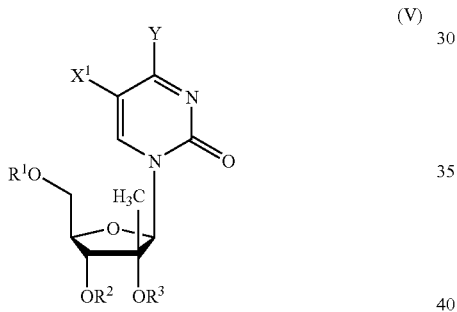

(V)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |

-continued

| R¹ | R² | R³ | X¹ | Y |
|---|---|---|---|---|
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | $NH_2$ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | $NH_2$ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | $NH_2$ |
| monophosphate | monophosphate | monophosphate | H | NH-cyclopropyl |
| monophosphate | monophosphate | monophosphate | H | OH |
| diphosphate | diphosphate | diphosphate | H | $NH_2$ |
| diphosphate | diphosphate | diphosphate | H | NH-cyclopropyl |
| diphosphate | diphosphate | diphosphate | H | OH |
| triphosphate | triphosphate | triphosphate | H | $NH_2$ |
| triphosphate | triphosphate | triphosphate | H | NH-cyclopropyl |
| triphosphate | triphosphate | triphosphate | H | OH |
| H | H | H | F | $NH_2$ |
| H | H | H | F | NH-cyclopropyl |
| H | H | H | F | OH |
| H | H | H | Cl | $NH_2$ |
| H | H | H | Cl | NH-cyclopropyl |
| H | H | H | Cl | OH |
| H | H | H | Br | $NH_2$ |
| H | H | H | Br | NH-cyclopropyl |
| H | H | H | Br | OH |
| H | H | H | $NH_2$ | $NH_2$ |
| H | H | H | $NH_2$ | NH-cyclopropyl |
| H | H | H | $NH_2$ | OH |
| H | H | H | SH | $NH_2$ |
| H | H | H | SH | NH-cyclopropyl |
| H | H | H | SH | OH |
| acetyl | H | H | H | $NH_2$ |
| acetyl | H | H | H | NH-cyclopropyl |
| acetyl | H | H | H | OH |
| acetyl | H | H | F | $NH_2$ |
| acetyl | H | H | F | NH-cyclopropyl |
| acetyl | H | H | F | OH |
| H | acetyl | acetyl | H | $NH_2$ |
| H | acetyl | acetyl | H | NH-cyclopropyl |
| H | acetyl | acetyl | H | OH |
| acetyl | acetyl | acetyl | H | $NH_2$ |
| acetyl | acetyl | acetyl | H | NH-cyclopropyl |
| acetyl | acetyl | acetyl | H | OH |
| monophosphate | acetyl | acetyl | H | $NH_2$ |
| monophosphate | acetyl | acetyl | H | NH-cyclopropyl |
| monophosphate | acetyl | acetyl | H | OH |
| diphosphate | acetyl | acetyl | H | $NH_2$ |
| diphosphate | acetyl | acetyl | H | NH-cyclopropyl |
| diphosphate | acetyl | acetyl | H | OH |

-continued

| R¹ | R² | R³ | X¹ | Y |
|---|---|---|---|---|
| triphosphate | acetyl | acetyl | H | NH₂ |
| triphosphate | acetyl | acetyl | H | NH-cyclopropyl |
| triphosphate | acetyl | acetyl | H | OH |

Alternatively, the following nucleosides of Formula X are prepared, using the appropriate sugar and pyrimidine or purine bases.

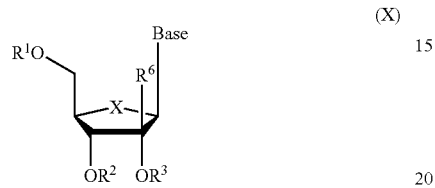

(X)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |

-continued

| R¹ | R² | R³ | R⁶ | X | Base |
|---|---|---|---|---|---|
| monophosphate | H | H | $CH_3$ | S | 4-(N-mono-acetyl)cytosine |
| monophosphate | H | H | $CH_3$ | S | 4-(N,N-diacetyl)cytosine |
| monophosphate | H | H | $CH_3$ | S | Uracil |
| monophosphate | H | H | $CH_3$ | S | 5-Fluorouracil |
| diphosphate | H | H | $CH_3$ | O | 2,4-O-Diacetyluracil |
| diphosphate | H | H | $CH_3$ | O | Hypoxanthine |
| diphosphate | H | H | $CH_3$ | O | 2,4-O-Diacetylthymine |
| diphosphate | H | H | $CH_3$ | O | Thymine |
| diphosphate | H | H | $CH_3$ | O | Cytosine |
| diphosphate | H | H | $CH_3$ | O | 4-(N-mono-acetyl)cytosine |
| diphosphate | H | H | $CH_3$ | O | 4-(N,N-diacetyl)cytosine |
| diphosphate | H | H | $CH_3$ | O | Uracil |
| diphosphate | H | H | $CH_3$ | O | 5-Fluorouracil |
| diphosphate | H | H | $CH_3$ | S | 2,4-O-Diacetyluracil |
| diphosphate | H | H | $CH_3$ | S | Hypoxanthine |
| diphosphate | H | H | $CH_3$ | S | 2,4-O-Diacetylthym |
| diphosphate | H | H | $CH_3$ | S | Thymine |
| diphosphate | H | H | $CH_3$ | S | Cytosine |
| triphosphate | H | H | $CH_3$ | O | 2,4-O-Diacetyluracil |
| triphosphate | H | H | $CH_3$ | O | Hypoxanthine |
| triphosphate | H | H | $CH_3$ | O | 2,4-O-Diacetylthymine |
| triphosphate | H | H | $CH_3$ | O | Thymine |
| triphosphate | H | H | $CH_3$ | O | Cytosine |
| triphosphate | H | H | $CH_3$ | O | 4-(N-mono-acetyl)cytosine |
| triphosphate | H | H | $CH_3$ | O | 4-(N,N-diacetyl)cytosine |
| triphosphate | H | H | $CH_3$ | O | Uracil |
| triphosphate | H | H | $CH_3$ | O | 5-Fluorouracil |
| triphosphate | H | H | $CH_3$ | S | 2,4-O-Diacetyluracil |
| triphosphate | H | H | $CH_3$ | S | Hypoxanthine |
| triphosphate | H | H | $CH_3$ | S | 2,4-O-Diacetylthymine |
| triphosphate | H | H | $CH_3$ | S | Thymine |
| triphosphate | H | H | $CH_3$ | S | Cytosine |
| monophosphate | monophosphate | monophosphate | $CF_3$ | O | 2,4-O-Diacetyluracil |
| monophosphate | monophosphate | monophosphate | $CF_3$ | O | Hypoxanthine |
| monophosphate | monophosphate | monophosphate | $CF_3$ | O | 2,4-O-Diacetylthymine |
| monophosphate | monophosphate | monophosphate | $CF_3$ | O | Thymine |
| monophosphate | monophosphate | monophosphate | $CF_3$ | O | Cytosine |
| monophosphate | monophosphate | monophosphate | $CF_3$ | O | 4-(N-mono-acetyl)cytosine |
| monophosphate | monophosphate | monophosphate | $CF_3$ | O | 4-(N,N-diacetyl)cytosine |
| monophosphate | monophosphate | monophosphate | $CF_3$ | O | Uracil |
| monophosphate | monophosphate | monophosphate | $CF_3$ | O | 5-Fluorouracil |
| monophosphate | monophosphate | monophosphate | $CF_3$ | S | 2,4-O-Diacetyluracil |
| monophosphate | monophosphate | monophosphate | $CF_3$ | S | Hypoxanthine |
| monophosphate | monophosphate | monophosphate | $CF_3$ | S | 2,4-O-Diacetylthymine |
| monophosphate | monophosphate | monophosphate | $CF_3$ | S | Thymine |
| monophosphate | monophosphate | monophosphate | $CF_3$ | S | Cytosine |
| monophosphate | monophosphate | monophosphate | $CF_3$ | S | 4-(N-mono-acetyl)cytosine |
| monophosphate | monophosphate | monophosphate | $CF_3$ | S | 4-(N,N-diacetyl)cytosine |
| monophosphate | monophosphate | monophosphate | $CF_3$ | S | Uracil |
| monophosphate | monophosphate | monophosphate | $CF_3$ | S | 5-Fluorouracil |
| acetyl | acetyl | acetyl | $CF_3$ | O | 4-(N,N-diacetyl)cytosine |
| acetyl | acetyl | acetyl | $CF_3$ | S | 4-(N,N-diacetyl)cytosine |
| acetyl | acetyl | acetyl | 2-bromo-vinyl | O | 4-(N,N-diacetyl)cytosine |

-continued

| R¹ | R² | R³ | R⁶ | X | Base |
|---|---|---|---|---|---|
| acetyl | acetyl | acetyl | 2-bromo-vinyl | S | 4-(N,N-diacetyl)cytosine |
| H | H | H | $CH_3$ | O | 2-(N,N-diacetyl)-guanine |
| H | H | H | $CH_3$ | O | 6-O-acetyl guanine |
| H | H | H | $CH_3$ | O | 8-fluoroguanine |
| H | H | H | $CH_3$ | O | guanine |
| H | H | H | $CH_3$ | O | 6-(N,N-diacetyl)-adenine |
| H | H | H | $CH_3$ | O | 2-fluoroadenine |
| H | H | H | $CH_3$ | O | 8-fluoroadenine |
| H | H | H | $CH_3$ | O | 2,8-difluoro-adenine |
| H | H | H | $CH_3$ | O | adenine |
| H | H | H | $CH_3$ | S | 2-(N,N-diacetyl)-guanine |
| H | H | H | $CH_3$ | S | 6-O-acetyl guanine |
| H | H | H | $CH_3$ | S | 8-fluoroguanine |
| H | H | H | $CH_3$ | S | guanine |
| H | H | H | $CH_3$ | S | 6-(N,N-diacetyl)-adenine |
| H | H | H | $CH_3$ | S | 2-fluoroadenine |
| H | H | H | $CH_3$ | S | 8-fluoroadenine |
| H | H | H | $CH_3$ | S | 2,8-difluoro-adenine |
| H | H | H | $CH_3$ | S | adenine |
| monophosphate | H | H | $CH_3$ | O | 2-(N,N-diacetyl)-guanine |
| monophosphate | H | H | $CH_3$ | O | 6-O-acetyl guanine |
| monophosphate | H | H | $CH_3$ | O | 8-fluoroguanine |
| monophosphate | H | H | $CH_3$ | O | guanine |
| monophosphate | H | H | $CH_3$ | O | 6-(N,N-diacetyl)-adenine |
| monophosphate | H | H | $CH_3$ | O | 2-fluoroadenine |
| monophosphate | H | H | $CH_3$ | O | 8-fluoroadenine |
| monophosphate | H | H | $CH_3$ | O | 2,8-difluoro-adenine |
| monophosphate | H | H | $CH_3$ | O | adenine |
| monophosphate | H | H | $CH_3$ | S | 2-(N,N-diacetyl)-guanine |
| monophosphate | H | H | $CH_3$ | S | 6-O-acetyl guanine |
| monophosphate | H | H | $CH_3$ | S | 8-fluoroguanine |
| monophosphate | H | H | $CH_3$ | S | guanine |
| monophosphate | H | H | $CH_3$ | S | 6-(N,N-diacetyl)-adenine |
| monophosphate | H | H | $CH_3$ | S | 2-fluoroadenine |
| monophosphate | H | H | $CH_3$ | S | 8-fluoroadenine |
| monophosphate | H | H | $CH_3$ | S | 2,8-difluoro-adenine |
| monophosphate | H | H | $CH_3$ | S | adenine |
| diphosphate | H | H | $CH_3$ | O | 2-(N,N-diacetyl)-guanine |
| diphosphate | H | H | $CH_3$ | O | 6-O-acetyl guanine |
| diphosphate | H | H | $CH_3$ | O | 8-fluoroguanine |
| diphosphate | H | H | $CH_3$ | O | guanine |
| diphosphate | H | H | $CH_3$ | O | 6-(N,N-diacetyl)-adenine |
| diphosphate | H | H | $CH_3$ | O | 2-fluoroadenine |
| diphosphate | H | H | $CH_3$ | O | 8-fluoroadenine |
| diphosphate | H | H | $CH_3$ | O | 2,8-difluoro-adenine |
| diphosphate | H | H | $CH_3$ | O | adenine |
| diphosphate | H | H | $CH_3$ | S | 2-(N,N-diacetyl)-guanine |
| diphosphate | H | H | $CH_3$ | S | 6-O-acetyl guanine |
| diphosphate | H | H | $CH_3$ | S | 8-fluoroguanine |
| diphosphate | H | H | $CH_3$ | S | guanine |
| diphosphate | H | H | $CH_3$ | S | 6-(N,N-diacetyl)-adenine |
| diphosphate | H | H | $CH_3$ | S | 2-fluoroadenine |
| diphosphate | H | H | $CH_3$ | S | 8-fluoroadenine |

-continued

| R¹ | R² | R³ | R⁶ | X | Base |
|---|---|---|---|---|---|
| diphosphate | H | H | $CH_3$ | S | 2,8-difluoro-adenine |
| diphosphate | H | H | $CH_3$ | S | adenine |
| triphosphate | H | H | $CH_3$ | O | 2-(N,N-diacetyl)-guanine |
| triphosphate | H | H | $CH_3$ | O | 6-O-acetyl guanine |
| triphosphate | H | H | $CH_3$ | O | 8-fluoroguanine |
| triphosphate | H | H | $CH_3$ | O | guanine |
| triphosphate | H | H | $CH_3$ | O | 6-(N,N-diacetyl)-adenine |
| triphosphate | H | H | $CH_3$ | O | 2-fluoroadenine |
| triphosphate | H | H | $CH_3$ | O | 8-fluoroadenine |
| triphosphate | H | H | $CH_3$ | O | 2,8-difluoro-adenine |
| triphosphate | H | H | $CH_3$ | O | 2-(N,N-diacetyl)-guanine |
| triphosphate | H | H | $CH_3$ | S | 6-O-acetyl guanine |
| triphosphate | H | H | $CH_3$ | S | 8-fluoroguanine |
| triphosphate | H | H | $CH_3$ | S | guanine |
| triphosphate | H | H | $CH_3$ | S | 6-(N,N-diacetyl)-adenine |
| triphosphate | H | H | $CH_3$ | S | 2-fluoroadenine |
| triphosphate | H | H | $CH_3$ | S | 8-fluoroadenine |
| triphosphate | H | H | $CH_3$ | S | 2,8-difluoro-adenine |
| triphosphate | H | H | $CH_3$ | S | adenine |
| monophosphate | monophosphate | monophosphate | $CF_3$ | O | 2-(N,N-diacetyl)-guanine |
| monophosphate | monophosphate | monophosphate | $CF_3$ | O | 6-O-acetyl guanine |
| monophosphate | monophosphate | monophosphate | $CF_3$ | O | 8-fluoroguanine |
| monophosphate | monophosphate | monophosphate | $CF_3$ | O | guanine |
| monophosphate | monophosphate | monophosphate | $CF_3$ | O | 6-(N,N-diacetyl)-adenine |
| monophosphate | monophosphate | monophosphate | $CF_3$ | O | 2-fluoroadenine |
| monophosphate | monophosphate | monophosphate | $CF_3$ | O | 8-fluoroadenine |
| monophosphate | monophosphate | monophosphate | $CF_3$ | O | 2,8-difluoro-adenine |
| monophosphate | monophosphate | monophosphate | $CF_3$ | O | adenine |
| monophosphate | monophosphate | monophosphate | $CF_3$ | S | 2-(N,N-diacetyl)-guanine |
| monophosphate | monophosphate | monophosphate | $CF_3$ | S | 6-O-acetyl guanine |
| monophosphate | monophosphate | monophosphate | $CF_3$ | S | 8-fluoroguanine |
| monophosphate | monophosphate | monophosphate | $CF_3$ | S | guanine |
| monophosphate | monophosphate | monophosphate | $CF_3$ | S | 6-(N,N-diacetyl)-adenine |
| monophosphate | monophosphate | monophosphate | $CF_3$ | S | 2-fluoroadenine |
| monophosphate | monophosphate | monophosphate | $CF_3$ | S | 8-fluoroadenine |
| monophosphate | monophosphate | monophosphate | $CF_3$ | S | 2,8-difluoro-adenine |
| monophosphate | monophosphate | monophosphate | $CF_3$ | S | adenine |
| acetyl | acetyl | acetyl | $CF_3$ | O | guanine |
| acetyl | acetyl | acetyl | $CF_3$ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula XI are prepared, using the appropriate sugar and pyrimidine or purine bases.

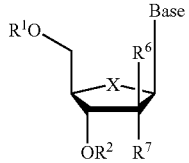

(XI)

wherein:

| R¹ | R² | R⁷ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluracil |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosin |
| H | H | H | CH₃ | S | 4-(N,N-diacetyl)cytosine |
| H | H | H | CH₃ | S | Uracil |
| H | H | H | CH₃ | S | 5-Fluorouracil |
|  |  |  | CH₃ |  |  |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthymine |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthymine |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetylurac |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytos |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthym |
| triphosphate | H | H | CH₃ | S | Thymine |
| triphosphate | H | H | CH₃ | S | Cytosine |
| monophosphate | monophosphate | Br | CF₃ | O | 2,4-O-Diacetyluracil |
| monophosphate | monophosphate | Br | CF₃ | O | Hypoxanthine |
| monophosphate | monophosphate | Br | CF₃ | O | 2,4-O-Diacetylthymine |
| monophosphate | monophosphate | Br | CF₃ | O | Thymine |
| monophosphate | monophosphate | Br | CF₃ | O | Cytosine |

-continued

| R¹ | R² | R⁷ | R⁶ | X | Base |
|---|---|---|---|---|---|
| monophosphate | monophosphate | Br | $CF_3$ | O | 4-(N-mono-acetyl)cytosine |
| monophosphate | monophosphate | Br | $CF_3$ | O | 4-(N,N-diacetyl)cytosine |
| monophosphate | monophosphate | Br | $CF_3$ | O | Uracil |
| monophosphate | monophosphate | Br | $CF_3$ | O | 5-Fluorouracil |
| monophosphate | monophosphate | Br | $CF_3$ | S | 2,4-O-Diacetyluracil |
| monophosphate | monophosphate | Br | $CF_3$ | S | Hypoxanthine |
| monophosphate | monophosphate | Br | $CF_3$ | S | 2,4-O-Diacetylthymine |
| monophosphate | monophosphate | Br | $CF_3$ | S | Thymine |
| monophosphate | monophosphate | Br | $CF_3$ | S | Cytosine |
| monophosphate | monophosphate | Br | $CF_3$ | S | 4-(N-mono-acetyl)cytosine |
| monophosphate | monophosphate | Br | $CF_3$ | S | 4-(N,N-diacetyl)cytos |
| monophosphate | monophosphate | Br | $CF_3$ | S | Uracil |
| monophosphate | monophosphate | Br | $CF_3$ | S | 5-Fluofouracil |
| acetyl | acetyl | NO2 | $CF_3$ | O | 4-(N,N-diacetyl)cytosine |
| acetyl | acetyl | NO2 | $CF_3$ | S | 4-(N,N-diacetyl)cytosine |
| acetyl | acetyl | NO2 | $CF_3$ | O | 4-(N,N-diacetyl)cytosine |
| acetyl | acetyl | NO2 | 2-bromo-vinyl | S | 4-(N,N-diacetyl)cytosine |

Alternatively, the following nucleosides of Formula XII are prepared, using the appropriate sugar and pyrimidine or purine bases.

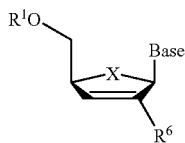

(XII)

wherein:

| R¹ | R⁶ | X | Base |
|---|---|---|---|
| H | $CH_3$ | O | 2,4-O-Diacetyluracil |
| H | $CH_3$ | O | Hypoxanthine |
| H | $CH_3$ | O | 2,4-O-Diacetylthymine |
| H | $CH_3$ | O | Thymine |
| H | $CH_3$ | O | Cytosine |
| H | $CH_3$ | O | 4-(N-mono-acetyl)cytosine |
| H | $CH_3$ | O | 4-(N,N-diacetyl)cytosine |
| H | $CH_3$ | O | Uracil |
| H | $CH_3$ | O | 5-Fluorouracil |
| H | $CH_3$ | S | 2,4-O-Diacetyluracil |
| H | $CH_3$ | S | Hypoxanthine |
| H | $CH_3$ | S | 2,4-O-Diacetylthymine |
| H | $CH_3$ | S | Thymine |
| H | $CH_3$ | S | Cytosine |
| H | $CH_3$ | S | 4-(N-mono-acetyl)cytosine |
| H | $CH_3$ | S | 4-(N,N-diacetyl)cytosine |
| H | $CH_3$ | S | Uracil |
| H | $CH_3$ | S | 5-Fluorouracil |
| monophosphate | $CH_3$ | O | 2,4-O-Diacetyluracil |
| monophosphate | $CH_3$ | O | Hypoxanthine |
| monophosphate | $CH_3$ | O | 2,4-O-Diacetylthymine |
| monophosphate | $CH_3$ | O | Thymine |
| monophosphate | $CH_3$ | O | Cytosine |
| monophosphate | $CH_3$ | O | 4-(N-mono-acetyl)cytosine |
| monophosphate | $CH_3$ | O | 4-(N,N-diacetyl)cytosine |
| monophosphate | $CH_3$ | O | Uracil |
| monophosphate | $CH_3$ | O | 5-Fluorouracil |
| monophosphate | $CH_3$ | S | 2,4-O-Diacetyluracil |
| monophosphate | $CH_3$ | S | Hypoxanthine |
| monophosphate | $CH_3$ | S | 2,4-O-Diacetylthymine |
| monophosphate | $CH_3$ | S | Thymine |
| monophosphate | $CH_3$ | S | Cytosine |
| monophosphate | $CH_3$ | S | 4-(N-mono-acetyl)cytosine |
| monophosphate | $CH_3$ | S | 4-(N,N-diacetyl)cytosine |
| monophosphate | $CH_3$ | S | Uracil |
| monophosphate | $CH_3$ | S | 5-Fluorouracil |
| diphosphate | $2H_3$ | O | 2,4-O-Diacetyluracil |
| diphosphate | $CH_3$ | O | Hypoxanthine |
| diphosphate | $CH_3$ | O | 2,4-O-Diacetylthymine |
| diphosphate | $CH_3$ | O | Thymine |
| diphosphate | $CH_3$ | O | Cytosine |
| diphosphate | $CH_3$ | O | 4-(N-mono-acetyl)cytosine |
| diphosphate | $CH_3$ | O | 4-(N,N-diacetyl)cytosine |
| diphosphate | $CH_3$ | O | Uracil |
| diphosphate | $CH_3$ | O | 5-Fluorouracil |
| diphosphate | $CH_3$ | S | 2,4-O-Diacetyluracil |
| diphosphate | $CH_3$ | S | Hypoxanthine |
| diphosphate | $CH_3$ | S | 2,4-O-Diacetylthymine |
| diphosphate | $CH_3$ | S | Thymine |
| diphosphate | $CH_3$ | S | Cytosine |
| triphosphate | $CH_3$ | O | 2,4-O-Diacetyluracil |
| triphosphate | $CH_3$ | O | Hypoxanthine |
| triphosphate | $CH_3$ | O | 2,4-O-Diacetylthymine |
| triphosphate | $CH_3$ | O | Thymine |
| triphosphate | $CH_3$ | O | Cytosine |
| triphosphate | $CH_3$ | O | 4-(N-mono-acetyl)cytosine |
| triphosphate | $CH_3$ | O | 4-(N,N-diacetyl)cytosine |
| triphosphate | $CH_3$ | O | Uracil |
| triphosphate | $CH_3$ | O | 5-Fluorouracil |
| triphosphate | $CH_3$ | S | 2,4-O-Diacetyluracil |
| triphosphate | $CH_3$ | S | 2,4-O-Diacetylthymine |
| triphosphate | $CH_3$ | S | Thymine |
| triphosphate | $CH_3$ | S | Cytosine |
| monophosphate | $CF_3$ | O | 2,4-O-Diacetyluracil |
| monophosphate | $CF_3$ | O | Hypoxanthine |
| monophosphate | $CF_3$ | O | 2,4-O-Diacetylthymine |
| monophosphate | $CF_3$ | O | Thymine |
| monophosphate | $CF_3$ | O | Cytosine |
| monophosphate | $CF_3$ | O | 4-(N-mono-acetyl)cytosine |

| R¹ | R⁶ | X | Base |
|---|---|---|---|
| monophosphate | CF₃ | O | 4-(N,N-diacetyl)cytosine |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVII are prepared, using the appropriate sugar and pyrimidine or purine bases.

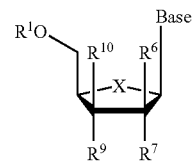

(XVII)

wherein:

| R¹ | R⁶ | R⁷ | X | Base | R⁹ | R¹⁰ |
|---|---|---|---|---|---|---|
| H | CH₃ | H | O | 2,4-O-Diacetyluracil | NHAc | Me |
| H | CH₃ | H | O | Hypoxanthine | NH2 | Me |
| H | CH₃ | H | O | 2,4-O-Diacetylthymine | NHAc | Me |
| H | CH₃ | H | O | Thymine | NH2 | Me |
| H | CH₃ | H | O | Cytosine | NH2 | Me |
| H | CH₃ | H | O | 4-(N-mono-acetyl)cytosine | NHAc | Me |
| H | CH₃ | H | O | 4-(N,N-diacetyl)cytosine | NHAc | Me |
| H | CH₃ | H | O | Uracil | NH2 | Me |
| H | CH₃ | H | O | 5-Fluorouracil | NH2 | Me |
| H | CH₃ | H | S | 2,4-O-Diacetyluracil | NHAc | Me |
| H | CH₃ | H | S | Hypoxanthine | NH2 | Me |
| H | CH₃ | H | S | 2,4-O-Diacetylthymine | NHAc | Me |
| H | CH₃ | H | S | Thymine | NH2 | Me |
| H | CH₃ | H | S | Cytosine | NH2 | Me |
| H | CH₃ | H | S | 4-(N-mono-acetyl)cytosine | NHAc | Me |
| H | CH₃ | H | S | 4-(N,N-diacetyl)cytosine | NHAc | Me |
| H | CH₃ | H | S | Uracil | NH2 | Me |
| H | CH₃ | H | S | 5-Fluorouracil | NH2 | Me |
| monophosphate | CH₃ | H | O | 2,4-O-Diacetyluracil | NHAc | Me |
| monophosphate | CH₃ | H | O | Hypoxanthine | NH2 | Me |
| monophosphate | CH₃ | H | O | 2,4-O-Diacetylthymine | NHAc | Me |
| monophosphate | CH₃ | H | O | Thymine | NH2 | Me |
| monophosphate | CH₃ | H | O | Cytosine | NH2 | Me |
| monophosphate | CH₃ | H | O | 4-(N-mono-acetyl)cytosine | NHAC | Me |
| monophosphate | CH₃ | H | O | 4-(N,N-diacetyl)cytosine | NHAc | Me |
| monophosphate | CH₃ | H | O | Uracil | NH2 | Me |
| monophosphate | CH₃ | H | O | 5-Fluorouracil | NH2 | Me |
| monophosphate | CH₃ | H | S | 2,4-O-Diacetyluracil | NHAc | Me |
| monophosphate | CH₃ | H | S | Hypoxanthine | NH2 | Me |
| monophosphate | CH₃ | H | S | 2,4-O-Diacetylthymine | NHAc | Me |
| monophosphate | CH₃ | H | S | Thymine | NH2 | Me |
| monophosphate | CH₃ | H | S | Cytosine | NH2 | Me |
| monophosphate | CH₃ | H | S | 4-(N-mono-acetyl)cytosine | NHAc | Me |
| monophosphate | CH₃ | H | S | 4-(N,N-diacetyl)cytosine | NHAc | Me |
| monophosphate | CH₃ | H | S | Uracil | NH2 | Me |
| monophosphate | CH₃ | H | S | 5-Fluorouracil | NH2 | Me |
| diphosphate | CH₃ | H | O | 2,4-O-Diacetyluracil | NHAc | Me |
| diphosphate | CH₃ | H | O | Hypoxanthine | NH2 | Me |
| diphosphate | CH₃ | H | O | 2,4-O-Diacetylthymine | NH2 | Me |
| diphosphate | CH₃ | H | O | Thymine | NH2 | Me |
| diphosphate | CH₃ | H | O | Cytosine | NH2 | Me |
| diphosphate | CH₃ | H | O | 4-(N-mono-acetyl)cytosine | NHAc | Me |
| diphosphate | CH₃ | H | O | 4-(N,N-diacetyl)cytos | NHAc | Me |
| diphosphate | CH₃ | H | O | Uracil | NH2 | Me |
| diphosphate | CH₃ | H | O | 5-Fluorouracil | NH2 | Me |
| diphosphate | CH₃ | H | S | 2,4-O-Diacetyluracil | NH2 | Me |
| diphosphate | CH₃ | H | S | Hypoxanthine | NH2 | Me |
| diphosphate | CH₃ | H | S | 2,4-O-Diacetylthymine | NHAc | Me |
| diphosphate | CH₃ | H | S | Thymine | NH2 | Me |

-continued

| R¹ | R⁶ | R⁷ | X | Base | R⁹ | R¹⁰ |
|---|---|---|---|---|---|---|
| diphosphate | CH₃ | H | S | Cytosine | NH2 | Me |
| triphosphate | CH₃ | H | O | 2,4-O-Diacetyluracil | NHAc | Me |
| triphosphate | CH₃ | H | O | Hypoxanthine | NHAc | Me |
| triphosphate | CH₃ | H | O | 2,4-O-Diacetylthymine | NHAc | Me |
| triphosphate | CH₃ | H | O | Thymine | NH2 | Me |
| triphosphate | CH₃ | H | O | Cytosine | NH2 | Me |
| triphosphate | CH₃ | H | O | 4-(N-mono-acetyl)cytosine | NHAc | Me |
| triphosphate | CH₃ | H | O | 4-(N,N-diacetyl)cytosine | NH2 | Me |
| triphosphate | CH₃ | H | O | Uracil | NH2 | Me |
| triphosphate | CH₃ | H | O | 5-Fluorouracil | NH2 | Me |
| triphosphate | CH₃ | H | S | 2,4-O-Diacetyluracil | NH2 | Me |
| triphosphate | CH₃ | H | S | Hypoxanthine | NH2 | Me |
| triphosphate | CH₃ | H | S | 2,4-O-Diacetylthymine | NH2 | Me |
| triphosphate | CH₃ | H | S | Thymine | NH2 | Me |
| triphosphate | CH₃ | H | S | Cytosine | NH2 | Me |
| monophosphate | CF₃ | H | O | 2,4-O-Diacetyluracil | NH2 | Me |
| monophosphate | CF₃ | H | O | Hypoxanthine | NH2 | Me |
| monophosphate | CF₃ | H | O | 2,4-O-Diacetylthymine | NH2 | Me |
| monophosphate | CF₃ | H | O | Thymine | NH2 | Me |
| monophosphate | CF₃ | H | O | Cytosine | NH2 | Me |
| monophosphate | CF₃ | H | O | 4-(N-mono-acetyl)cytosine | NH2 | Me |
| monophosphate | CF₃ | H | O | 4-(N,N-diacetyl)cytosine | NH2 | Me |
| monophosphate | CF₃ | H | O | Uracil | NH2 | Me |
| monophosphate | CF₃ | H | O | 5-Fluorouracil | NH2 | Me |
| monophosphate | CF₃ | H | S | 2,4-O-Diacetyluracil | NH2 | Me |
| monophosphate | CF₃ | H | S | Hypoxanthine | NH2 | Me |
| monophosphate | CF₃ | H | S | 2,4-O-Diacetylthymine | NH2 | Me |
| monophosphate | CF₃ | H | S | Thymine | NH2 | Me |
| monophosphate | CF₃ | H | S | Cytosine | NH2 | Me |
| monophosphate | CF₃ | H | S | 4-(N-mono-acetyl)cytosine | NH2 | Me |
| monophosphate | CF₃ | H | S | 4-(N,N-diacetyl)cytosine | NH2 | Me |
| monophosphate | CF₃ | H | S | Uracil | NH2 | Me |
| monophosphate | CF₃ | H | S | 5-Fluorouracil | NH2 | Me |
| acetyl | CH₃ | H | O | 4-(N,N-diacetyl)cytosine | H | Br |
| acetyl | CH₃ | H | S | 4-(N,N-diacetyl)cytosine | H | Br |
| acetyl | CH₃ | OH | O | 4-(N,N-diacetyl)cytosine | H | Br |
| acetyl | CH₃ | OH | S | 4-(N,N-diacetyl)cytosine | H | Br |

Example 3

Preparation of 3'-C-methylriboadenine

The title compound can be prepared according to a published procedure (R. F. Nutt, M. J. Dickinson, F. W. Holly, and E. Walton, "Branched-chain sugar nucleosides. III. 3'-C-methyladenine", *J. Org. Chem.* 1968, 33, 1789–1795) (Scheme 9).

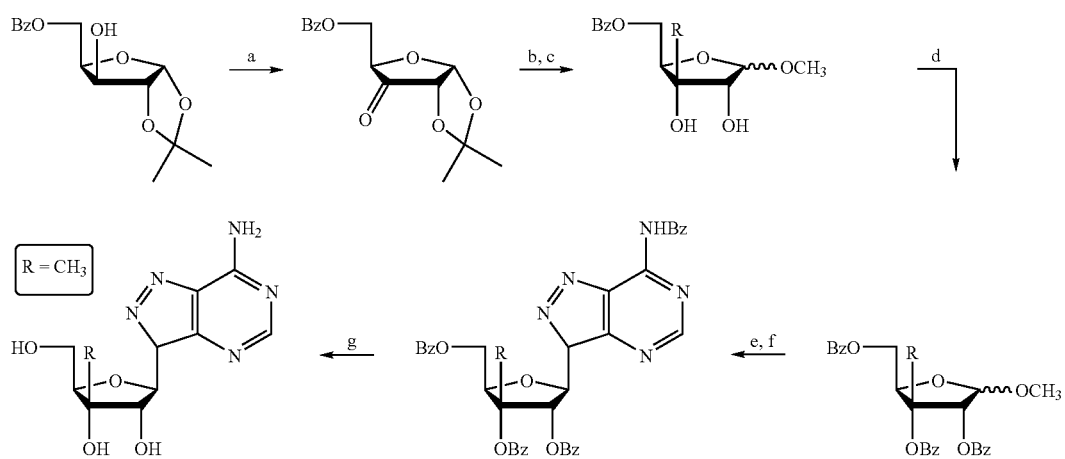

Scheme 9

(a) RuO₂/NaIO₂; (b) MeMgI/TiCl₄; (c) HCl/MeOH/H₂O; (d) BzCl/pyridine; (e) AcBr, HBr/AcOH; (f) chloromercuri-6-benzamidopurine; (g) NH₃/MeOH.

In a similar manner, but using the appropriate sugar and pyrimidine or purine bases, the following nucleosides of Formula III are prepared.

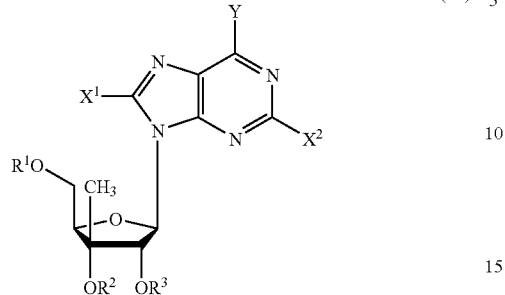

(III)

wherein:

| R¹ | R² | R³ | X¹ | X² | Y |
|---|---|---|---|---|---|
| H | H | H | H | H | H |
| H | H | H | H | H | NH₂ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |

-continued

| R¹ | R² | R³ | X¹ | X² | Y |
|---|---|---|---|---|---|
| diphosphate | H | H | H | H | Cl |
| diphosphate | H | H | H | H | Br |
| diphosphate | H | H | H | H | I |
| triphosphate | H | H | H | H | $NH_2$ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | $NH_2$ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | $NH_2$ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | $NH_2$ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | $NH_2$ |
| H | H | H | F | H | NH-cyclopropyl |
| H | H | H | F | H | OH |
| H | H | H | F | H | F |
| H | H | H | F | H | Cl |
| H | H | H | Cl | H | $NH_2$ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | $NH_2$ |
| H | H | H | Br | H | NH-cyclopropyl |
| H | H | H | Br | H | OH |
| H | H | H | Br | H | F |
| H | H | H | Br | H | Cl |
| H | H | H | $NH_2$ | H | $NH_2$ |
| H | H | H | $NH_2$ | H | NH-cyclopropyl |
| H | H | H | $NH_2$ | H | OH |
| H | H | H | $NH_2$ | H | F |
| H | H | H | $NH_2$ | H | Cl |
| H | H | H | SH | H | $NH_2$ |
| H | H | H | SH | H | NH-cyclopropyl |
| H | H | H | SH | H | OH |
| H | H | H | SH | H | F |
| H | H | H | SH | H | Cl |
| acetyl | H | H | H | H | $NH_2$ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | $NH_2$ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | $NH_2$ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | $NH_2$ |

-continued

| R¹ | R² | R³ | X¹ | X² | Y |
|---|---|---|---|---|---|
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | NH$_2$ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | NH$_2$ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | NH$_2$ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | NH$_2$ | H |
| H | H | H | H | NH$_2$ | NH$_2$ |
| H | H | H | H | NH$_2$ | NH-cyclopropyl |
| H | H | H | H | NH$_2$ | NH-methyl |
| H | H | H | H | NH$_2$ | NH-ethyl |
| H | H | H | H | NH$_2$ | NH-acetyl |
| H | H | H | H | NH$_2$ | OH |
| H | H | H | H | NH$_2$ | OMe |
| H | H | H | H | NH$_2$ | OEt |
| H | H | H | H | NH$_2$ | O-cyclopropyl |
| H | H | H | H | NH$_2$ | O-acetyl |
| H | H | H | H | NH$_2$ | SH |
| H | H | H | H | NH$_2$ | SMe |
| H | H | H | H | NH$_2$ | SEt |
| H | H | H | H | NH$_2$ | S-cyclopropyl |
| H | H | H | H | NH$_2$ | F |
| H | H | H | H | NH$_2$ | Cl |
| H | H | H | H | NH$_2$ | Br |
| H | H | H | H | NH$_2$ | I |
| monophosphate | H | H | H | NH$_2$ | NH$_2$ |
| monophosphate | H | H | H | NH$_2$ | NH-acetyl |
| monophosphate | H | H | H | NH$_2$ | NH-cyclopropyl |
| monophosphate | H | H | H | NH$_2$ | NH-methyl |
| monophosphate | H | H | H | NH$_2$ | NH-ethyl |
| monophosphate | H | H | H | NH$_2$ | OH |
| monophosphate | H | H | H | NH$_2$ | O-acetyl |
| monophosphate | H | H | H | NH$_2$ | OMe |
| monophosphate | H | H | H | NH$_2$ | OEt |
| monophosphate | H | H | H | NH$_2$ | O-cyclopropyl |
| monophosphate | H | H | H | NH$_2$ | SH |
| monophosphate | H | H | H | NH$_2$ | SMe |
| monophosphate | H | H | H | NH$_2$ | SEt |
| monophosphate | H | H | H | NH$_2$ | S-cyclopropyl |
| monophosphate | H | H | H | NH$_2$ | F |
| monophosphate | H | H | H | NH$_2$ | Cl |
| monophosphate | H | H | H | NH$_2$ | Br |
| monophosphate | H | H | H | NH$_2$ | I |
| diphosphate | H | H | H | NH$_2$ | NH$_2$ |
| diphosphate | H | H | H | NH$_2$ | NH-acetyl |
| diphosphate | H | H | H | NH$_2$ | NH-cyclopropyl |
| diphosphate | H | H | H | NH$_2$ | NH-methyl |
| diphosphate | H | H | H | NH$_2$ | NH-ethyl |
| diphosphate | H | H | H | NH$_2$ | OH |
| diphosphate | H | H | H | NH$_2$ | O-acetyl |
| diphosphate | H | H | H | NH$_2$ | OMe |
| diphosphate | H | H | H | NH$_2$ | OEt |
| diphosphate | H | H | H | NH$_2$ | O-cyclopropyl |
| diphosphate | H | H | H | NH$_2$ | SH |
| diphosphate | H | H | H | NH$_2$ | SMe |
| diphosphate | H | H | H | NH$_2$ | SEt |
| diphosphate | H | H | H | NH$_2$ | S-cyclopropyl |
| diphosphate | H | H | H | NH$_2$ | F |
| diphosphate | H | H | H | NH$_2$ | Cl |
| diphosphate | H | H | H | NH$_2$ | Br |
| diphosphate | H | H | H | NH$_2$ | I |
| triphosphate | H | H | H | NH$_2$ | NH$_2$ |
| triphosphate | H | H | H | NH$_2$ | NH-acetyl |
| triphosphate | H | H | H | NH$_2$ | NH-cyclopropyl |

-continued

| R¹ | R² | R³ | X¹ | X² | Y |
|---|---|---|---|---|---|
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |

-continued

| R¹ | R² | R³ | X¹ | X² | Y |
|---|---|---|---|---|---|
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | NH₂ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | NH₂ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | NH₂ |
| diphosphate | diphosphate | diphosphate | H | Cl | NH-cyclopropyl |
| diphosphate | diphosphate | diphosphate | H | Cl | OH |

-continued

| R¹ | R² | R³ | X¹ | X² | Y |
|---|---|---|---|---|---|
| triphosphate | triphosphate | triphosphate | H | Cl | NH₂ |
| triphosphate | triphosphate | triphosphate | H | Cl | NH-cyclopropyl |
| triphosphate | triphosphate | triphosphate | H | Cl | OH |
| H | H | H | F | Cl | NH₂ |
| H | H | H | F | Cl | NH-cyclopropyl |
| H | H | H | F | Cl | OH |
| H | H | H | Cl | Cl | NH₂ |
| H | H | H | Cl | Cl | NH-cyclopropyl |
| H | H | H | Cl | Cl | OH |
| H | H | H | Br | Cl | NH₂ |
| H | H | H | Br | Cl | NH-cyclopropyl |
| H | H | H | Br | Cl | OH |
| H | H | H | NH₂ | Cl | NH₂ |
| H | H | H | NH₂ | Cl | NH-cyclopropyl |
| H | H | H | NH₂ | Cl | OH |
| H | H | H | SH | Cl | NH₂ |
| H | H | H | SH | Cl | NH-cyclopropyl |
| H | H | H | SH | Cl | OH |
| acetyl | H | H | H | Cl | NH₂ |
| acetyl | H | H | H | Cl | NH-cyclopropyl |
| acetyl | H | H | H | Cl | OH |
| acetyl | H | H | F | Cl | NH₂ |
| acetyl | H | H | F | Cl | NH-cyclopropyl |
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula VI are prepared, using the appropriate sugar and pyrimidine or purine bases.

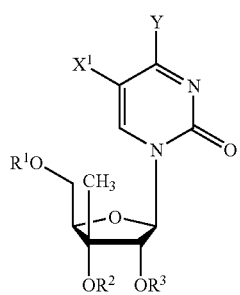

(VI)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | NH₂ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | NH₂ |
| monophosphate | monophosphate | monophosphate | H | NH-cyclopropyl |
| monophosphate | monophosphate | monophosphate | H | OH |
| diphosphate | diphosphate | diphosphate | H | NH₂ |
| diphosphate | diphosphate | diphosphate | H | NH-cyclopropyl |
| diphosphate | diphosphate | diphosphate | H | OH |
| triphosphate | triphosphate | triphosphate | H | NH₂ |
| triphosphate | triphosphate | triphosphate | H | NH-cyclopropyl |
| triphosphate | triphosphate | triphosphate | H | OH |
| H | H | H | F | NH₂ |
| H | H | H | F | NH-cyclopropyl |
| H | H | H | F | OH |
| H | H | H | Cl | NH₂ |
| H- | H | H | Cl | NH-cyclopropyl |
| H | H | H | Cl | OH |
| H | H | H | Br | NH₂ |
| H | H | H | Br | NH-cyclopropyl |
| H | H | H | Br | OH |
| H | H | H | NH₂ | NH₂ |
| H | H | H | NH₂ | NH-cyclopropyl |

-continued

| R¹ | R² | R³ | X¹ | Y |
|---|---|---|---|---|
| H | H | H | NH₂ | OH |
| H | H | H | SH | NH₂ |
| H | H | H | SH | NH-cyclopropyl |
| H | H | H | SH | OH |
| acetyl | H | H | H | NH₂ |
| acetyl | H | H | H | NH-cyclopropyl |
| acetyl | H | H | H | OH |
| acetyl | H | H | F | NH₂ |
| acetyl | H | H | F | NH-cyclopropyl |
| acetyl | H | H | F | OH |
| H | acetyl | acetyl | H | NH₂ |
| H | acetyl | acetyl | H | NH-cyclopropyl |
| H | acetyl | acetyl | H | OH |
| acetyl | acetyl | acetyl | H | NH₂ |
| acetyl | acetyl | acetyl | H | NH-cyclopropyl |
| acetyl | acetyl | acetyl | H | OH |
| monophosphate | acetyl | acetyl | H | NH₂ |
| monophosphate | acetyl | acetyl | H | NH-cyclopropyl |
| monophosphate | acetyl | acetyl | H | OH |
| diphosphate | acetyl | acetyl | H | NH₂ |
| diphosphate | acetyl | acetyl | H | NH-cyclopropyl |
| diphosphate | acetyl | acetyl | H | OH |
| triphosphate | acetyl | acetyl | H | NH₂ |
| triphosphate | acetyl | acetyl | H | NH-cyclopropyl |
| triphosphate | acetyl | acetyl | H | OH |

Alternatively, the following nucleosides of Formula XIII are prepared, using the appropriate sugar and pyrimidine or purine bases.

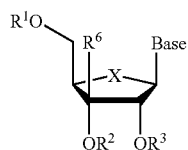

(XIII)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |

-continued

| R¹ | R² | R³ | R⁶ | X | Base |
|---|---|---|---|---|---|
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |
| H | H | H | CH₃ | S | 8-fluoroguanine |
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |

-continued

| R¹ | R² | R³ | R⁶ | X | Base |
|---|---|---|---|---|---|
| H | H | H | $CH_3$ | S | adenine |
| monophosphate | H | H | $CH_3$ | O | 2-(N,N-diacetyl)-guanine |
| monophosphate | H | H | $CH_3$ | O | 6-O-acetyl guanine |
| monophosphate | H | H | $CH_3$ | O | 8-fluoroguanine |
| monophosphate | H | H | $CH_3$ | O | guanine |
| monophosphate | H | H | $CH_3$ | O | 6-(N,N-diacetyl)-adenine |
| monophosphate | H | H | $CH_3$ | O | 2-fluoroadenine |
| monophosphate | H | H | $CH_3$ | O | 8-fluoroadenine |
| monophosphate | H | H | $CH_3$ | O | 2,8-difluoro-adenine |
| monophosphate | H | H | $CH_3$ | O | adenine |
| monophosphate | H | H | $CH_3$ | S | 2-(N,N-diacetyl)-guanine |
| monophosphate | H | H | $CH_3$ | S | 6-O-acetyl guanine |
| monophosphate | H | H | $CH_3$ | S | 8-fluoroguanine |
| monophosphate | H | H | $CH_3$ | S | guanine |
| monophosphate | H | H | $CH_3$ | S | 6-(N,N-diacetyl)-adenine |
| monophosphate | H | H | $CH_3$ | S | 2-fluoroadenine |
| monophosphate | H | H | $CH_3$ | S | 8-fluoroadenine |
| monophosphate | H | H | $CH_3$ | S | 2,8-difluoro-adenine |
| monophosphate | H | H | $CH_3$ | S | adenine |
| diphosphate | H | H | $CH_3$ | O | 2-(N,N-diacetyl)-guanine |
| diphosphate | H | H | $CH_3$ | O | 6-O-acetyl guanine |
| diphosphate | H | H | $CH_3$ | O | 8-fluoroguanine |
| diphosphate | H | H | $CH_3$ | O | guanine |
| diphosphate | H | H | $CH_3$ | O | 6-(N,N-diacetyl)-adenine |
| diphosphate | H | H | $CH_3$ | O | 2-fluoroadenine |
| diphosphate | H | H | $CH_3$ | O | 8-fluoroadenine |
| diphosphate | H | H | $CH_3$ | O | 2,8-difluoro-adenine |
| diphosphate | H | H | $CH_3$ | O | adenine |
| diphosphate | H | H | $CH_3$ | S | 2-(N,N-diacetyl)-guanine |
| diphosphate | H | H | $CH_3$ | S | 6-O-acetyl guanine |
| diphosphate | H | H | $CH_3$ | S | 8-fluoroguanine |
| diphosphate | H | H | $CH_3$ | S | guanine |
| diphosphate | H | H | $CH_3$ | S | 6-(N,N-diacetyl)-adenine |
| diphosphate | H | H | $CH_3$ | S | 2-fluoroadenine |
| diphosphate | H | H | $CH_3$ | S | 8-fluoroadenine |
| diphosphate | H | H | $CH_3$ | S | 2,8-difluoro-adenine |
| diphosphate | H | H | $CH_3$ | S | adenine |
| triphosphate | H | H | $CH_3$ | O | 2-(N,N-diacetyl)-guanine |
| triphosphate | H | H | $CH_3$ | O | 6-O-acetyl guanine |
| triphosphate | H | H | $CH_3$ | O | 8-fluoroguanine |
| triphosphate | H | H | $CH_3$ | O | guanine |
| triphosphate | H | H | $CH_3$ | O | 6-(N,N-diacetyl)-adenine |
| triphosphate | H | H | $CH_3$ | O | 2-fluoroadenine |
| triphosphate | H | H | $CH_3$ | O | 8-fluoroadenine |
| triphosphate | H | H | $CH_3$ | O | 2,8-difluoro-adenine |
| triphosphate | H | H | $CH_3$ | O | 2-(N,N-diacetyl)-guanine |
| triphosphate | H | H | $CH_3$ | S | 6-O-acetyl guanine |
| triphosphate | H | H | $CH_3$ | S | 8-fluoroguanine |
| triphosphate | H | H | $CH_3$ | S | guanine |
| triphosphate | H | H | $CH_3$ | S | 6-(N,N-diacetyl)-adenine |
| triphosphate | H | H | $CH_3$ | S | 2-fluoroadenine |
| triphosphate | H | H | $CH_3$ | S | 8-fluoroadenine |
| triphosphate | H | H | $CH_3$ | S | 2,8-difluoro-adenine |
| triphosphate | H | H | $CH_3$ | S | adenine |
| monophosphate | monophosphate | monophosphate | $CF_3$ | O | 2-(N,N-diacetyl)-guanine |
| monophosphate | monophosphate | monophosphate | $CF_3$ | O | 6-O-acetyl guanine |
| monophosphate | monophosphate | monophosphate | $CF_3$ | O | 8-fluoroguanine |
| monophosphate | monophosphate | monophosphate | $CF_3$ | O | guanine |
| monophosphate | monophosphate | monophosphate | $CF_3$ | O | 6-(N,N-diacetyl)-adenine |
| monophosphate | monophosphate | monophosphate | $CF_3$ | O | 2-fluoroadenine |
| monophosphate | monophosphate | monophosphate | $CF_3$ | O | 8-fluoroadenine |
| monophosphate | monophosphate | monophosphate | $CF_3$ | O | 2,8-difluoro-adenine |
| monophosphate | monophosphate | monophosphate | $CF_3$ | O | adenine |
| monophosphate | monophosphate | monophosphate | $CF_3$ | S | 2-(N,N-diacetyl)-guanine |
| monophosphate | monophosphate | monophosphate | $CF_3$ | S | 6-O-acetyl guanine |
| monophosphate | monophosphate | monophosphate | $CF_3$ | S | 8-fluoroguanine |
| monophosphate | monophosphate | monophosphate | $CF_3$ | S | guanine |
| monophosphate | monophosphate | monophosphate | $CF_3$ | S | 6-(N,N-diacetyl)-adenine |
| monophosphate | monophosphate | monophosphate | $CF_3$ | S | 2-fluoroadenine |
| monophosphate | monophosphate | monophosphate | $CF_3$ | S | 8-fluoroadenine |
| monophosphate | monophosphate | monophosphate | $CF_3$ | S | 2,8-difluoro-adenine |
| monophosphate | monophosphate | monophosphate | $CF_3$ | S | adenine |
| acetyl | acetyl | acetyl | $CF_3$ | O | guanine |
| acetyl | acetyl | acetyl | $CF_3$ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula XIV are prepared, using the appropriate sugar and pyrimidine or purine bases.

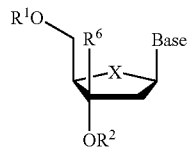

(XIV)

wherein:

| $R^1$ | $R^2$ | $R^6$ | X | Base |
|---|---|---|---|---|
| H | H | $CH_3$ | O | 2,4-O-Diacetyluracil |
| H | H | $CH_3$ | O | Hypoxanthine |
| H | H | $CH_3$ | O | 2,4-O-Diacetylthymine |
| H | H | $CH_3$ | O | Thymine |
| H | H | $CH_3$ | O | Cytosine |
| H | H | $CH_3$ | O | 4-(N-mono-acetyl)cytosine |
| H | H | $CH_3$ | O | 4-(N,N-diacetyl)cytosine |
| H | H | $CH_3$ | O | Uracil |
| H | H | $CH_3$ | O | 5-Fluorouracil |
| H | H | $CH_3$ | S | 2,4-O-Diacetyluracil |
| H | H | $CH_3$ | S | Hypoxanthine |
| H | H | $CH_3$ | S | 2,4-O-Diacetylthymine |
| H | H | $CH_3$ | S | Thymine |
| H | H | $CH_3$ | S | Cytosine |
| H | H | $CH_3$ | S | 4-(N-mono-acetyl)cytosin |
| H | H | $CH_3$ | S | 4-(N,N-diacetyl)cytosine |
| H | H | $CH_3$ | S | Uracil |
| H | H | $CH_3$ | S | 5-Fluorouracil |
| monophosphate | H | $CH_3$ | O | 2,4-O-Diacetyluracil |
| monophosphate | H | $CH_3$ | O | Hypoxanthine |
| monophosphate | H | $CH_3$ | O | 2,4-O-Diacetylthym |
| monophosphate | H | $CH_3$ | O | Thymine |
| monophosphate | H | $CH_3$ | O | Cytosine |
| monophosphate | H | $CH_3$ | O | 4-(N-mono-acetyl)cytosine |
| monophosphate | H | $CH_3$ | O | 4-(N,N-diacetyl)cytos |
| monophosphate | H | $CH_3$ | O | Uracil |
| monophosphate | H | $CH_3$ | O | 5-Fluorouracil |
| monophosphate | H | $CH_3$ | S | 2,4-O-Diacetyluracil |
| monophosphate | H | $CH_3$ | S | Hypoxanthine |
| monophosphate | H | $CH_3$ | S | 2,4-O-Diacetylthym |
| monophosphate | H | $CH_3$ | S | Thymine |
| monophosphate | H | $CH_3$ | S | Cytosine |
| monophosphate | H | $CH_3$ | S | 4-(N-mono-acetyl)cytosine |
| monophosphate | H | $CH_3$ | S | 4-(N,N-diacetyl)cytosine |
| monophosphate | H | $CH_3$ | S | Uracil |
| monophosphate | H | $CH_3$ | S | 5-Fluorouracil |
| diphosphate | H | $CH_3$ | O | 2,4-O-Diacetyluracil |
| diphosphate | H | $CH_3$ | O | Hypoxanthine |
| diphosphate | H | $CH_3$ | O | 2,4-O-Diacetylthymine |
| diphosphate | H | $CH_3$ | O | Thymine |
| diphosphate | H | $CH_3$ | O | Cytosine |
| diphosphate | H | $CH_3$ | O | 4-(N-mono-acetyl)cytosine |
| diphosphate | H | $CH_3$ | O | 4-(N,N-diacetyl)cytosine |
| diphosphate | H | $CH_3$ | O | Uracil |
| diphosphate | H | $CH_3$ | O | 5-Fluorouracil |
| diphosphate | H | $CH_3$ | S | 2,4-O-Diacetyluracil |
| diphosphate | H | $CH_3$ | S | Hypoxanthine |
| diphosphate | H | $CH_3$ | S | 2,4-O-Diacetylthymine |
| diphosphate | H | $CH_3$ | S | Thymine |
| diphosphate | H | $CH_3$ | S | Cytosine |
| triphosphate | H | $CH_3$ | O | 2,4-O-Diacetyluracil |
| triphosphate | H | $CH_3$ | O | Hypoxanthine |
| triphosphate | H | $CH_3$ | O | 2,4-O-Diacetylthymine |
| triphosphate | H | $CH_3$ | O | Thymine |
| triphosphate | H | $CH_3$ | O | Cytosine |
| triphosphate | H | $CH_3$ | O | 4-(N-mono-acetyl)cytosine |
| triphosphate | H | $CH_3$ | O | 4-(N,N-diacetyl)cytosine |
| triphosphate | H | $CH_3$ | O | Uracil |
| triphosphate | H | $CH_3$ | O | 5-Fluorouracil |

-continued

| R¹ | R² | R⁶ | X | Base |
|---|---|---|---|---|
| triphosphate | H | CH₃ | S | 2,4-O-Diacetyluracil |
| triphosphate | H | CH₃ | S | Hypoxanthine |
| triphosphate | H | CH₃ | S | 2,4-O-Diacetylthymine |
| triphosphate | H | CH₃ | S | Thymine |
| triphosphate | H | CH₃ | S | Cytosine |
| monophosphate | monophosphate | CF₃ | O | 2,4-O-Diacetyluracil |
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-mono-acetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cytosine |
| monophosphate | monophosphate | CF₃ | S | 4-(N-mono-acetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromo-vinyl | O | 4-(N,N-diacetyl)cytosine |
| acetyl | acetyl | 2-bromo-vinyl | S | 4-(N,N-diacetyl)cytosine |

Alternatively, the following nucleosides of Formula XV are prepared, using the appropriate sugar and pyrimidine or purine bases.

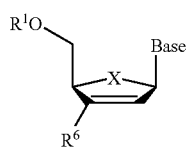

(XV)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | 4-(N,N-diacetyl)cytosine |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |

-continued

| R¹ | R⁶ | X | Base |
|---|---|---|---|
| triphosphate | CH₃ | S | 2,4-O-Diacetylthymine |
| triphosphate | CH₃ | S | Thymine |
| triphosphate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytosine |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVIII are prepared, using the appropriate sugar and pymidine or purine bases.

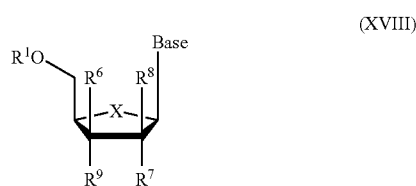

(XVIII)

wherein:

| R¹ | R⁶ | R⁷ | X | Base | R⁸ | R⁹ |
|---|---|---|---|---|---|---|
| H | CH₃ | OH | O | 2,4-O-Diacetyluracil | H | Me |
| H | CH₃ | OH | O | Hypoxanthine | H | Me |
| H | CH₃ | OH | O | 2,4-O-Diacetylthymine | H | Me |
| H | CH₃ | OH | O | Thymine | H | Me |
| H | CH₃ | OH | O | Cytosine | H | Me |
| H | CH₃ | OH | O | 4-(N-mono-acetyl)cytosine | H | Me |
| H | CH₃ | OH | O | 4-(N,N-diacetyl)cytosine | H | Me |
| H | CH₃ | OH | O | Uracil | H | Me |
| H | CH₃ | OH | O | 5-Fluorouracil | H | Me |
| H | CH₃ | OH | S | 2,4-O-Diacetyluracil | H | Me |
| H | CH₃ | OH | S | Hypoxanthine | H | Me |
| H | CH₃ | OH | S | 2,4-O-Diacetylthymine | H | Me |
| H | CH₃ | OH | S | Thymine | H | Me |
| H | CH₃ | OH | S | Cytosine | H | Me |
| H | CH₃ | OH | S | 4-(N-mono-acetyl)cytosine | H | Me |
| H | CH₃ | OH | S | 4-(N,N-diacetyl)cytosine | H | Me |
| H | CH₃ | OH | S | Uracil | H | Me |
| H | CH₃ | OH | S | 5-Fluorouracil | H | Me |
| monophosphate | CH₃ | OH | O | 2,4-O-Diacetyluracil | H | Me |
| monophosphate | CH₃ | OH | O | Hypoxanthine | H | Me |
| monophosphate | CH₃ | OH | O | 2,4-O-Diacetylthymine | H | Me |
| monophosphate | CH₃ | OH | O | Thymine | H | Me |
| monophosphate | CH₃ | OH | O | Cytosine | H | Me |
| monophosphate | CH₃ | OH | O | 4-(N-mono-acetyl)cytosine | H | Me |
| monophosphate | CH₃ | OH | O | 4-(N,N-diacetyl)cytosine | H | Me |
| monophosphate | CH₃ | OH | O | Uracil | H | Me |
| monophosphate | CH₃ | OH | O | 5-Fluorouracil | H | Me |
| monophosphate | CH₃ | OH | S | 2,4-O-Diacetyluracil | H | Me |
| monophosphate | CH₃ | OH | S | Hypoxanthine | H | Me |
| monophosphate | CH₃ | OH | S | 2,4-O-Diacetylthymine | H | Me |
| monophosphate | CH₃ | OH | S | Thymine | H | Me |
| monophosphate | CH₃ | OH | S | Cytosine | H | Me |
| monophosphate | CH₃ | OH | S | 4-(N-mono-acetyl)cytosine | H | Me |
| monophosphate | CH₃ | OH | S | 4-(N,N-diacetyl)cytosine | H | Me |
| monophosphate | CH₃ | OH | S | Uracil | H | Me |
| monophosphate | CH₃ | OH | S | 5-Fluorouracil | H | Me |
| diphosphate | CH₃ | OH | O | 2,4-O-Diacetyluracil | H | Me |
| diphosphate | CH₃ | OH | O | Hypoxanthine | H | Me |
| diphosphate | CH₃ | OH | O | 2,4-O-Diacetylthymine | H | Me |
| diphosphate | CH₃ | OH | O | Thymine | H | Me |
| diphosphate | CH₃ | OH | O | Cytosine | H | Me |
| diphosphate | CH₃ | OH | O | 4-(N-mono-acetyl)cytosine | H | Me |
| diphosphate | CH₃ | OH | O | 4-(N,N-diacetyl)cytosine | H | Me |
| diphosphate | CH₃ | OH | O | Uracil | H | Me |
| diphosphate | CH₃ | OH | O | 5-Fluorouracil | H | Me |
| diphosphate | CH₃ | OH | S | 2,4-O-Diacetyluracil | H | Me |
| diphosphate | CH₃ | OH | S | Hypoxanthine | H | Me |
| diphosphate | CH₃ | OH | S | 2,4-O-Diacetylthymine | H | Me |
| diphosphate | CH₃ | OH | S | Thymine | H | Me |
| diphosphate | CH₃ | OH | S | Cytosine | H | Me |
| triphosphate | CH₃ | OH | O | 2,4-O-Diacetyluracil | H | Me |
| triphosphate | CH₃ | OH | O | Hypoxanthine | H | Me |
| triphosphate | CH₃ | OH | O | 2,4-O-Diacetylthymine | H | Me |
| triphosphate | CH₃ | OH | O | Thymine | H | Me |
| triphosphate | CH₃ | OH | O | Cytosine | H | Me |
| triphosphate | CH₃ | OH | O | 4-(N-mono-acetyl)cytosine | H | Me |
| triphosphate | CH₃ | OH | O | 4-(N,N-diacetyl)cytosine | H | Me |
| triphosphate | CH₃ | OH | O | Uracil | H | Me |
| triphosphate | CH₃ | OH | O | 5-Fluorouracil | H | Me |
| triphosphate | CH₃ | OH | S | 2,4-O-Diacetyluracil | H | Me |
| triphosphate | CH₃ | OH | S | Hypoxanthine | H | Me |
| triphosphate | CH₃ | OH | S | 2,4-O-Diacetylthymine | H | Me |
| triphosphate | CH₃ | OH | S | Thymine | H | Me |
| triphosphate | CH₃ | OH | S | Cytosine | H | Me |
| monophosphate | CF₃ | OH | O | 2,4-O-Diacetyluracil | H | Me |
| monophosphate | CF₃ | OH | O | Hypoxanthine | H | Me |
| monophosphate | CF₃ | OH | O | 2,4-O-Diacetylthymine | H | Me |
| monophosphate | CF₃ | OH | O | Thymine | H | Me |
| monophosphate | CF₃ | OH | O | Cytosine | H | Me |
| monophosphate | CF₃ | OH | O | 4-(N-mono-acetyl)cytosine | H | Me |
| monophosphate | CF₃ | OH | O | 4-(N,N-diacetyl)cytosine | H | Me |
| monophosphate | CF₃ | OH | O | Uracil | H | Me |
| monophosphate | CF₃ | OH | O | 5-Fluorouracil | H | Me |
| monophosphate | CF₃ | OH | S | 2,4-O-Diacetyluracil | H | Me |
| monophosphate | CF₃ | OH | S | Hypoxanthine | H | Me |
| monophosphate | CF₃ | OH | S | 2,4-O-Diacetylthymine | H | Me |
| monophosphate | CF₃ | OH | S | Thymine | H | Me |
| monophosphate | CF₃ | OH | S | Cytosine | H | Me |
| monophosphate | CF₃ | OH | S | 4-(N-mono-acetyl)cytosine | H | Me |
| monophosphate | CF₃ | OH | S | 4-(N,N-diacetyl)cytosine | H | Me |
| monophosphate | CF₃ | OH | S | Uracil | H | Me |
| monophosphate | CF₃ | OH | S | 5-Fluorouracil | H | Me |
| acetyl | CH₃ | OH | O | 4-(N,N-diacetyl)cytosine | H | Br |
| acetyl | CH₃ | OH | S | 4-(N,N-diacetyl)cytosine | H | Br |

VII. Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al., *Jnl. of Vir.*, 73:1649–1654, 1999; Ishii et al., *Hepatology*, 29:1227–1235, 1999; Lohmann et al., *Jnl. of Bio. Chem.*, 274:10807–10815, 1999; and Yamashita et al, *Jnl. of Bio. Chem.*, 273:15479–15486, 1998.

WO 97/12033, filed on Sep. 27, 1996, by Emory University, listing C. Hagedom and A. Reinoldus as inventors, and which claims priority to U.S. Ser. No. 60/004,383, filed on September 1995, describes an HCV polymerase assay that can be used to evaluate the activity of the compounds described herein. Another HCV polymerase assay has been reported by Bartholomeusz, et al., Hepatitis C virus (HCV) RNA polymerase assay using cloned HCV non-structural proteins; Antiviral Therapy 1996:1 (Supp 4) 18–24.

Screens that measure reductions in kinase activity from HCV drugs are disclosed in U.S. Pat. No. 6,030,785, to Katze et al., U.S. Pat. No. 6,010,848 to Delvecchio et al, and U.S. Pat. No. 5,759,795 to Jubin et al. Screens that measure the protease inhibiting activity of proposed HCV drugs are disclosed in U.S. Pat. No. 5,861,267 to Su et al, U.S. Pat. No. 5,739,002 to De Francesco et al, and U.S. Pat. No. 5,597,691 to Houghton et al.

Example 4

Phosphorylation Assay of Nucleoside to Active Triphosphate

To determine the cellular metabolism of the compounds, HepG2 cells were obtained from the American Type Culture Collection (Rockville, Md.), and were grown in 225 cm$^2$ tissue culture flasks in minimal essential medium supplemented with non-essential amino acids, 1% penicillin-streptomycin. The medium was renewed every three days, and the cells were subcultured once a week. After detachment of the adherent monolayer with a 10 minute exposure to 30 mL of trypsin-EDTA and three consecutive washes with medium, confluent HepG2 cells were seeded at a density of 2.5×10$^6$ cells per well in a 6-well plate and exposed to 10 μM of [$^3$H] labeled active compound (500 dpm/pmol) for the specified time periods. The cells were maintained at 37° C. under a 5% CO$_2$ atmosphere. At the selected time points, the cells were washed three times with ice-cold phosphate-buffered saline (PBS). Intracellular active compound and its respective metabolites were extracted by incubating the cell pellet overnight at −20° C. with 60% methanol followed by extraction with an additional 20 μL of cold methanol for one hour in an ice bath. The extracts were then combined, dried under gentle filtered air flow and stored at −20° C. until HPLC analysis. The preliminary results of the HPLC analysis are tabulated in Table 1.

TABLE 1

| | [pmol/million cells] | | | |
|---|---|---|---|---|
| Time (h) | β-D-2'-CH$_3$-riboA-TP | β-D-2'-CH$_3$-riboU-TP | β-D-2'-CH$_3$-riboC-TP | β-D-2'-CH$_3$-riboG-TP |
| 2 | 33.1 | 0.40 | 2.24 | ND |
| 4 | 67.7 | 1.21 | 3.99 | ND |
| 8 | 147 | 1.57 | 9.76 | 2.85 |
| 24 | 427 | 6.39 | 34.9 | 0.91 |
| 30 | 456 | 7.18 | 36.2 | 3.22 |
| 48 | 288 | 9.42 | 56.4 | 6.26 |

Example 5

Bioavailability Assay in Cynomolgus Monkeys

Figure 3A:
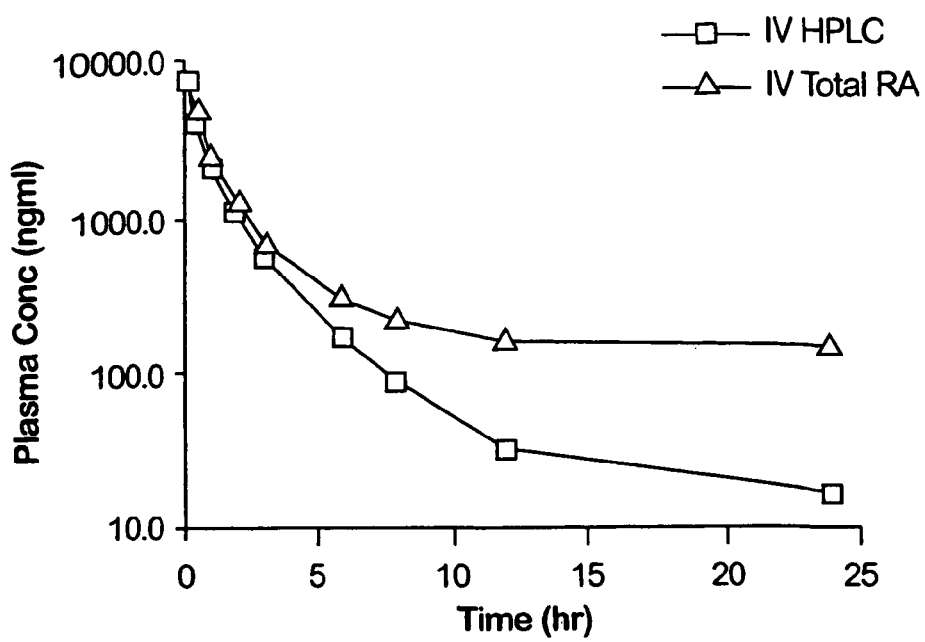
FIGS. 3a and 3b are line graphs of the pharmacokinetics (plasma concentrations) of β-D-2'-CH$_3$-riboG administered to Cynomolgus Monkeys either intravenously (3a) or orally (3b) over time after administration.
Figure 3B:
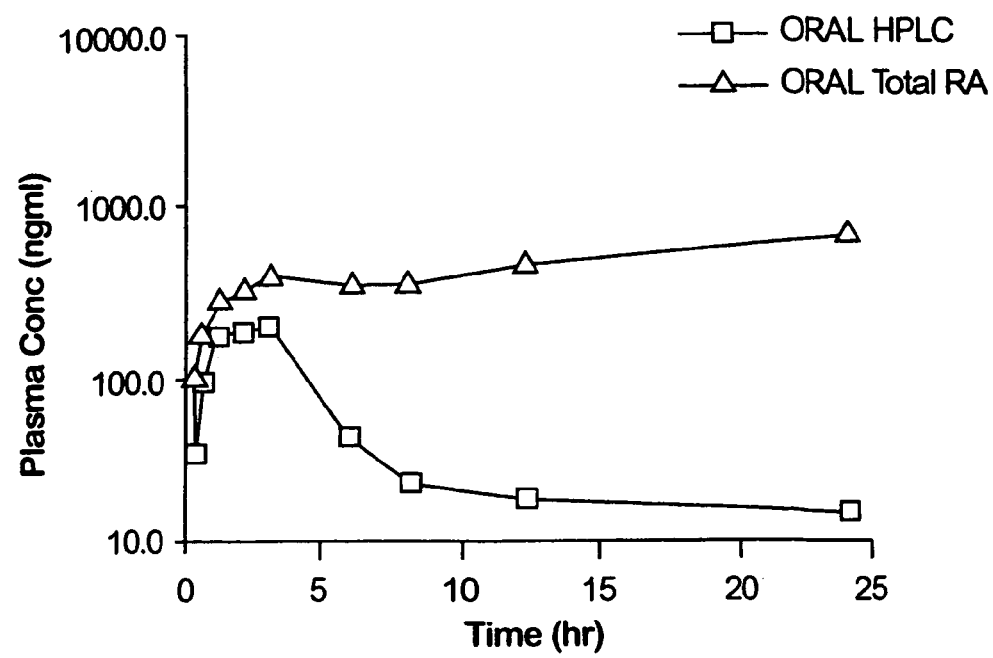

Within 1 week prior to the study initiation, the cynomolgus monkey was surgically implanted with a chronic venous catheter and subcutaneous venous access port (VAP) to facilitate blood collection and underwent a physical examination including hematology and serum chemistry evaluations and the body weight was recorded. Each monkey (six total), received approximately 250 uCi of $^3$H activity with each dose of active compound, namely β-D-2'-CH$_3$-riboG at a dose level of 10 mg/kg at a dose concentration of 5 mg/mL, either via an intravenous bolus (3 monkeys, IV), or via an oral gavage (3 monkeys, PO). Each dosing syringe was weighed before dosing to gravimetrically determine the quantity of formulation administered. Urine samples were collected via pan catch at the designated intervals (approximately 18–0 hours pre-dose, 0–4, 4–8 and 8–12 hours post-dosage) and processed. Blood samples were collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples were analyzed for the maximum concentration ($C_{max}$), time when the maximum concentration was achieved ($T_{max}$), area under the curve (AUC), half life of the dosage concentration ($T_{1/2}$), clearance (CL), steady state volume and distribution ($V_{ss}$) and bioavailibility (F), which are tabulated in Tables 2 and 3, and graphically illustrated in FIGS. 2 and 3, respectively.

TABLE 2

Oral Bioavailability in Monkeys

| | Dose (mg) | AUC (ng/mL × h) | Norm AUC (ng/mL × h/mg) | Mean Norm AUC (ng/mL × h/mg) | F (%) |
|---|---|---|---|---|---|
| IV Monkey 1 | 46.44 | 13614 | 293.2 | | |
| IV Monkey 2 | 24.53 | 6581 | 268.3 | | |
| IV Monkey 3 | 20.72 | 6079 | 293.4 | 284.9 | |
| PO Monkey 1 | 29.04 | 758 | 26.1 | | |
| PO Monkey 2 | 30.93 | 898 | 29.0 | | |
| PO Monkey 3 | 30.04 | 1842 | 61.3 | 38.8 | 13.6 |

TABLE 3

Experimental Pharmacokinetics of β-D-2'-CH$_3$-riboG in Cynomolgus Monkeys

| | IV | PO |
|---|---|---|
| Dose/Route (mg/kg) | 10 | 10 |
| $C_{max}$ (ng/mL) | 6945.6 ± 1886.0 | 217.7 ± 132.1 |
| $T_{max}$ (hr) | 0.25 ± 0.00 | 2.00 ± 1.00 |
| AUC (ng/mL × hr) | 8758.0 ± 4212.9 | 1166.0 ± 589.6 |
| $T_{1/2}$ (hr) | 7.9 ± 5.4 | 10.3 ± 4.1 |
| CL (L/hr/kg) | 1.28 ± 0.48 | |
| $V_{ss}$ (L/kg) | 2.09 ± 0.54 | |
| F (%) | | 13.8 |

Example 6

Bone Marrow Toxicity Assay

Human bone marrow cells were collected from normal healthy volunteers and the mononuclear population was separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452–454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921–1925. The culture assays for CFU-GM and BFU-E were performed using a bilayer soft agar or methylcellulose method. Drugs were diluted in tissue culture medium and filtered. After 14 to 18 days at 37° C. in a humidified atmosphere of 5% $CO_2$ in air, colonies of greater than 50 cells were counted using an inverted microscope. The results in Table 4 are presented as the percent inhibition of colony formation in the presence of drug compared to solvent control cultures.

TABLE 4

Human Bone Marrow Toxicity CFU-GM and BFU-E Clonogenic Assays

| Treatment | $IC_{50}$ in μM | |
|---|---|---|
| | CFU-GM | BFU-E |
| ribavirin | ~5 | ~1 |
| β-D-2'-$CH_3$-riboA | >100 | >100 |
| β-D-2'-$CH_3$-riboU | >100 | >100 |
| β-D-2'-$CH_3$-riboC | >10 | >10 |
| β-D-2'-$CH_3$-riboG | >10 | >100 |

Example 7

Mitochondria Toxicity Assay

HepG2 cells were cultured in 12-well plates as described above and exposed to various concentrations of drugs as taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob Agents Chemother 2000; 44:496–503. Lactic acid levels in the culture medium after 4 day drug exposure was measured using a Boehringer lactic acid assay kit. Lactic acid levels were normalized by cell number as measured by hemocytometer count. The preliminary results from this assay are tabulated in Table 5.

TABLE 5

Mitochondrial Toxicity Study (L-lactic acid assay)

| | Conc. (μM) | lactate (mg/$10^6$ cell) | % of Control |
|---|---|---|---|
| Control | | 2.18 | |
| FIAU | 10 | 3.73 | 170.4 |
| β-D-2'-$CH_3$-riboC | 1 | 2.52 | 115.3 |
| | 10 | 2.36 | 107.9 |
| | 50 | 2.26 | 103.4 |
| | 100 | 2.21 | 101.2 |

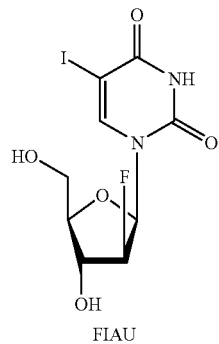

FIAU

TABLE 5-continued

Mitochondrial Toxicity Study (L-lactic acid assay)

Conc. (μM)    lactate (mg/$10^6$ cell)    % of Control

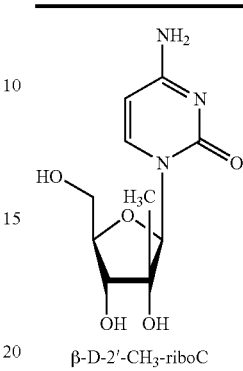

β-D-2'-$CH_3$-riboC

This invention has been described with reference to its preferred embodiments. Variations and modifications of the invention, will be obvious to those skilled in the art from the foregoing detailed description of the invention.

The invention claimed is:

1. A method for the treatment of a hepatitis C virus infection in a host, comprising administering an anti-virally effective amount of a compound of Formula XVII:

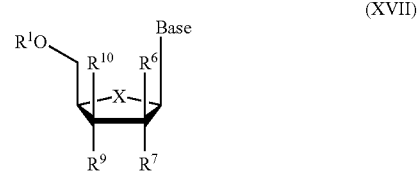

(XVII)

or a pharmaceutically acceptable salt or ester thereof, wherein:

Base is a purine;

$R^1$ and $R^2$ are independently H; phosphate; a stabilized phosphate prodrug; acyl; or pharmaceutically acceptable leaving group which when administered in vivo is capable of providing a compound wherein $R^1$ and $R^2$ are independently H or phosphate;

$R^6$ is, alkyl, $R^7$ and $R^9$ are independently hydrogen, $OR^2$, hydroxy, alkyl, azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, or —N(acyl)$_2$;

$R^{10}$ is H, alkyl, chlorine, bromine or iodine;

alternatively, $R^7$ and $R^9$, or $R^7$ and $R^{10}$ can come together to form a bond; and X is O.

2. The method of claim 1 for the treatment of a hepatitis C virus infection in a host, comprising administering an anti-virally effective amount of a compound of Formula II:

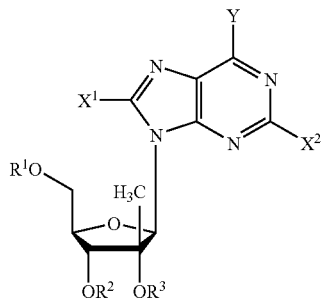

(II)

or a pharmaceutically acceptable salt or ester thereof, wherein:

$R^1$, $R^2$ and $R^3$ are independently H; phosphate or a stabilized phosphate prodrug; acyl; or pharmaceutically acceptable leaving group which when administered in vivo is capable of providing a compound wherein $R^1$, $R^2$ and $R^3$ are independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

3. The method of claim 1 for the treatment of a hepatitis C virus infection in a host, comprising administering an anti-virally effective amount of a compound of Formula X or XI:

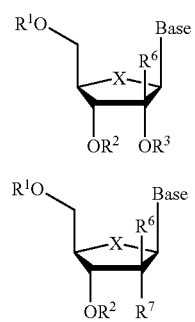

(X)

(XI)

or a pharmaceutically acceptable salt or ester thereof, wherein:

Base is a purine;

$R^1$, $R^2$ and $R^3$ are independently H; phosphate or a stabilized phosphate prodrug; acyl; or pharmaceutically acceptable leaving group which when administered in vivo is capable of providing a compound wherein $R^1$, $R^2$ and $R^3$ are independently H or phosphate;

$R^6$ is hydroxy, alkyl, azido, cyano, alkenyl, alkynyl, Br-vinyl, —(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, or —N(acyl)$_2$;

$R^7$ is hydrogen, $OR^3$, alkyl, and

X is O.

4. The method of claim 1 for the treatment of a hepatitis C virus infection in a host, wherein, in the compound of Formula XVII:

$R^{10}$ is H, alkyl, chlorine, bromine or iodine;

$R^7$ and $R^9$ are independently hydrogen, $OR^2$, alkyl, alkenyl, alkynyl, Br-vinyl, O-alkenyl, chlorine, bromine, iodine, $NO_2$, $NH_2$, —NH(lower alkyl), —NH(acyl), —N(lower alkyl)$_2$, or —N(acyl)$_2$;

$R^6$ is alkyl, chlorine, bromine or iodine;

alternatively, $R^7$ and $R^9$, or $R^8$ and $R^9$ can come together to form a bond; and X is O, S, $SO_2$ or $CH_2$.

5. The method of claim 1 wherein $R^1$ is hydrogen or phosphate.

6. The method of claim 1 wherein $R^2$ is hydrogen, of acyl.

7. The method of claim 1 wherein $R^7$ and $R^9$ are independently hydrogen, $OR^2$, or hydroxy.

8. The method of claim 1, wherein $R^7$ is hydroxy.

9. The method of claim 1 wherein $R^9$ is hydroxy.

10. The method of claim 1 wherein $R^7$ and $R^9$ are hydroxy.

11. The method of claim 1 wherein $R^{10}$ is hydrogen.

12. The method of claim 1 wherein $R^1$ is hydrogen or phosphate;

$R^2$ is hydrogen, acyl or alkyl;

$R^6$ is alkyl;

$R^7$ and $R^9$ are independently hydrogen, $OR^2$, or hydroxy;

$R^{10}$ is hydrogen; and

X is O.

13. The method of claim 1, wherein the base is a purine selected from the group consisting of $N^6$-alkylpurines, $N^6$-acylpurines, $N^6$-halopurine, $N^6$-vinylpurine, $N^6$-acetylenic purine, $N^6$-acyl purine, $N^6$-hydroxyalkyl purine, $N^6$-thioalkyl purine, N 2-alkylpurines, $N^2$-alkyl-6-thiopurines, $N^2$-alkylpurines, $N^2$-alkyl-6-thiopurines, 5-azacytidinyl, guanine, adenine, hypoxanthine, 2,6-diaminopurine, and 6-chloropurine.

14. The method of claim 1 for the treatment of a hepatitis C virus infection in a host, comprising administering an antivirally effective amount of a compound of the structure:

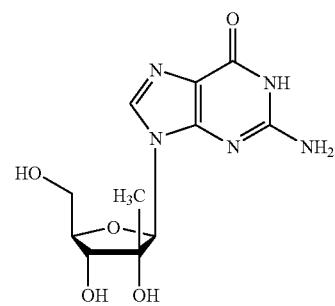

or a pharmaceutically acceptable salt or ester thereof.

15. The method of claim 1 for the treatment of a hepatitis c virus infection in a host, comprising administering an antivirally effective amount of a compound of the structure:

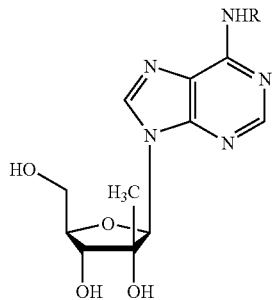

or a pharmaceutically acceptable salt or ester thereof, wherein R is hydrogen or alkyl.

16. The method of claim 15, wherein R is methyl, ethyl, propyl, isopropyl, or cyclopropyl.

17. The method of claim 15, wherein R is butyl, isobutyl, t-butyl, pentyl, cyclopentyl, isopentyl, or neopentyl.

18. The method of claim 1 for the treatment of a hepatitis C virus infection in a host, comprising administering an antivirally effective amount of a compound of the structure:

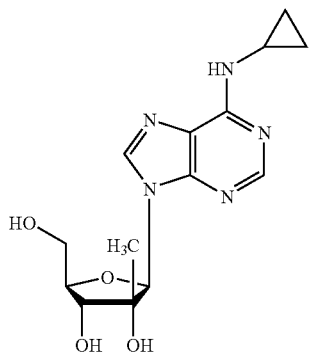

or a pharmaceutically acceptable salt or ester thereof.

19. The method of claim 1 for the treatment of a hepatitis C virus infection in a host, comprising administering an antivirally effective amount of a compound of the structure:

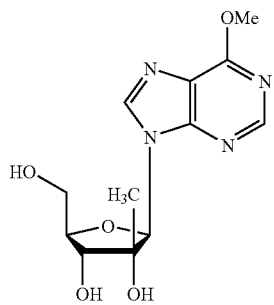

or a pharmaceutically acceptable salt or ester thereof.

20. The method of claim 1 for the treatment of a hepatitis C virus infection in a host, comprising administering an antivirally effective amount of a compound of the structure:

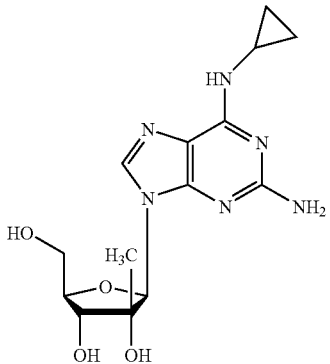

or a pharmaceutically acceptable salt or ester thereof.

21. The method of claim 1 for the treatment of a hepatitis C virus infection in a host, comprising administering an antivirally effective amount of a compound of the structure:

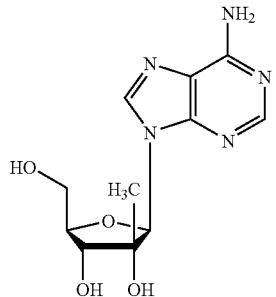

or a pharmaceutically acceptable salt or ester thereof.

22. The method of claim 1 for the treatment of a hepatitis C virus infection in a host, comprising administering an antivirally effective amount of a compound of the structure:

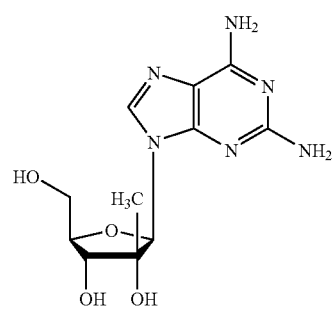

or a pharmaceutically acceptable salt or ester thereof.

23. The method of claim 1 for the treatment of a hepatitis C virus infection in a host, comprising administering an antivirally effective amount of a compound of the structure:

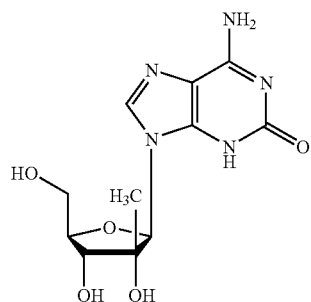

or a pharmaceutically acceptable salt or ester thereof.

24. The method of claim 1 for the treatment of a hepatitis C virus infection in a host, comprising administering an antivirally effective amount of a compound of the structure:

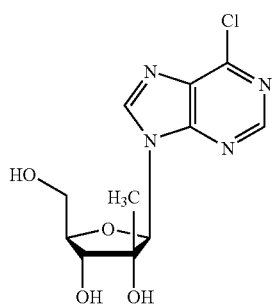

or a pharmaceutically acceptable salt or ester thereof.

25. The method of claim 1 for the treatment of a hepatitis C virus infection in a host, comprising administering an antivirally effective amount of a compound of the structure:

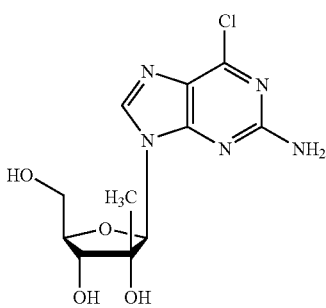

or a pharmaceutically acceptable salt or ester thereof.

26. The method of claim 1 for the treatment of a hepatitis C virus infection in a host, comprising administering an antivirally effective amount of a compound of the structure:

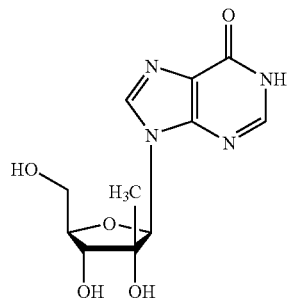

or a pharmaceutically acceptable salt or ester thereof.

27. The method of claim 1 for the treatment of a hepatitis C virus infection in a host, wherein the purine base is selected from the group consisting of

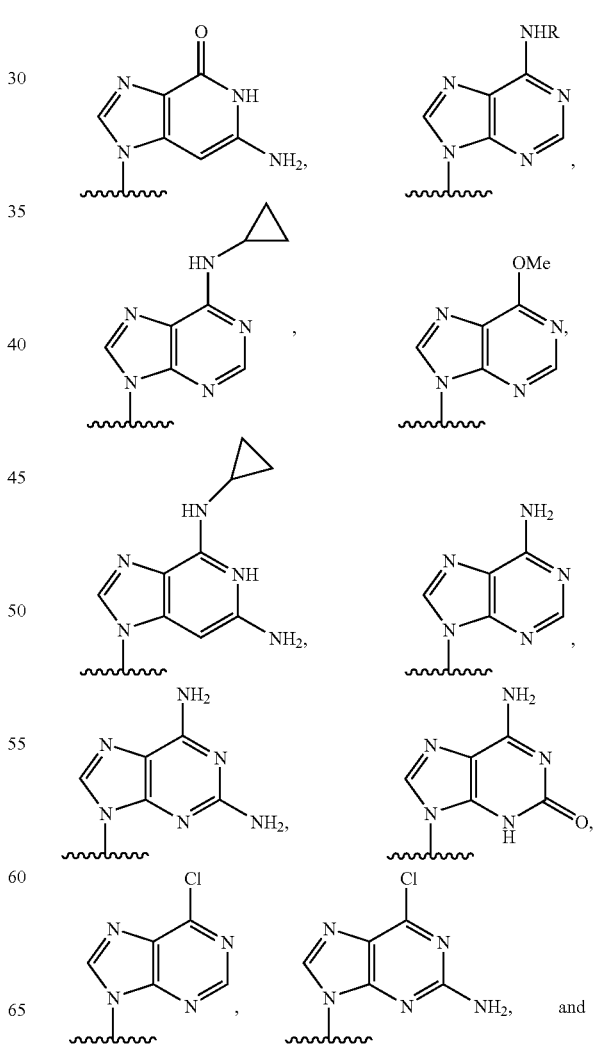

-continued

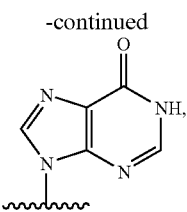

wherein R
is methyl, ethyl, propyl, isopropyl, butyl, isobutyl, t-butyl, pentyl, cyclopentyl, isopentyl, or neopentyl.

28. The method of claim 1, wherein the method comprises administering the compound or a pharmaceutically acceptable salt or ester thereof in combination or alternation with a second anti-hepatitis C virus agent.

29. The method of claim 28, wherein the second anti-hepatitis C virus agent is selected from the group consisting of consisting of interferon, ribavirin, a protease inhibitor, a thiazolidine derivative, a polymerase inhibitor, and a helicase inhibitor.

30. The method of claim 29, wherein the second anti-hepatitis C virus agent is interferon.

31. The method of claim 29, wherein the second anti-hepatitis C virus agent is a protease inhibitor.

32. The method of claim 29, wherein the second anti-hepatitis C virus agent is ribavirin.

33. The method of claim 1, wherein the compound is in the form of a dosage unit.

34. The method of claim 33, wherein the dosage unit contains 50 to 1000 mg of said compound.

35. The method of claim 33, wherein said dosage unit is a tablet or capsule.

36. The method of claim 1, wherein the host is a human.

37. The method of claim 1, wherein the compound is in substantially pure form.

38. The method of claim 1, wherein the compound is at least 90% by weight of the β-D-isomer.

39. The method of claim 1, wherein the compound is at least 95% by weight of the β-D-isomer.

* * * * *

UNITED STATES PATENT AND TRADEMARK OFFICE
CERTIFICATE OF CORRECTION

| | | |
|---|---|---|
| PATENT NO. | : 7,157,441 B2 | Page 1 of 1 |
| APPLICATION NO. | : 10/602136 | |
| DATED | : January 2, 2007 | |
| INVENTOR(S) | : Jean-Pierre Sommadossi et al. | |

It is certified that error appears in the above-identified patent and that said Letters Patent is hereby corrected as shown below:

Column 148, claim 1, line 54, replace "$R^6$ is, alkyl," with -- $R^6$ is alkyl; --.

Column 150, claim 6, line 22, replace "hydrogen, of acyl" with -- hydrogen, or acyl. --.

Signed and Sealed this

Twenty-fourth Day of April, 2007

JON W. DUDAS
*Director of the United States Patent and Trademark Office*